United States Patent
Collmer et al.

(10) Patent No.: US 7,138,569 B2
(45) Date of Patent: Nov. 21, 2006

(54) NUCLEIC ACIDS ENCODING PSEUDOMONAS HOP PROTEINS AND USE THEREOF

(75) Inventors: Alan Collmer, Ithaca, NY (US); James R. Alfano, Lincoln, NE (US); Xiaoyan Tang, Manhattan, KS (US); C. Robin Buell, Olney, MD (US); Gregory B. Martin, Ithaca, NY (US)

(73) Assignees: Cornell Research Foundation, Inc., Ithaca, NY (US); Kansas State University Research Foundation, Manhattan, KS (US); Boyce Thompson Institute for Plant Research, Inc., Ithaca, NY (US); The Institute for Genomic Research, Rockville, MD (US); The Board of Regents of the University of Nebraska, Lincoln, NE (US)

( * ) Notice: Subject to any disclaimer, the term of this patent is extended or adjusted under 35 U.S.C. 154(b) by 226 days.

(21) Appl. No.: 10/114,828

(22) Filed: Apr. 2, 2002

(65) Prior Publication Data

US 2003/0182681 A1    Sep. 25, 2003

Related U.S. Application Data

(60) Provisional application No. 60/280,918, filed on Apr. 2, 2001, provisional application No. 60/356,408, filed on Feb. 12, 2002.

(51) Int. Cl.
*C12N 15/82* (2006.01)
*C12N 15/31* (2006.01)
*C12N 15/63* (2006.01)

(52) U.S. Cl. .................. 800/301; 800/279; 536/23.7; 424/93.2; 435/320.1; 435/252.3

(58) Field of Classification Search ............ 800/301; 536/23.7; 435/252.3, 418, 252.2
See application file for complete search history.

(56) References Cited

U.S. PATENT DOCUMENTS 6,342,654 B1    1/2002    Li et al.

OTHER PUBLICATIONS

Lazar et al, 1988, Mol. Cell. Biol. 8:1247-1252.*
Hill et al, 1998, Biochem. Biophys. Res. Comm. 244:573-577.*
Keller et al, 1999, Plant Cell 11:223-235.*
Bauer et al. 1999, Acta Hort. 489:301-304.*
Espinosa et al, 2003, Molec. Microlbiol. 49:377-387.*
Collmer et al., "*Pseudomonas syringae* Hrp Type III Secretion System and Effector Proteins," *PNAS* 97(16):8770-8777 (2000).
Alfano et al., "The *Pseudomonas syringae* Hrp Pathogenicity Island has a Tripartite Mosaic Structure Composed of a Cluster of Type III Secretion Genes Bounded by Exchangeable Effector and Conserved Effector Loci That Contribute to Parasitic Fitness and Pathogenicity in Plants," *PNAS* 97(9):4856-4861 (2000).
Fouts et al., "Genomewide Identification of *Pseudomonas syringae* pv. Tomato DC3000 Promoters Controlled by the HrpL Alternative Sigma Factor," *PNAS* 99(4):2275-2280 (2002), with supplemental material available online at www.pnas.org.
Petnicki-Ocwieja et al., "Genomewide Identification of Proteins Secreted by the Hrp Type III Protein Secretion System of *Pseudomonas syringae* pv. Tomato DC3000," *PNAS* 99(11):7652-7657 (2002), with supplemental material available online at www.pnas.org.

* cited by examiner

*Primary Examiner*—Anne Kubelik
(74) *Attorney, Agent, or Firm*—Nixon Peabody LLP

(57) ABSTRACT

The present invention relates to isolated nucleic acid molecules encoding a type III—secreted bacterial protein capable of modifying a cell death pathway in a plant cell. One aspect of the present invention involves an isolated nucleic acid molecule having a nucleotide sequence that encodes the HopPtoD2 protein of *Pseudomonas syringae* pv. *syringae* DC 3000. Expression vectors, host cells, and transgenic plants which include the DNA molecules of the present invention are also disclosed. The nucleic acid molecules of the present invention can be used to impart disease resistance to a plant and to make a plant hypersusceptible to colonization by nonpathogenic bacteria.

12 Claims, 1 Drawing Sheet understand ability to produce either of these reactions in plants appears to be directed by hrp (HR and pathogenicity) and hrc (HR and conserved) genes that encode a type III protein secretion pathway and by avr (avirulence) and hop (Hrp-dependent outer protein) genes# NUCLEIC ACIDS ENCODING PSEUDOMONAS HOP PROTEINS AND USE THEREOF This application claims benefit of U.S. Provisional Patent Application Ser. Nos. 60/280,918, filed Apr. 2, 2001, and 60/356,408, filed Feb. 12, 2002, each of which is hereby incorporated by reference in its entirety.

This work was supported by National Science Foundation Grant Nos. DBI-0077622 and MCB-9982646 and National Research Initiative Competitive Grants Program, U.S. Department of Agriculture, Grant Nos. 97-35303-4488 and 01-35319-10019. The U.S. Government may have certain rights in this invention.

FIELD OF THE INVENTION

The present invention relates to isolated DNA molecules corresponding to the open reading frames of *Pseudomonas syringae* pv. tomato DC3000, the isolated avirulence effector proteins and hrp-dependent outer proteins encoded thereby, as well as their various uses.

BACKGROUND OF THE INVENTION

The plant pathogenic bacterium *Pseudomonas syringae* is noted for its diverse and host-specific interactions with plants. A specific strain may be assigned to one of at least 40 pathovars based on its host range among different plant species and then further assigned to a race based on differential interactions among cultivars of the host. In host plants the bacteria typically grow to high population levels in leaf intercellular spaces and then produce necrotic lesions. In nonhost plants or in host plants with race-specific resistance, the bacteria elicit the hypersensitive response (HR), a rapid, defense-associated programmed death of plant cells in contact with the pathogen (Alfano & Collmer, *J. Bacteriol.* 179:5655–5662 (1997)). The ability to produce either of these reactions in plants appears to be directed by hrp (HR and pathogenicity) and hrc (HR and conserved) genes that encode a type III protein secretion pathway and by avr (avirulence) and hop (Hrp-dependent outer protein) genes that encode effector proteins injected into plant cells by the pathway (Alfano & Collmer, *J. Bacteriol.* 179:5655–5662 (1997)). These effectors may also betray the parasite to the HR-triggering R-gene surveillance system of potential hosts (hence the avr designation), and plant breeding for resistance based on such gene-for-gene (avr-R) interactions may produce complex combinations of races and differential cultivars (Keen, *Annu. Rev. Genet.* 24:447–463 (1990)). hrp/hrc genes are probably universal among necrosis-causing gram-negative plant pathogens, and they have been sequenced in *P. syringae* pv. *syringae* (Psy) 61, *Erwinia amylovora* Ea321, *Xanthomonas campestris* pv. *vesicatoria* (Xcv) 85–10, and *Ralstonia solanacearum* GMI1000 (Alfano & Collmer, *J. Bacteriol.* 179:5655–5662 (1997)). Based on their distinct gene arrangements and regulatory components, the hrp/hrc gene clusters of these four bacteria can be divided into two groups: I (*Pseudomonas* and *Erwinia*) and II (*Xanthomonas* and *Ralstonia*). The discrepancy between the distribution of these groups and the phylogeny of the bacteria provides some evidence that hrp/hrc gene clusters have been horizontally acquired and, therefore, may represent pathogenicity islands (Pais) (Alfano & Collmer, *J. Bacteriol.* 179:5655–5662 (1997)).

Virulence effector proteins delivered to or into host cells by type III secretion systems are key factors in the pathogenicity of many bacteria, including animal pathogens in the genera *Salmonella*, *Yersinia*, *Shigella*, and *Escherichia*, and plant pathogens in the genera *Pseudomonas*, *Erwinia*, *Xanthomonas*, *Ralstonia*, and *Pantoea* (Galán & Collmer, *Science* 284:1322–1328 (1999)). In plant pathogens, the type III secretion machinery is referred to as the hypersensitive response and pathogenicity (Hrp) system because secretion mutants typically lose their ability to elicit the defense-associated hypersensitive response in nonhost plants and to grow parasitically or be pathogenic in host plants (Alfano & Collmer, *J. Bacteriol.* 179:5655–5662 (1997)). These phenotypes demonstrate the importance of the Hrp system in bacterium-plant interactions, and global identification of effectors will be important for understanding the pathogenesis of bacteria that use type III secretion systems. Unfortunately, several factors have hindered searches for type III effector genes. These factors include: (i) effectors are often redundant with mutants having only subtle phenotypes; (ii) with few exceptions (see e.g., Miao & Miller, *Proc. Natl. Acad. Sci. USA* 97:7539–7544 (2000)) motifs that can identify proteins as substrates for type III secretion have not been recognized (Lloyd et al., *Mol. Microbiol.* 39:520–532) (2001); (iii) many effectors show no similarity to known proteins; and (iv) some pathogens have multiple type III secretion systems which deliver different sets of effectors (Cornelis & Van Gijsegem, *Annu. Rev. Microbiol.* 54:735–774 (2000)). Thus, a complete inventory of type III effector genes is lacking for any pathogen, although it seems that pathogens such as *Salmonella* may have many such genes (Worley et al., *Mol. Microbiol.* 36:749–761 (2000)).

Plant pathogen type III effector proteins are mostly designated Avr or Hop, depending on whether their primary phenotype involves plant reaction or secretion behavior. Many effectors were initially discovered through their ability to betray the pathogen to the host R (resistance) gene surveillance system, thereby rendering the pathogen avirulent on a test plant (Keen, *Annu. Rev. Genet.* 24:447–463 (1990)). Over 25 effector genes have been identified by Avr or Hop phenotypes in various *P. syringae* pathovars and races (Vivian & Arnold, *J. Plant Pathol.* 82:163–178 (2000); Alfano et al., *Proc. Natl. Acad. Sci. USA* 97:4856–4861 (2000)). The encoded effectors seem to determine both basic pathogenicity and host range, but the number of such proteins produced by any single strain has not been systematically investigated. P. s. tomato DC3000 is known to carry at least three avr genes, avrPto (Ronald et al., *J. Bacteriol.* 174:1604–1611 (1992)), avrPtoB, and avrE (Lorang & Keen, *Mol. Plant-Microbe Interact.* 8:49–57 (1995)), with the latter being in the Hrp pathogenicity island along with five other candidate effector genes (Alfano et al., *Proc. Natl. Acad. Sci. USA* 97:4856–486 (2000); Lorang & Keen, *Mol. Plant-Microbe Interact.* 8:49–57 (1995)).

The present invention is a further advance in the effort to identify, clone, and sequence Avr and Hop proteins or polypeptides from plant pathogens.

SUMMARY OF THE INVENTION

One aspect of the present invention relates to isolated nucleic acid molecules having a nucleotide sequence which (i) encodes a protein or polypeptide including SEQ ID No: 2, SEQ ID No: 4, SEQ ID No: 6, SEQ ID No: 8, SEQ ID No: 10, SEQ ID No: 12, SEQ ID No: 14, SEQ ID No: 16, SEQ ID No: 18, SEQ ID No: 20, SEQ ID No: 22, or SEQ ID No: 24; or (ii) hybridizes, under stringency conditions including a hybridization medium which includes 0.9×SSC at a temperature of 42° C., to a DNA molecule complementary to SEQ ID No: 1, SEQ ID No: 3, SEQ ID No: 5, SEQ ID No: 7, SEQ ID No: 9, SEQ ID No: 11, SEQ ID No: 13, SEQ ID No: 15, SEQ ID No: 17, SEQ ID No: 19, SEQ ID No: 21, or SEQ ID No: 23; or (iii) includes a nucleotide sequence which is complementary to the nucleic acid molecules of (i) and (ii). Expression vectors, host cells, and transgenic plants which include the DNA molecules of the present invention are also disclosed. Methods of making such host cells and transgenic plant are disclosed.

A further aspect of the present invention relates to isolated effector proteins or polypeptides encoded by the nucleic acid molecules of the present invention. Compositions which contain the proteins or polypeptides are also disclosed.

Yet another aspect of the present invention relates to methods of imparting disease resistance to a plant. According to one approach, this method is carried out by transforming a plant cell with a heterologous DNA molecule of the present invention and regenerating a transgenic plant from the transformed plant cell, wherein the transgenic plant expresses the heterologous DNA molecule under conditions effective to impart disease resistance. According to one approach, this method is carried out by treating a plant with a protein or polypeptide of the present invention under conditions effective to impart disease resistance to the treated plant.

A further aspect of the present invention relates to a method of causing eukaryotic cell death which includes: introducing into a eukaryotic cell a cytotoxic *Pseudomonas* protein of the present invention, said introducing being performed under conditions effective to cause cell death.

A still further aspect of the present invention relates to a method of treating a cancerous condition which includes introducing a cytotoxic *Pseudomonas* protein of the present invention into cancer cells of a patient under conditions effective to cause death of cancer cells, thereby treating the cancerous condition.

Yet another aspect of the present invention relates to a method of modifying a metabolic pathway in a cell which includes: introducing into a cell a protein or polypeptide of the present invention which interacts with a native cellular protein involved in a metabolic pathway, wherein the protein or polypeptide modifies the metabolic pathway through its interaction with the native cellular protein.

It is believed that bacteria have evolved effector proteins to make exquisite alterations in host metabolism. While plant resistance and cancer cell toxicity are important uses, as mentioned above, it is believed that these effector proteins can be used to modify or effect metabolic targets in eukaryotes, including both yeasts and higher order species, such as plants and animals. It is noteworthy that several of the effector proteins being claimed in this application have homologs in other phytopathogenic bacteria. Thus, these proteins appear to represent a set of effectors that are conserved among *Pseudomonas, Erwinia, Xanthomonas*, and *Ralstonia* spp. By disrupting the function of these effectors through, for example, transgenic expression thereof in a host plant, it is believed that use of these effectors may lead to widely applicable means for controlling diseases of plants.

BRIEF DESCRIPTION OF THE DRAWINGS

In FIG. 2A, DC3000 or a DC3000 hrcC mutant (Yuan & He, *J. Bacteriol.* 178:6399–6402 (1996), which is hereby incorporated by reference in its entirety) carrying test ORFs (i.e., candidate effectors) fused to either the FLAG (F) or hemagglutinin (HA) epitopes were grown in Hrp-inducing media, and cultures were separated into cell (lanes 1–3) and supernatant (lanes 4–5) fractions and analyzed by SDS-PAGE and immunobloting. Lanes: 1 and 4, wild type DC3000; 2 and 5, wild type DC3000(pTestORF); 3 and 6, DC3000 hrcC mutant(pTestORF). As an additional control against leakage, pCPP2318 (which encodes the mature form of β-lactamase, β-lac) was included in all strains. The presence of an epitope-tagged protein in the supernatant fraction of the wild type (lane 5), but absence in the hrcC secretion mutant (lane 6), indicated that the test ORF encoded a secreted product. In FIG. 2B, AvrRpt2 translocation assays were performed with a DC3000 Avr-Rps4 homolog (now designated HopPtoK). Constructs that contained ORFs fused to AvrRpt2 lacking translocation signals were electroporated into *P. s. phaseolicola* 3121. Test strains were infiltrated into *A. thaliana* Col-0 (RPS2). Plant responses were scored 18 hr after inoculation for hypersensitive collapse (HR) or no visible response (N).

DETAILED DESCRIPTION OF THE INVENTION

Figure 1:
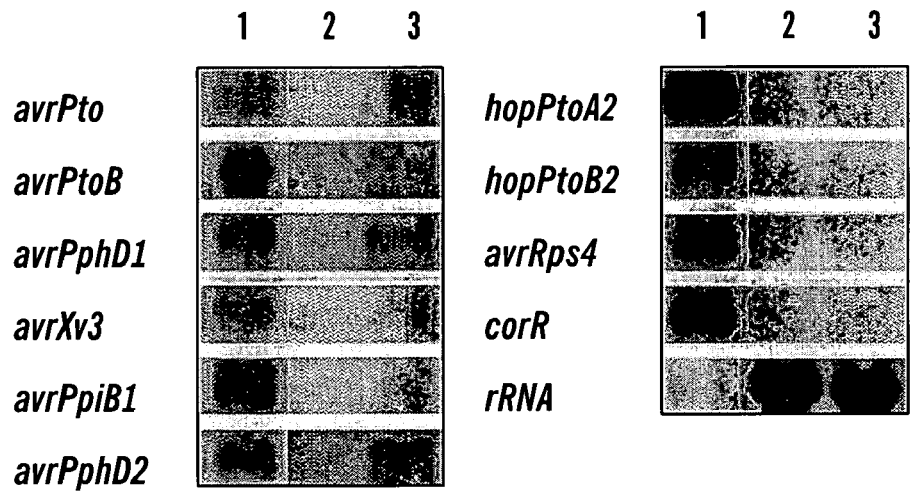
FIG. 1 is an RNA blot analysis of HrpL-dependent expression of representative virulence-implicated genes. Each well was loaded with 25 μg of total RNA isolated from CUCPB5114 cultures carrying either vector control pCPP5031 or $P_{nptII}$-hrpL plasmid pCPP5032 (lanes 2 and 3, respectively). PCR-amplified internal fragments were used as probes; lane 1 in each case contains PCR product of the corresponding probe. AvrPpiB1$_{Pto}$ and AvrPpiB2$_{Pto}$ are 100% identical, therefore their signals cannot be distinguished.

One aspect of the present invention relates to *Pseudomonas syringae* pv. *syringae* DC 3000 nucleic acid molecules which encode Avr or Hop effector proteins.

A first nucleic acid molecule is a homolog of avrPphE of *Pseudomonas syringae* pv. *phaseolicola* and has a nucleotide sequence according to SEQ ID No: 1 as follows:

```
atgaaaatac ataacgctgg cctaacccca cctttgccgg gcatttcgaa tggaaacgtt   60
ggaaaggcgg cgcaatcatc aataactcaa ccgcagagcc agcaaggctc ttatggcttg   120
ccaccagaaa gctctgagac tcgccctgat agggcgcgtg cgaactatcc atattcatca   180
gtacaaacac ggttgccgcc cgttgcgtct gctgggaaac cgctgcctga tacaccatct   240
tctttgcccg gctacttact gttgcgaagg ctggaccatc gccctgtgga tcaggaaggt   300
accaaaagtc tgatcccggc agacaaggct gtggctgaag cgcgccgtgc attgcccttt   360
ggaagaggca atattgatgt ggatgcgcaa ctttccaatc tggaaagtgg agcccgcacc   420
```

-continued

```
cttgcagcaa ggtgcttgag aaaagatgcc gaggccgccg gtcatgagcc tatgcctgcg   480
aatgagccga tgaactggca tgttcttgtt gcgatgtcag gccaggtgtt cggcgcgggc   540
aactgtggcg aacatgctcg tatagcgagc ttcgcctatg agctttggc ccaggaaaac    600
ggacgatctg aatatgaaaa catctacttg gctgcatcga ctgaggaaga tcatgtgtgg   660
gctgaaaccg acgaatccca gtctggcacc tcaacgattg tcatggatcc gtggtcaaat   720
ggttcagcca tatttgcgga ggacagtagg tttgcgaaaa atcgaaatgc tgtagagcgt   780
acggatacgt ttaatctttc aaccgcagcc gaagcgggca aaattacgcg tgagacagcc   840
gagaaggctt tgacgcaggt cacaacccga ttgcagaaac gcctggcgga tcagcaggag   900
caagtctcgc ccatcaaaag tggtcgctat cgaccagaaa aatcggtact tgatgatgca   960
tttgtccgca gagtgagcga caagttgacc tcccctgatt tgcggcgtgc actacaggta  1020
gatattgaag cggtcggagt cgcaatgtcg ctcggcacca agggcgtcaa ggacgctact  1080
cgacaagccc gacctttggt tgagcttgca gtgaaggtcg cctctcctca aggcttggcg  1140
agacgagatg tctga                                                   1155
```

The encoded protein, designated AvrPphE$_{Pto}$, has an amino acid sequence according to SEQ ID No: 2 as follows:

```
Met Lys Ile His Asn Ala Gly Leu Thr Pro Pro Leu Pro Gly Ile Ser
 1               5                  10                  15

Asn Gly Asn Val Gly Lys Ala Ala Gln Ser Ser Ile Thr Gln Pro Gln
            20                  25                  30

Ser Gln Gln Gly Ser Tyr Gly Leu Pro Pro Glu Ser Ser Glu Thr Arg
        35                  40                  45

Pro Asp Arg Ala Arg Ala Asn Tyr Pro Tyr Ser Ser Val Gln Thr Arg
    50                  55                  60

Leu Pro Pro Val Ala Ser Ala Gly Lys Pro Leu Pro Asp Thr Pro Ser
65                  70                  75                  80

Ser Leu Pro Gly Tyr Leu Leu Leu Arg Arg Leu Asp His Arg Pro Val
                85                  90                  95

Asp Gln Glu Gly Thr Lys Ser Leu Ile Pro Ala Asp Lys Ala Val Ala
            100                 105                 110

Glu Ala Arg Arg Ala Leu Pro Phe Gly Arg Gly Asn Ile Asp Val Asp
        115                 120                 125

Ala Gln Leu Ser Asn Leu Glu Ser Gly Ala Arg Thr Leu Ala Ala Arg
    130                 135                 140

Cys Leu Arg Lys Asp Ala Glu Ala Ala Gly His Glu Pro Met Pro Ala
145                 150                 155                 160

Asn Glu Pro Met Asn Trp His Val Leu Val Ala Met Ser Gly Gln Val
                165                 170                 175

Phe Gly Ala Gly Asn Cys Gly Glu His Ala Arg Ile Ala Ser Phe Ala
            180                 185                 190

Tyr Gly Ala Leu Ala Gln Glu Asn Gly Arg Ser Glu Tyr Glu Asn Ile
        195                 200                 205

Tyr Leu Ala Ala Ser Thr Glu Glu Asp His Val Trp Ala Glu Thr Asp
    210                 215                 220

Glu Ser Gln Ser Gly Thr Ser Thr Ile Val Met Asp Pro Trp Ser Asn
225                 230                 235                 240
```

```
Gly Ser Ala Ile Phe Ala Glu Asp Ser Arg Phe Ala Lys Asn Arg Asn
            245                 250                 255

Ala Val Glu Arg Thr Asp Thr Phe Asn Leu Ser Thr Ala Ala Glu Ala
        260                 265                 270

Gly Lys Ile Thr Arg Glu Thr Ala Glu Lys Ala Leu Thr Gln Val Thr
        275                 280                 285

Thr Arg Leu Gln Lys Arp Leu Ala Asp Gln Gln Glu Gln Val Ser Pro
    290                 295                 300

Ile Lys Ser Gly Arp Tyr Arg Pro Glu Lys Ser Val Leu Asp Asp Ala
305                 310                 315                 320

Phe Val Arg Arg Val Ser Asp Lys Leu Thr Ser Pro Asp Leu Arg Arg
                325                 330                 335

Ala Leu Gln Val Asp Ile Glu Ala Val Gly Val Ala Met Ser Leu Gly
            340                 345                 350

Thr Lys Gly Val Lys Asp Ala Thr Arg Gln Ala Arg Pro Leu Val Glu
        355                 360                 365

Leu Ala Val Lys Val Ala Ser Pro Gln Gly Leu Ala Arg Arg Asp Val
    370                 375                 380
```

AvrPphE$_{Pto}$ has been shown to be expressed by DC3000. It has been demonstrated that AvrPphE of *Pseudomonas syringae* pv. *phaseolicola* is recognized within plant cells and that this protein alone is required for hypersensitive response induction (Stevens et al., "Sequence variations in alleles of the avirulence gene avrPphE: R2 from *Pseudomonas syringae* pv. *phaseolicola* lead to loss of recognition of the AvrPphE protein within bean cells and a gain in cultivar-specific virulence," *Mol. Microbiol.* 29(1):165–177 (1998); Mansfield et al., "Characterization of avrPphE, a gene for cultivar-specific avirulence from *Pseudomonas syringae* pv. *phaseolicola* which is physically linked to hrpY, new hrp gene identified in the halo-blight bacterium," *Mol. Plant Microbe Interact.* 7(6):726–739 (1994), each of which is hereby incorporated by reference in its entirety). AvrPphE has been shown to be secreted by a type III secretion system and translocated into plants. AvrPphE matches the R2 resistance gene of *Phaseolus*.

A second nucleic acid molecule is a homolog of avrRps4 of *Pseudomonas syringae* pv. *pisi* and has a nucleotide sequence according to SEQ ID No: 3 as follows:

```
atgaatcgca tttcaaccag ctcagtaaat tccagcttca attacacggc ccctacggag   60
gaagcgcaaa accgcttcgc ctcagcgccc gacaattccc ctctagttgt caccacaaca  120
tctatcgccc aagcgtcgga agggctacaa aggccggggg caacgctaag catgcaggcc  180
cagcgactgc gccaattgat ggggagcccg tctgagcagt gccggaggga cacaatgtta  240
gctaaagctt ttgatgctca acgcctaaac attaacactc aagcaggctc ttccaacagc  300
ccacacttga acgctctcaa cacgctccaa caacgacact tcaaacctgc ggctggtggg  360
ctagaaatcc cagttacatc caactcctta ttgggcggtg gcaggcaagt ctatcaaatt  420
ggctcatcgt cacgcgagct aagccaccga ccgtcaatg atcaggaccg cgcgcccttc  480
agggcgcttg agcggctgca cgccgagttg tttagaggtg ggccgattga gtttgtgcct  540
agaggcagca acgtgttggc ctcaaacgtg agggatgtcg acatggacga gttcgatgtc  600
atcaactcta aagacggctg ccaaggcatt ggcaccactg gcctgggacc ctgcattgca  660
gtgtgtgcaa gaggcatgga tagagaaggg cttccggtgc tgggtgtcta tcaccacagt  720
ggtatcggct caccagagga taccatggct actcttgatc aagcgatgcg cgataaaggt  780
gctttgcaaa tcaaatactc cctggtaggc ggcatgatca tgcctaaaga ggaagaggct  840
ggcagctatg acgacgagca aagcttttttg gcattgaaag gcagttattc aatcgaaggg  900
gcgcgcttgc atgtatccga aggcgaagag gacgtgcata ccggcgagga caacagtgtc  960
aatgttctgc tgatgcctga ccgcgttctg tacggtcgcg acacgctcta ctgctga    1017
```

The encoded protein, originally designated AvrRps$_{Pto}$ and now renamed HopPtoK, has an amino acid sequence according to SEQ ID No: 4 as follows:

```
Met Asn Arg Ile Her Thr Ser Ser Val Asn Ser Ser Phe Asn Tyr Thr
 1               5                  10                  15

Ala Pro Thr Glu Glu Ala Gln Asn Arg Phe Ala Ser Ala Pro Asp Asn
            20                  25                  30

Ser Pro Leu Val Val Thr Thr Thr Ser Ile Ala Gln Ala Ser Glu Gly
        35                  40                  45

Leu Gln Arg Pro Gly Ala Thr Leu Ser Met Gln Ala Gln Arg Leu Arg
    50                  55                  60

Gln Leu Met Gly Ser Pro Ser Glu Gln Cys Arg Arg Asp Thr Met Leu
65                  70                  75                   80

Ala Lys Ala Phe Asp Ala Gln Arg Leu Asn Ile Asn Thr Gln Ala Gly
                85                  90                  95

Ser Ser Asn Ser Pro His Leu Asn Ala Leu Asn Thr Leu Gln Gln Arg
                100                 105                 110

His Phe Lys Pro Ala Ala Gly Gly Leu Glu Ile Pro Val Thr Ser Asn
            115                 120                 125

Ser Leu Leu Gly Gly Gly Arg Gln Val Tyr Gln Ile Gly Ser Per Ser
    130                 135                 140

Arg Glu Leu Ser His Arg Pro Val Asn Asp Gln Asp Arg Ala Pro Phe
145                 150                 155                 160

Arg Ala Leu Glu Arg Leu His Ala Glu Leu Phe Arg Gly Gly Pro Ile
                165                 170                 175

Glu Phe Val Pro Arg Gly Ser Asn Val Leu Ala Ser Asn Val Arg Asp
            180                 185                 190

Val Asp Met Asp Glu Phe Asp Val Ile Asn Ser Lys Asp Gly Cys Gln
            195                 200                 205

Gly Ile Gly Thr Thr Gly Leu Gly Pro Cys Ile Ala Val Cys Ala Arg
    210                 215                 220

Gly Met Asp Arg Glu Gly Leu Pro Val Leu Gly Val Tyr His His Ser
225                 230                 235                 240

Gly Ile Gly Ser Pro Glu Asp Thr Met Ala Thr Leu Asp Gln Ala Met
                245                 250                 255

Arg Asp Lys Gly Ala Leu Gln Ile Lys Tyr Ser Leu Val Gly Gly Met
            260                 265                 270

Ile Met Pro Lys Glu Glu Ala Gly Per Tyr Asp Asp Glu Gln Ser
            275                 280                 285

Phe Leu Ala Leu Lys Gly Ser Tyr Ser Ile Glu Gly Ala Arg Leu His
    290                 295                 300

Val Ser Glu Gly Glu Glu Asp Val His Thr Gly Glu Asp Asn Ser Val
305                 310                 315                 320

Asn Val Leu Leu Met Pro Asp Arg Val Leu Tyr Gly Arp Asp Thr Leu
                325                 330                 335

Tyr Cys
```

HopPtoK has been shown to be a secreted protein that is expressed by DC3000. The *Pseudomonas syringae* pv. *pisi* AvrRps4 effector matches the disease locus RPS4. It has previously been demonstrated that *Pseudomonas syringae* strains carrying avrRps4 induces a hypersensitive response on specific accessions of both Arabidopsis and soybean (Hinsch et al., "Identification of a new Arabidopsis disease resistance locus, RPs4, and cloning of the corresponding avirulence gene, avrRps4, from *Pseudomonas syringae* pv. *pisi*," *Mol. Plant Microbe Interact.* 9(1):55–61 (1996), which is hereby incorporated by reference in its entirety).

A third nucleic acid molecule is a homolog of avrPphF orf1 of *Pseudomonas syringae* pv. *phaseolicola* and has a nucleotide sequence according to SEQ ID No: 5 as follows:

```
atgaaaaacg catttgacct gcttgtggaa gggctggcta aggactacaa catgccgccc  60
ttgcctgaca agaaacatat cgatgaagtc tattgctttg agtttcaaag tggtatgaac 120
gtaaaagtat accaagacga atttcgctgg gtatatttca ccgctgacgt tgggacattt 180
caagatagca gtattgacac attaaactac gcgctccagc tgaacaactt tagccttaga 240
aaaccttttcc tgaccttcgg aatgacgaag gagaaaaatg gtgtattgca tacacgcacc 300
cccttgattg aggtagacaa cgtgcaaatg cgcaggatat ttgaggagct tataggcgtg 360
gcaggtgaaa tcagaaaaac actaaaactc aaatag                            396
```

The encoded protein has an amino acid sequence according to SEQ ID No: 6 as follows:

```
Met Lys Asn Ala Phe Asp Leu Leu Val Glu Gly Leu Ala Lys Asp Tyr
 1               5                  10                  15
Asn Met Pro Pro Leu Pro Asp Lys Lys His Ile Asp Glu Val Tyr Cys
            20                  25                  30
Phe Glu Phe Gln Ser Gly Met Asn Val Lys Val Tyr Gln Asp Glu Phe
        35                  40                  45
Arp Trp Val Tyr Phe Thr Ala Asp Val Gly Thr Phe Gln Asp Ser Ser
    50                  55                  60
Ile Asp Thr Leu Asn Tyr Ala Leu Gln Leu Asn Asn Phe Per Leu Arg
65                  70                  75                  80
Lys Pro Phe Leu Thr Phe Gly Met Thr Lys Glu Lys Asn Gly Val Leu
                85                  90                  95
His Thr Arg Thr Pro Leu Ile Glu Val Asp Asn Val Gln Met Arg Arp
            100                 105                 110
Ile Phe Glu Glu Leu Ile Gly Val Ala Gly Glu Ile Arg Lys Thr Leu
        115                 120                 125
Lys Leu Lys
        130
```

This protein is believed to be a chaperone protein for the protein of SEQ ID NO: 8 described below.

A fourth nucleic acid molecule is also homolog of avrPphF orf2 of *Pseudomonas syringae* pv. *phaseolicola* and has a nucleotide sequence according to SEQ ID No: 7 as follows:

```
gtgtatagcc catcccatac acaacgaata acttcagctc cctctacatc cactcatgtt  60
ggtggagata cactgacatc cattcatcag ctttcgcata gtcagagaga gcagtttctg 120
aacatgcatg atccaatgag agtaatggga cttgaccatg ataccgagct tttcagaacg 180
acgatagtc gctatataaa aaacgataaa ctcgcgggca atccacaatc catggcgagt 240
atccttatgc atgaagaact gcgccccaat cgttttgcca gccatacagg tgcccaacca 300
cacgaagcaa gggcgtacgt tccgaaaaga ataaaagcca ccgatctagg agttccatca 360
```

-continued

```
ctgaacgtaa tgactggctc gctagcgcga gacggaatta gagcttatga tcacatgagt   420
gataatcagg tctctgtcaa aatgcgactg ggagattttc tcgaaagggg tggcaaggtc   480
tatgccgacg cttcgtctgt agctgacgat ggggaaacat cacaagctct gattgtcaca   540
ttgcccaaag gacagaaagt gccggtcgaa agggtctga                          579
```

The encoded protein, designated AvrPphF$_{Pto}$, has an amino acid sequence according to SEQ ID No: 8 as follows:

```
Val Tyr Ser Pro Ser His Thr Gln Arg Ile Thr Ser Ala Pro Ser Thr
 1               5                  10                  15

Ser Thr His Val Gly Gly Asp Thr Lou Thr Ser Ile His Gln Leu Ser
            20                  25                  30

His Ser Gln Arg Glu Gln Phe Leu Asn Met His Asp Pro Met Arg Val
        35                  40                  45

Met Gly Leu Asp His Asp Thr Glu Leu Phe Arg Thr Thr Asp Ser Arg
    50                  55                  60

Tyr Ile Lys Asn Asp Lys Leu Ala Gly Asn Pro Gln Ser Met Ala Ser
65                  70                  75                  80

Ile Leu Met His Glu Glu Leu Arg Pro Asn Arg Phe Ala Ser His Thr
                85                  90                  95

Gly Ala Gln Pro His Glu Ala Arg Ala Tyr Val Pro Lys Arg Ile Lys
                100                 105                 110

Ala Thr Asp Leu Gly Val Pro Ser Leu Asn Val Met Thr Gly Ser Leu
            115                 120                 125

Ala Arg Asp Gly Ile Arg Ala Tyr Asp His Met Ser Asp Asn Gln Val
        130                 135                 140

Ser Val Lys Met Arg Leu Gly Asp Phe Leu Glu Arg Gly Gly Lys Val
145                 150                 155                 160

Tyr Ala Asp Ala Ser Ser Val Ala Asp Asp Gly Glu Thr Ser Gln Ala
                165                 170                 175

Leu Ile Val Thr Leu Pro Lys Gly Gln Lys Val Pro Val Glu Arg Val
            180                 185                 190
```

AvrPphF$_{Pto}$ has been shown to be expressed by DC3000. Fusion of both the homolog of AvrPphF orf1 and AvrPphF$_{Pto}$ with the AvrRpt2 reporter (AvrRpt2Δ40) caused a hypersensitive response in Arabidopsis Col-0, suggesting that AvrPphF$_{Pto}$ is secreted. Neither Orf1-AvrRpt2Δ40 (AvrPphF$_{Pto}$) nor Orf2-AvrRpt2Δ40 alone causes the hypersensitive response in Arabidopsis Col-0, although mutants of the homolog of AvrPphF orf1 have shown reduced disease symptoms on tomato. The *Pseudomonas syringae* pv. *phaseolicola* AvrPphF effector protein has been shown to play a role in both development of the hypersensitive response and virulence in several plants (Tsiamis et al., "Cultivar-specific avirulence and virulence functions assigned to avrPphF in *Pseudomonas syringae* pv. *phaseolicola*, the cause of bean halo-blight disease," *EMBO J.* 19(13):3204–3214 (2000), which is hereby incorporated by reference in its entirety).

A fifth nucleic acid molecule is a homolog of avrPphD of *Pseudomonas syringae* pv. *phaseolicola* and has a nucleotide sequence according to SEQ ID No: 9 as follows:

```
atgaatcctc tacgatctat tcaacacaac attgcaactc ccccaatcag tggcggtcag   60
ccattagacg cggtgggccc tcaggcccag caatcccatc ctaaaaggat ttcaccttct  120
caattgagcc aaagcgctca ccaggctcta gaacgccttt cagctaatgc cgaacaccaa  180
cgccttgcat cactggtacg caacgctctg caggatggca catttcaatt tcaatccagt  240
aaccacacgc aagtaaccta taaagcgtca atctgtctgc cagctgacac cgataccgtg  300
agaaccgacc acttgattaa taacgagctg acggttcagg cccgattaaa tgatcaatcg  360
```

```
                          -continued
gagtacgaca tcgtcagcgc acatttgcat ggctcttcga aagccatatc cttcgacgta  420
cccagccccc cgcccgcaca tggttcagca tcttctgtct tgagtgaacg gacccatcta  480
ggtatgagtc gcgttctctc acaagatgca gtagacagca gtagcctgga aactccgtta  540
ctgagctcgc cagaccattc tcgtccgcca tcacagccaa agcccgtgca tatcgggtcg  600
gtccgcaggg actctggtag ccttgtttcc gataacccgg tagtgcaggc cctgctatcg  660
tttgcgcagg ccgaccaggc atttccacca caggccgcga gcattgccgg ggtccagctg  720
gaaatgcggc cacgtcggga tattgagaaa gcacttgagg aattcaaagg cgccttcacg  780
gtggtgaagg cgcaactgat gtccggtgcc aactcgtcgg agcgtgtaga tgaggatgtc  840
aacgcagaca tccatatccc cttattgctc aaggccatcg agcgggggc tgcggcattt   900 ggtccaaacg catcaatcgg ccagaatagc gcgaaagcgt ttctcgcctc atgtgctccc  960
aagatcacgt ccaatgacga tgtcctctcc gagttcatca accagaaact caaggggac   1020 gacgatcttc aggttcgcct gggcgcacag gaattgttgc atgtagccac caagaaggaa  1080
ttccagctcg gcggtctagc cggcagcatc ggggtcagca gcatactcgg ctcggcatgg  1140
gagcttggcg cttctgagct gttgaaaaat gccatcttcg gcaaaaattt ctcaccgagc  1200
caatatgccc tgcaattggc tggaatcgat tcagtgcctc ctttgattat cgagtccatg  1260
gacaccatgt gcgtacttgc catcatcaag ggcatgaagg gtgaggagtg gtccatgagc  1320
gatctacttc ccaaggcgtt gaaggccggt gctatttcct cggtggtgtc attccccaat  1380
aatgttttgc agtatgcagg tttcaaatcc agagtcggcg atcttgcggc aaactcagtg  1440
acaactgaag cggccatctt tggcgccgcc tccggtattc cacccgaggt caaggaaagt  1500
gaagagctga tgcgtgctgg cttattccag agcatgaagg acggcgtgat ggctcattca  1560
ggcgaggggg tggacaccaa aaaacgatt gagcggatga cgcgccatgc gctggatatc   1620
gctccgggcg aaagcaccgc tgtcaagtcc atggggctgg catcgattgt cgggatgatt  1680
ccactgattg ccagcaacaa ggcaaccggg ctgctgtcgg aacaggtact gcgtatttc   1740 cggagcgccg tcttcaatcc aatcgaagcc atcgctctga acgcgttggc gcttggcggg  1800
cgtgtcaacg ttcccgggct atttgattcc gacaatgcca agcatgcacg cgtggtacaa  1860
accatccttg cgcgggccag ccagcacatg gaagctggag accgtgacat tccgcagag   1920 gagctacatc aaatgctggc tccccggagc gagttcctgc gccatgtggg atctgcgatt  1980
gtcaacggca tgaatgccag cttttgaggca attcccgccc tggttcggaa gcttggatat  2040
ggtgaggctc cattggccga acgtattccg tatcaagacc tggctgtgcc cgacacgtcg  2100
cggcagcccg cacccctga                                               2118
```

The encoded protein, originally designated AvrPphD1$_{Pto}$ and now renamed HopPtoD1, has an amino acid sequence according to SEQ ID No: 10 as follows:

```
Met Asn Pro Leu Arg Her Ile Gln His Asn Ile Ala Thr Pro Pro Ile
 1               5                  10                  15

Ser Gly Gly Gln Pro Leu Asp Ala Val Gly Pro Gln Ala Gln Gln Her
             20                  25                  30

His Pro Lys Arg Ile Ser Pro Ser Gln Leu Ser Gln Ser Ala His Gln
         35                  40                  45

Ala Leu Glu Arg Leu Ser Ala Asn Ala Glu His Gln Ary Leu Ala Ser
     50                  55                  60
```

-continued

```
Leu Val Arg Asn Ala Leu Gln Asp Gly Thr Phe Gln Phe Gln Ser Ser
 65                  70                  75                  80

Asn His Thr Gln Val Thr Tyr Lys Ala Ser Ile Cys Leu Pro Ala Asp
                 85                  90                  95

Thr Asp Thr Val Arg Thr Asp His Leu Ile Asn Asn Glu Leu Thr Val
            100                 105                 110

Gln Ala Arg Leu Asn Asp Gln Ser Glu Tyr Asp Ile Val Ser Ala His
        115                 120                 125

Leu His Gly Ser Ser Lys Ala Ile Ser Phe Asp Val Pro Ser Pro Pro
    130                 135                 140

Pro Ala His Gly Ser Ala Ser Ser Val Leu Ser Glu Arg Thr His Leu
145                 150                 155                 160

Gly Met Ser Arg Val Leu Ser Gln Asp Ala Val Asp Ser Ser Ser Leu
                165                 170                 175

Glu Thr Pro Leu Leu Ser Ser Pro Asp His Ser Arg Pro Pro Ser Gln
            180                 185                 190

Pro Lys Pro Val His Ile Gly Ser Val Arg Arg Asp Ser Gly Ser Leu
        195                 200                 205

Val Ser Asp Asn Pro Val Val Gln Ala Leu Leu Ser Phe Ala Gln Ala
    210                 215                 220

Asp Gln Ala Phe Pro Pro Gln Ala Ala Ser Ile Ala Gly Val Gln Leu
225                 230                 235                 240

Glu Met Arg Pro Arg Arg Asp Ile Glu Lys Ala Leu Glu Glu Phe Lys
                245                 250                 255

Gly Ala Phe Thr Val Val Lys Ala Gln Leu Met Ser Gly Ala Asn Ser
            260                 265                 270

Ser Glu Arg Val Asp Glu Asp Val Asn Ala Asp Ile His Ile Pro Leu
        275                 280                 285

Leu Leu Lys Ala Ile Glu Arg Gly Ala Ala Phe Gly Pro Asn Ala
    290                 295                 300

Ser Ile Gly Gln Asn Ser Ala Lys Ala Phe Leu Ala Ser Cys Ala Pro
305                 310                 315                 320

Lys Ile Thr Ser Asn Asp Val Leu Ser Glu Phe Ile Asn Gln Lys
                325                 330                 335

Leu Lys Gly Asp Asp Asp Leu Gln Val Arg Leu Gly Ala Gln Glu Leu
            340                 345                 350

Leu His Val Ala Thr Lys Lys Glu Phe Gln Leu Gly Leu Ala Gly
        355                 360                 365

Ser Ile Gly Val Ser Ser Ile Leu Gly Ser Ala Trp Glu Leu Gly Ala
    370                 375                 380

Ser Glu Leu Leu Lys Asn Ala Ile Phe Gly Lys Asn Phe Ser Pro Ser
385                 390                 395                 400

Gln Tyr Ala Leu Gln Leu Ala Gly Ile Asp Ser Val Pro Pro Leu Ile
                405                 410                 415

Ile Glu Ser Met Asp Thr Met Cys Val Leu Ala Ile Lys Gly Met
            420                 425                 430

Lys Gly Glu Glu Trp Ser Met Ser Asp Leu Leu Pro Lys Ala Leu Lys
        435                 440                 445

Ala Gly Ala Ile Ser Ser Val Val Ser Phe Pro Asn Asn Val Leu Gln
    450                 455                 460

Tyr Ala Gly Phe Lys Ser Arg Val Gly Asp Leu Ala Ala Asn Ser Val
465                 470                 475                 480

Thr Thr Glu Ala Ala Ile Phe Gly Ala Ala Ser Gly Ile Pro Pro Glu
                485                 490                 495
```

-continued

```
Val Lys Glu Ser Glu Leu Met Arg Ala Gly Leu Phe Gln Ser Met
            500             505             510

Lys Asp Gly Val Met Ala His Ser Gly Glu Gly Val Asp Thr Lys Lys
            515             520             525

Thr Ile Glu Arg Met Thr Arg His Ala Leu Asp Ile Ala Pro Gly Glu
        530             535             540

Ser Thr Ala Val Lys Ser Met Gly Leu Ala Ser Ile Val Gly Met Ile
545             550             555             560

Pro Leu Ile Ala Ser Asn Lys Ala Thr Gly Leu Leu Ser Glu Gln Val
                565             570             575

Leu Arg Ile Phe Arg Ser Ala Val Phe Asn Pro Ile Glu Ala Ile Ala
            580             585             590

Leu Asn Ala Leu Ala Leu Gly Gly Arg Val Asn Val Pro Gly Leu Phe
            595             600             605

Asp Ser Asp Asn Ala Lys His Ala Arg Val Val Gln Thr Ile Leu Ala
            610             615             620

Arg Ala Ser Gln His Met Glu Ala Gly Asp Arg Asp Ile Ser Ala Glu
625             630             635             640

Glu Leu His Gln Met Leu Ala Pro Arg Ser Glu Phe Leu Arg His Val
            645             650             655

Gly Ser Ala Ile Val Asn Gly Met Asn Ala Ser Phe Glu Ala Ile Pro
            660             665             670

Ala Leu Val Arg Lys Leu Gly Tyr Gly Glu Ala Pro Leu Ala Glu Arg
            675             680             685

Ile Pro Tyr Gln Asp Leu Ala Val Pro Asp Thr Ser Arg Gln Pro Ala
            690             695             700

Pro
705
```

HopPtoD1 has been shown to be a secreted protein that is expressed by DC3000.

A sixth nucleic acid molecule is another homolog of avrPphD of *Pseudomonas syringae* pv. *phaseolicola* and has a nucleotide sequence according to SEQ ID No: 11 as follows:

```
atgaatcccc tgcaacctat tcagcacagc attacaaatt cccaaatgag tggtggtcag  60
caattagagg cggagggctc tcaggcccac aattcctatt cccatcctga caggatttcg  120
ctttcccaat tgagccaaag cgctcaccta gctctagatc acctttcaac tcagcctaat  180
accgatcacc aacgcgttgc atcactggta cgcaacgctg tgcaggacgg taagttccaa  240
cttcaatcca gtaacgacac gcaagtaacc tataaaactt cagtctgtcc gccagctaac  300
gccgacacca tgggggccgc ccacttaatt aataacgagc tgacggttca ggcccgatta  360
aatgatcaac ttgagtacga catcgtcagc gctcatttgt atggcccttc ggaagccata  420
tccatcgatg catccagtcc tccctcggcc aacgatctag cgtcctctgg cttgagcgaa  480
cgtacgcacc taggtatgaa tcgtgtcctc ttacgctacg cggtgccccc tcgggaaacc  540
gaagaccaat gtgttatggt gatcgacaaa atgccccccc ccaaacacgg caaaatgtct  600
ttcttccgta ccactaatga cttgagcaaa ctgcctttgg gaatggagac gggcgggttg  660
tccgacctga aattggctgg ttgtgaacgt atttcttccg tcgagcaggt gaagagtatc  720
cgcgcagcgc ttggaggcgg gccgctcacc gtactagatc tgcgcgaaga atctcatgcg  780
```

```
attgtcaacg gtttgcctat caccttacgt ggcccgatgg attgggccaa cgccggccta   840
tcccaggttg acggagcggc acgtgaaagt gccatgatta cagaactgaa gcgcactaag   900
tctttaacgt tggtcgatgc caattatgta aaaggtaaaa aaagtaatcc tcaaacgaca   960
gaactgaaaa atttgaatgt ccggagcgag cgagaagtcg ttacagaggc cggcgcgacc  1020
tatcgccgcg tggccattac cgaccataac aggcctagtc cggaagcgac cgacgagcta  1080
gtagacatca tgcgccactg cctgcaggca aatgagtcgc tagttgtgca ctgtaacggc  1140
ggtcggggcc gtactaccac ggctatgata atggtcgaca tgcttaagaa cgctcgtaac  1200
cattccgcag aaaccctcat cacgcgtatg gccaagctaa gctatgacta caacatgacg  1260
gatctaggca gcatttctgc actcaagcgg ccattcctag aggacagact aaaatttctg  1320 caggccttc acgactatgc ccgcaacaac ccaagcggat tatctcttaa ttggacacag  1380
tggcgcgcaa aaatagcgtt agaatga                                     1407
```

The encoded protein, originally designated AvrPphD2$_{Pto}$ and now renamed HopPtoD2, has an amino acid sequence according to SEQ ID No: 12 as follows:

```
Met Asn Pro Leu Gln Pro Ile Gln His Ser Ile Thr Asn Ser Gln Met
  1               5                  10                  15

Ser Gly Gly Gln Gln Leu Glu Ala Glu Gly Ser Gln Ala His Asn Ser
             20                  25                  30

Tyr Her His Pro Asp Arg Ile Ser Leu Ser Gln Leu Ser Gln Ser Ala
             35                  40                  45

His Leu Ala Leu Asp His Leu Her Thr Gln Pro Asn Thr Asp His Gln
  50                  55                  60

Arg Val Ala Ser Leu Val Arg Asn Ala Val Gln Asp Gly Lys Phe Gln
 65                  70                  75                  80

Leu Gln Ser Ser Asn Asp Thr Gln Val Thr Tyr Lys Thr Ser Val Cys
                 85                  90                  95

Pro Pro Ala Asn Ala Asp Thr Met Gly Ala Ala His Leu Ile Asn Asn
                100                 105                 110

Glu Leu Thr Val Gln Ala Arg Leu Asn Asp Gln Leu Glu Tyr Asp Ile
            115                 120                 125

Val Ser Ala His Leu Tyr Gly Pro Ser Glu Ala Ile Ser Ile Asp Ala
            130                 135                 140

Ser Ser Pro Pro Ser Ala Asn Asp Leu Ala Ser Ser Gly Len Ser Glu
145                 150                 155                 160

Arg Thr His Leu Gly Met Asn Arg Val Leu Leu Arg Tyr Ala Val Pro
                165                 170                 175

Pro Arg Glu Thr Glu Asp Gln Cys Val Met Val Ile Asp Lys Met Pro
            180                 185                 190

Pro Pro Lys His Gly Lys Met Ser Phe Phe Arg Thr Thr Asn Asp Leu
            195                 200                 205

Ser Lys Leu Pro Leu Gly Met Glu Thr Gly Gly Leu Ser Asp Leu Lys
            210                 215                 220

Leu Ala Gly Cys Glu Arg Ile Ser Ser Val Glu Gln Val Lys Ser Ile
225                 230                 235                 240

Arg Ala Ala Leu Gly Gly Gly Pro Leu Thr Val Leu Asp Leu Arg Glu
                245                 250                 255
```

```
        Glu Ser His Ala Ile Val Asn Gly Leu Pro Ile Thr Leu Arg Gly Pro
                    260                 265                 270

Met Asp Trp Ala Asn Ala Gly Leu Ser Gln Val Asp Gly Ala Ala Arg
                    275                 280                 285

Glu Ser Ala Met Ile Thr Glu Leu Lys Arg Thr Lys Ser Leu Thr Leu
                    290                 295                 300

Val Asp Ala Asn Tyr Val Lys Gly Lys Lys Ser Asn Pro Gln Thr Thr
        305                 310                 315                 320

Glu Leu Lys Asn Leu Asn Val Arg Ser Glu Arg Glu Val Val Thr Glu
                        325                 330                 335

Ala Gly Ala Thr Tyr Arg Arg Val Ala Ile Thr Asp His Asn Arg Pro
                    340                 345                 350

Ser Pro Glu Ala Thr Asp Glu Leu Val Asp Ile Met Arg His Cys Leu
                    355                 360                 365

Gln Ala Asn Glu Ser Leu Val Val His Cys Asn Gly Arg Gly Arg
                    370                 375                 380

Thr Thr Thr Ala Met Ile Met Val Asp Met Leu Lys Asn Ala Arg Asn
        385                 390                 395                 400

His Ser Ala Glu Thr Leu Ile Thr Arg Met Ala Lys Leu Ser Tyr Asp
                        405                 410                 415

Tyr Asn Met Thr Asp Leu Gly Ser Ile Ser Ala Leu Lys Arg Pro Phe
                    420                 425                 430

Leu Glu Asp Arg Leu Lys Phe Leu Gln Ala Phe His Asp Tyr Ala Arg
                    435                 440                 445

Asn Asn Pro Ser Gly Leu Ser Leu Asn Trp Thr Gln Trp Arg Ala Lys
                    450                 455                 460

Ile Ala Leu Glu
        465
```

HopPtoD2 has been shown to be a secreted protein that is expressed by DC3000.

A seventh nucleic acid molecule is a homolog of avrP-piC2 of *Pseudomonas syringae* pv. *pisi* and has a nucleotide sequence according to SEQ ID No: 13 as follows:

```
atgacaatcg tgtctggaca catcggaaaa cacccaagcc taaccactgt tcaagctggg   60
tcttcggctt cggtcgagaa tcaaatgcct gatcctgcac agttcagtga tggacggtgg  120
aaaaagcttc cgacccaatt gtcgtcaatt acattggcga gattcgatca ggatatttgc  180
acgaataatc atggcatcag tcagcgtgca atgtgctttg gcctttcatt gagctggatt  240
aacatgattc atgccgggaa agatcatgtt acgccctatg catcggcaga agaatgagg   300 tttctgggtt cctttgaagg ggtggtgcat gctcgtactg ttcataactt ctatcggact  360
gagcacaaat ttctgatgga gcaagcttcc gcaaaccccg gagtatcaag tggcgcgatg  420
gctggcacag aaagtttatt gcaagctgct gagttgaagg ggttaaagct tcaacctgtt  480
ctagaggaca agtcgaactc aggcctaccc ttcctaattg cgtgtaagca gtcagggcgg  540
caggtgagca cagatgaagc tgcgctaagc tccttatgtg atgcaattgt agaaaataag  600
agaggggtaa tggtgatata cagccaagaa attgcccacg ctttgggctt ttctgtatca  660
tcagatggca aaagagcgac cttatttgat cccaatctcg gagagtttca tacacactcg  720
aaagcgttgg ctgatactat cgaaaacata tcatcggcag atgggctgcc tttaatcggc  780
gttcaagtat tcgcttcaaa aatacactga                                   810
```

The encoded protein, originally designated AvrPpiC2$_{Pto}$ and now renamed HopPtoC, has an amino acid sequence according to SEQ ID No: 14 as follows:

```
Met Thr Ile Val Ser Gly His Ile Gly Lys His Pro Ser Leu Thr Thr
 1               5                  10                  15
Val Gln Ala Gly Ser Ser Ala Ser Val Glu Asn Gln Met Pro Asp Pro
                20                  25                  30
Ala Gln Phe Ser Asp Gly Arg Trp Lys Lys Leu Pro Thr Gln Leu Ser
            35                  40                  45
Ser Ile Thr Leu Ala Arg Phe Asp Gln Asp Ile Cys Thr Asn Asn His
        50                  55                  60
Gly Ile Ser Gln Arg Ala Met Cys Phe Gly Leu Ser Leu Ser Trp Ile
65                  70                  75                  80
Asn Met Ile His Ala Gly Lys Asp His Val Thr Pro Tyr Ala Ser Ala
                85                  90                  95
Glu Arg Met Arg Phe Leu Gly Ser Phe Glu Gly Val Val His Ala Arg
            100                 105                 110
Thr Val His Asn Phe Tyr Arg Thr Glu His Lys Phe Leu Met Glu Gln
        115                 120                 125
Ala Ser Ala Asn Pro Gly Val Ser Ser Gly Ala Met Ala Gly Thr Glu
    130                 135                 140
Ser Leu Leu Gln Ala Ala Glu Leu Lys Gly Leu Lys Leu Gln Pro Val
145                 150                 155                 160
Leu Glu Asp Lys Ser Asn Ser Gly Leu Pro Phe Leu Ile Ala Cys Lys
                165                 170                 175
Gln Ser Gly Arg Gln Val Ser Thr Asp Glu Ala Ala Leu Ser Ser Leu
            180                 185                 190
Cys Asp Ala Ile Val Glu Asn Lys Arg Gly Val Met Val Ile Tyr Ser
        195                 200                 205
Gln Glu Ile Ala His Ala Leu Gly Phe Ser Val Ser Ser Asp Gly Lys
    210                 215                 220
Arg Ala Thr Leu Phe Asp Pro Asn Leu Gly Glu Phe His Thr His Ser
225                 230                 235                 240
Lys Ala Leu Ala Asp Thr Ile Glu Asn Ile Ser Ser Ala Asp Gly Leu
                245                 250                 255
Pro Leu Ile Gly Val Gln Val Phe Ala Ser Lys Ile His
            260                 265
```

HopPtoC has been shown to be a secreted protein that is expressed by DC3000.

An eighth nucleic acid molecule is a homolog of avrP-piB1 of *Pseudomonas syringae* pv. *pisi* and has a nucleotide sequence according to SEQ ID No: 15 as follows:

```
atgcacgcaa atcctttaag ctctttcaac agagctcaac atggcaatct gactaatgta   60
gaggccagcc aagttaaatc ggcaggaacc tcttccacca ctaatataga cagtaaaaac  120
attgaagaac atgttgcaga cagactcagt gatttaggca gacctgatgg tggatggttt  180
ttcgagaagt cacttggcac cttgaaaaat ttaaatcttg agcagttagc cggaatccat  240
gatgtactaa aattaacaga tggcgtaaag aacattgtct cttttggagc tcgggaagga  300
ggcttcgagt tggcaatgca gtttcgtcat gatttataca gatctcaaca tccggatgaa  360
aactcgccgc acgatgccgc aactcattat cttgatgcaa tcagcctgca atcaaacaaa  420
```

-continued

```
tttacaaaac ttgaaaaact acaacatgta gatgtattta aaatgcaaaa cccgttttgg    480
gatgtcgggt acaaaaacgg aattgcgcac gcaaaaaaaa tggcattctt cataacgcca    540
gagtggctgg gttctgattt ctgtaaacag gaattccagt ggcttagcga aacaaaaaac    600
aaagacataa aatctgcatt tgtgatcttt aaagatgtag acttaaaaag caaaaatatg    660
acaagtatct tcaattttgc agacttccat aaatcacgcg tcatgatggc aagcacacct    720
cccgaatcgg gattgaataa tgtaaaaatc gaaaatagcg ttgacctgaa tttcaagagg    780
ttattaactg accgtgagtc atgggaacta aataatttcc taggcgacta a             831
```

The encoded protein, designated AvrPpiB1$_{Pto}$, has an amino acid sequence according to SEQ ID No: 16 as follows:

```
Met His Ala Asn Pro Leu Ser Ser Phe Asn Arg Ala Gln His Gly Asn
 1               5                  10                  15

Leu Thr Asn Val Glu Ala Ser Gln Val Lys Ser Ala Gly Thr Ser Ser
                20                  25                  30

Thr Thr Asn Ile Asp Ser Lys Asn Ile Glu Glu His Val Ala Asp Arg
            35                  40                  45

Leu Ser Asp Leu Gly Arg Pro Asp Gly Gly Trp Phe Glu Lys Ser
    50                  55                  60

Leu Gly Thr Leu Lys Asn Leu Asn Leu Glu Gln Leu Ala Gly Ile His
65                  70                  75                  80

Asp Val Leu Lys Leu Thr Asp Gly Val Lys Asn Ile Val Ser Phe Gly
                85                  90                  95

Ala Arg Glu Gly Gly Phe Glu Leu Ala Met Gln Phe Arg His Asp Leu
                100                 105                 110

Tyr Arg Ser Gln His Pro Asp Glu Asn Ser Pro His Asp Ala Ala Thr
            115                 120                 125

His Tyr Leu Asp Ala Ile Ser Leu Gln Ser Asn Lys Phe Thr Lys Leiu
        130                 135                 140

Glu Lys Leu Gln His Val Asp Val Phe Lys Met Gln Asn Pro Phe Trp
145                 150                 155                 160

Asp Val Gly Tyr Lys Asn Gly Ile Ala His Ala Lys Lys Met Ala Phe
                165                 170                 175

Phe Ile Thr Pro Glu Trp Leu Gly Ser Asp Phe Cys Lys Gln Glu Phe
            180                 185                 190

Gln Trp Leu Ser Glu Thr Lys Asn Lys Asp Ile Lys Ser Ala Phe Val
        195                 200                 205

Ile Phe Lys Asp Val Asp Leu Lys Ser Lys Asn Met Thr Ser Ile Phe
    210                 215                 220

Asn Phe Ala Asp Phe His Lys Ser Arg Val Met Met Ala Ser Thr Pro
225                 230                 235                 240

Pro Glu Ser Gly Leu Asn Asn Val Lys Ile Glu Asn Ser Val Asp Leu
                245                 250                 255

Asn Phe Lys Arg Leu Leu Thr Asp Arg Glu Ser Trp Glu Leu Asn Asn
            260                 265                 270

Phe Leu Gly Asp
        275
```

AvrPpiB1$_{Pto}$ has been shown to be expressed by DC3000. A second copy of AvrPpiB1$_{Pto}$ is present in the genome of DC3000. This second copy is identical and has been designated AvrPpiB2$_{Pto}$. The *Pseudomonas syringae* pv. *pisi* AvrPpiB effector protein was demonstrated to effect the expression of a resistance mechanism governed by the R3 resistance locus of pea (Cournoyer et al., "Molecular characterization of the *Pseudomonas syringae* pv. *pisi* plasmid-borne avirulence gene avrPpiB which matches the R3 resistance locus in pea," *Mol. Plant Microbe Interact.* 8(5): 700–708 (1995), which is hereby incorporated by reference in its entirety).

A ninth nucleic acid molecule is a homolog of avrXv3 of *Xanthomonas campestris* pv. *vesicatoria* and has a nucleotide sequence according to SEQ ID No: 17 as follows:

```
atgggctat gtatttcaaa acactctggt agcagttaca gctacagtga tagcgaccgc  60
tggcaagtgc ctgcatgccc tccaaacgcc aggtctgtat ccagtcatca aacagcatct 120
gcgagtgaca tcgcatcagg cgatgtggat gaacgtcctg caacgttttc tcattttcaa 180
cttgcgcggt gcggtggaga gtacacgctt agcatggttt ctgcagcggc ttatcaagca 240
gaaagacggc atcgcggtaa tttaataaaa gatcgtagtc aatccatact cccatgggtc 300
caggtatatc attctaaaaa aggtttggat tacagcttcc agatcgacag aactacgact 360
gttaaagtgg ctggattcaa ctgctctatc cccaataaca gagggactcg gcatttatac 420
agcgctggta cgagtcagac aaacatgcct gtcatcgcag acaacatgag cgcatgcatt 480
gctgtcgcgt gtgcggcgga aaacgtggat gctggcacgg gtgaacgtag gccggggcg 540
aaagttcgcg tattccatct actcccttttt cgacgcgaag accttgtgcc agaagaagtt 600
ttagcttctg tgcgcgatta tctgcgaacg accaaagaac agggctaac aatgcgcgta 660
gctatgcatg gagggaatac agagggtgat ttctcagtca gcactgcgca ggcattgaaa 720
ggcctgtttg ctaatgaagg gatcccgctt gaatttgacg agacctgtgc aaaccgaacg 780
tctgaaacac tgcttggtgc cgttatctta gatgacaact cgactcattt cataaaacat 840
ctggtcgcac aataa                                                 855
```

The encoded protein, originally designated AvrXv3$_{Pto}$ and now renamed HopPtoJ, has an amino acid sequence according to SEQ ID No: 18 as follows:

```
Met Gly Leu Cys Ile Ser Lys His Ser Gly Ser Ser Tyr Ser Tyr Ser
1               5                   10                  15

Asp Ser Asp Arg Trp Gln Val Pro Ala Cys Pro Pro Asn Ala Arg Ser
            20                  25                  30

Val Ser Ser His Gln Thr Ala Ser Ala Ser Asp Ile Ala Ser Gly Asp
        35                  40                  45

Val Asp Glu Arg Pro Ala Thr Phe Ser His Phe Gln Leu Ala Arg Cys
    50                  55                  60

Gly Gly Glu Tyr Thr Leu Ser Met Val Ser Ala Ala Tyr Gln Ala
65                  70                  75                  80

Glu Arg Arg His Arg Gly Asn Leu Ile Lys Asp Arg Ser Gln Ser Ile
                85                  90                  95

Leu Pro Trp Val Gln Val Tyr His Ser Lys Lys Gly Leu Asp Tyr Ser
            100                 105                 110

Phe Gln Ile Asp Arg Thr Thr Val Lys Val Ala Gly Phe Asn Cys
        115                 120                 125

Ser Ile Pro Asn Asn Arg Gly Thr Arg His Leu Tyr Ser Ala Gly Thr
    130                 135                 140

Ser Gln Thr Asn Met Pro Val Ile Ala Asp Asn Met Ser Ala Cys Ile
145                 150                 155                 160
```

```
Ala Val Ala Cys Ala Ala Glu Asn Val Asp Ala Gly Thr Gly Glu Arg
            165                 170                 175

Arg Pro Gly Ala Lys Val Arg Val Phe His Leu Leu Pro Phe Arg Arg
            180                 185                 190

Glu Asp Leu Val Pro Glu Val Leu Ala Ser Val Arg Asp Tyr Leu
            195                 200                 205

Arg Thr Thr Lys Glu Gln Gly Leu Thr Met Arg Val Ala Met His Gly
            210                 215                 220

Gly Asn Thr Glu Gly Asp Phe Ser Val Ser Thr Ala Gln Ala Leu Lys
225                 230                 235                 240

Gly Leu Phe Ala Asn Glu Gly Ile Pro Leu Glu Phe Asp Glu Thr Cys
            245                 250                 255

Ala Asn Arg Thr Ser Glu Thr Leu Leu Gly Ala Val Ile Leu Asp Asp
            260                 265                 270

Asn Ser Thr His Phe Ile Lys His Leu Val Ala Gln
            275                 280
```

HopPtoJ has been shown to be a secreted protein that is expressed by DC3000. As reported in Astua-Monge et al. ("Resistance of tomato and pepper to T3 strains of *Xanthomonas campestris* pv. *vesicatoria* is specified by a plant-inducible avirulence gene," *Mol. Plant Microbe Interact.* 13:911–921 (2000), which is hereby incorporated by reference in its entirety), it has been demonstrated that the *Xanthomonas campestris* AvrXv3 effector protein elicits a hypersensitive response in tomato NIL 216 and certain pepper genotypes, which suggests that AvrXv3 is like other effectors in functioning inside plant cells. A uidA fusion enabled demonstration that the avrXv3 gene is part of the Hrp regulon. A domain in the C terminus of AvrXv3 is possibly responsible for transcriptional activation activity in yeast. For these reasons, it is also believed that HopPtoJ possesses similar characteristics and properties.

A tenth nucleic acid molecule is a homolog of hrmB of *Pseudomonas syringae* pv. *syringae* and has a nucleotide sequence according to SEQ ID No: 19 as follows:

```
atgatcatcg acaatacgtt cgcgctgaca ctgtcatgcg attacgcgcg tgagcgcctg   60
ctgttgatcg gcttgcttga gccgcacaag gacatacctc agcagtgcct tttggctggc  120
gctctcaatc cgctcctcaa tgcaggccca ggccttggcc tggatgagaa aagcggcctg  180
tatcacgcgt atcaaagcat ccctcgagaa aaactcagcg tgccgacgct caaacgcgaa  240
atggcaggtc tgctggagtg gatgaggggc tggcgcgaag caagccaata g           291
```

The encoded protein, believed to be a chaperone for the protein of SEQ ID No: 22, has an amino acid sequence according to SEQ ID No: 20 as follows:

```
Met Ile Ile Asp Asn Thr Phe Ala Leu Thr Leu Ser Cys Asp Tyr Ala
1                   5                   10                  15

Arg Glu Arg Leu Leu Leu Ile Gly Leu Leu Glu Pro His Lys Asp Ile
            20                  25                  30

Pro Gln Gln Cys Leu Leu Ala Gly Ala Leu Asn Pro Leu Leu Asn Ala
            35                  40                  45

Gly Pro Gly Leu Gly Leu Asp Glu Lys Her Gly Leu Tyr His Ala Tyr
            50                  55                  60

Gln Ser Ile Pro Arg Glu Lys Leu Ser Val Pro Thr Leu Lys Arg Glu
            65                  70                  75                  80

Met Ala Gly Leu Leu Glu Trp Met Arg Gly Trp Arg Glu Ala Ser Gln
            85                  90                  95
```

An eleventh nucleic acid molecule is a homolog of hrmA (also known as hopPsyA) of *Pseudomonas syringae* pv. *syringae* and has a nucleotide sequence according to SEQ ID No: 21 as follows:

```
atgaacccca ttcagtcacg cttctccagt gtgcaagagc tcagacgatc caacgttgat  60
attccggcgc tcaaagccaa tggccaactg gaggtcgacg gcaagaggta cgagattcgt  120
gcagccgatg acggaacaat ttcggtcctt cgaccggagc aacaatccaa agcgaaaagt  180
tttttcaagg gcgcttccca gttgataggt ggcagcagcc agcgcgcgca gattgcccag  240
gcgctcaacg agaaggtcgc atcggcacgc actgtcttgc accagagcgc tatgacgggc  300
ggacgcttgg acacccttga gcggggcgaa agcagctcag ccacaacagc catcaaaccc  360
actgccaaac aggctgcgca aagtactttt aacagctttc atgagtgggc caaacaggca  420
gaggcgatgc gaaacccgtc tcgaatggat atctacaaga tctataaaca agatgcacct  480
cactcacacc ccatgagcga cgagcagcaa gaagagttcc tgcacacgct aaaggcattg  540
aatggcaaaa acggcattga ggtgcgcact caggaccacg acagcgtcag aaataaaaaa  600
gaccgcaacc tggacaagta catcgcagag agcccggatg caaagaggtt tttctatcga  660
attatcccca aacatgagcg ccgagaagat aagaatcaag ggcgattgac cattggcgtg  720
caaccccaat atgcaacaca gttgacccgc gccatggcaa ccctgatagg gaaggaaagt  780
gcaatcacgc atggcaaagt aataggcccc gcctgccacg gccaaatgac cgattcggca  840
gttttgtata tcaacggtga tgttgcaaag gcagaaaagc tgggcgagaa actgaaacag  900
atgagcggca ttcctctgga tgcgttcgtt gagcacaccc ctttgagcat gcaatccctg  960
agtaaaggtc tgtcctatgc agaaagcatc ctgggcgaca ccagaggcca tgggatgtcg  1020
cgagcggaag tgatcagcga tgccttgagg atggacggga tgccatttct ggccagattg  1080
aagctatcac tgtctgccaa tggctatgac ccggacaacc cggcccttcg aaacacgaaa  1140
tga                                                               1143
```

The encoded protein, designated $HopPsyA_{Pto}$, has an amino acid sequence according to SEQ ID No: 22 as follows:

```
Met Asn Pro Ile Gln Ser Arg Phe Ser Ser Val Gln Glu Leu Arg Arg
  1               5                  10                  15

Ser Asn Val Asp Ile Pro Ala Leu Lys Ala Asn Gly Gln Leu Glu Val
             20                  25                  30

Asp Gly Lys Arg Tyr Glu Ile Arg Ala Ala Asp Asp Gly Thr Ile Ser
         35                  40                  45

Val Leu Arg Pro Glu Gln Gln Ser Lys Ala Lys Ser Phe Phe Lys Gly
     50                  55                  60

Ala Ser Gln Leu Ile Gly Gly Ser Ser Gln Arg Ala Gln Ile Ala Gln
 65                  70                  75                  80

Ala Leu Asn Glu Lys Val Ala Ser Ala Arg Thr Val Leu His Gln Ser
                 85                  90                  95

Ala Met Thr Gly Gly Arg Leu Asp Thr Leu Glu Arg Gly Glu Ser Ser
            100                 105                 110

Ser Ala Thr Thr Ala Ile Lys Pro Thr Ala Lys Gln Ala Ala Gln Ser
        115                 120                 125

Thr Phe Asn Ser Phe His Glu Trp Ala Lys Gln Ala Glu Ala Met Arg
    130                 135                 140
```

```
Asn Pro Ser Arg Met Asp Ile Tyr Lys Ile Tyr Lys Gln Asp Ala Pro
145                 150                 155                 160

His Ser His Pro Met Ser Asp Glu Gln Gln Glu Glu Phe Leu His Thr
                165                 170                 175

Leu Lys Ala Leu Asn Gly Lys Asn Gly Ile Glu Val Arg Thr Gln Asp
            180                 185                 190

His Asp Ser Val Arg Asn Lys Lys Asp Arg Asn Leu Asp Lys Tyr Ile
            195                 200                 205

Ala Glu Ser Pro Asp Ala Lys Arg Phe Phe Tyr Arg Ile Ile Pro Lys
        210                 215                 220

His Glu Arg Arg Glu Asp Lys Asn Gln Gly Arg Leu Thr Ile Gly Val
225                 230                 235                 240

Gln Pro Gln Tyr Ala Thr Gln Leu Thr Arg Ala Met Ala Thr Leu Ile
                245                 250                 255

Gly Lys Glu Ser Ala Ile Thr His Gly Lys Val Ile Gly Pro Ala Cys
            260                 265                 270

His Gly Gln Met Thr Asp Ser Ala Val Leu Tyr Ile Asn Gly Asp Val
            275                 280                 285

Ala Lys Ala Glu Lys Leu Gly Glu Lys Leu Lys Gln Met Ser Gly Ile
        290                 295                 300

Pro Leu Asp Ala Phe Val Glu His Thr Pro Leu Ser Met Gln Ser Leu
305                 310                 315                 320

Ser Lys Gly Leu Ser Tyr Ala Glu Ser Ile Leu Gly Asp Thr Arg Gly
                325                 330                 335

His Gly Met Ser Arg Ala Glu Val Ile Ser Asp Ala Leu Arg Met Asp
            340                 345                 350

Gly Met Pro Phe Leu Ala Arg Leu Lys Leu Ser Leu Ser Ala Asn Gly
            355                 360                 365

Tyr Asp Pro Asp Asn Pro Ala Leu Arg Asn Thr Lys
370                 375                 380
```

HopPsyA$_{Pto}$ has been shown to be a secreted protein that is expressed by DC3000. It has been shown that HopPsyA is characterized by cytotoxicity when expressed recombinantly in eukaryotes (i.e., in plants and yeast), and further that HopPsyA is capable of altering metabolic (e.g., Mad2) pathways in targeted cells (see PCT Application Publication No. WO 01/75066 to Collmer et al., published Oct. 11, 2001, which is hereby incorporated by reference in its entirety). Moreover, it has been shown that HopPsyA (HrmA) can be used to effect enhanced resistance to bacterial, fungal, and viral pathogens upon recombinant expression thereof in plants (U.S. Pat. No. 6,342,654 to Li et al., which is hereby incorporated by reference in its entirety). Based on its shared amino acid identity of about 52% when compared to HopPsyA, it is believed that HopPsyA$_{Pto}$ possesses these same characteristics.

A twelfth nucleic acid molecule is hopPtoB2, a homolog of hopB of *Pseudomonas syringae* pv. *syringae* DC3000, and has a nucleotide sequence according to SEQ ID No: 23 as follows:

```
gtgccgcgta tcgtcgccgg ccatgcagaa ggcgtgtgcg tggtcaacgg ccggcactat   60
gtcgagctgt ccggtagaac ctttcaagtc cattacgaca cacatctgcg cggctggcag  120
attgtcgatc cagaaaaccc gttcgccttt tttggccagc agccggtgcg cctagatgaa  180 cagggggcaat ggcagcttgt cgcccgtcga cgtctgcgtg gcggtggcgt aggtgactcc  240
agccatgccc acctgcccga agaaacaccg ggctccagca caggctcgat tccgagcgac  300
tacgaaatgc cggccgccat gcaggcaggc cttgatgtcg tgttgagcaa caagccctac  360
gacccgaccg ggattggcat ggagtcttac tttgagagct atttcgtgga tctgcgtcag  420
agttttgtgg cgcgcaggga aaagctttat gaggatgccc ggacattttt cgccggtttt  480
tctccgccgc caaagccgca attgcctccg ctggcgccac ctgttgccat cgacaccctg  540
```

```
attgaacacg tcttcgcgca gggtaacggc ctggttttga gtgaagcacc gaagtcggtc    600
gccagcaaac ggctgctgtt actcaacatg ccgctgctgg ccgaacagcg tgtcaagatt    660
ctgtatatcg agcacctgct gaccgacaag cacctgtcta aactggccag gtatcgtcaa    720
ctgggcaaaa agagccgctc aggctcgcac gaactcaagc attacctgca cgatctcaac    780
cgcgggacgc tgaacaattc cagcaccgac tacgactatt accacctcat caaggcagcg    840
catcgctatg gtatcgaggt gcgaccgttc agctcgtcga tcagctaccc gtttctggac    900
catccggtat tgagcgcagc caacgacacg actgcagtac aaaaaatgag caattttttc    960
ggccatacgc tcatcagcag cgatgtcgca tccgcgccga caaaacgctg ggttgccttg    1020
ctcgaccaga agctggccac gacccacgac ggggtattag gcattgccga aatgcagggc    1080
gtggtcagtg tgcatgtccg cgacatcccg gcaggccggc cgacgcgcat cactaaaggc    1140
acaggcgaac tgccacgcga gggcacgcag gcccgctgcg acttcacgat tgcgttttcc    1200
gatccgacgc tgattgtgcc ccaggcgcct cacccgcacg gtaccaaaact ggacgacatg    1260 ctgctcagag aactgagggg ccaatctgcc ggtgccgggg gcgaacgctg ggccggccag    1320
tacggattca tccgtgacga ggacggtgcc tggcggtgga tcgcgcctga ggactggccc    1380
gcagacagcc cgatgacggc aatccagcaa tccctgaccg accctgtcta tgagatgcca    1440
ctggacactc gaacaacgct tcatacgctg gcgaacttcg aaagaagggg gctcgacatg    1500
gagtatttct ttgaagaaag ccagtacgaa actgttcgca acgtattcgc cctgcaccgc    1560
aaaaagctgc aacaggatgc ggccttgatc agcgctgtac agttgccgcc tcgtccgacg    1620
atgccggccg tcaaccctcg gacgaccacg gcgcagctgt ttgaaacgct gtaccagcac    1680
accgatggca tcgtgatcgg cgagtcgcat ttttcggtcg ccagcaagaa aatgatcatc    1740
gacaacctgc cgttgctgtc gcagcaaaac gtacgaacgc tgtacatgga gcacttgctc    1800
accgacttgc atcaggcgga tctggatcgc tttttcgaaa cagggcaaat gagcaaaacc    1860
ctgcttcacg acctgaaagt gctggatcgg ggccatcgca ccgacccgga caaggtttac    1920 accttttgagc aactggtcat caaggcgcag cagcacggca tggaagtccg cgccatcgac    1980
tgcgcagcca gctaccacct tagtggcctt gacaacgatg gttcaatcac ccgtcagcaa    2040
atgatgaact actttgcgtc gcgcacccctg cgcaggcatc aggacgtcat gggctcacac    2100
aagtggatcg cgctggtcgg caacagccat tccaatgtct atcaaggcgt cgtgcctggt    2160
atcgccgagc tggaaggcgg catcggcctg cgggttatcg acgtggcacc ggggcagtcg    2220
aagggtgtca tgcacgacct gggggagctg gtctcggcag acatctcgag aaccaaagta    2280
cacatcaaag gcgattatcg agtggagata gaaataccgc gtgcgaagga tgccattcgg    2340 ccacccccagc ctgttaccct cgaacagcga ctggccagac cgggattgtt tctggtggaa    2400
gagagtgagg gcaatctgct gaccattgtc caccgcgctc gcgacacctg gattcaccgc    2460
acgccggtgc tggtcaatgc cgagggcaag ctgtacctgg agcgcgtgcg ctggccgcgc    2520
atccacctca aaccctttga tgacatggac gcgctggtag cggcgctgga ggagatgaac    2580
ctgacgcggg taggctga                                                  2598
```

The encoded HopPtoB2 protein has an amino acid sequence according to SEQ ID No: 24 as follows:

```
Val Pro Arg Ile Val Ala Gly His Ala Glu Gly Val Cys Val Val Asn
 1               5                  10                  15

Gly Arg His Tyr Val Glu Leu Ser Gly Arg Thr Phe Gln Val His Tyr
                 20                  25                  30

Asp Thr His Leu Arg Gly Trp Gln Ile Val Asp Pro Glu Asn Pro Phe
                 35                  40                  45

Ala Phe Gly Gln Gln Pro Val Arg Leu Asp Glu Gln Gly Gln Trp
 50                  55                  60

Gln Leu Val Ala Arg Arg Arg Leu Arg Gly Gly Val Gly Asp Ser
 65                  70                  75                  80

Ser His Ala His Leu Pro Glu Glu Thr Pro Gly Ser Ser Thr Gly Ser
                 85                  90                  95

Ile Pro Ser Asp Tyr Glu Met Pro Ala Ala Met Gln Ala Gly Leu Asp
                 100                 105                 110

Val Val Leu Ser Asn Lys Pro Tyr Asp Pro Thr Gly Ile Gly Met Glu
                 115                 120                 125

Ser Tyr Phe Glu Ser Tyr Phe Val Asp Leu Arg Gln Ser Phe Val Ala
 130                 135                 140

Arg Arg Glu Lys Leu Tyr Glu Asp Ala Arg Thr Phe Phe Ala Gly Phe
145                 150                 155                 160

Ser Pro Pro Lys Pro Gln Leu Pro Leu Ala Pro Pro Val Ala
                 165                 170                 175

Ile Asp Thr Leu Ile Glu His Val Phe Ala Gln Gly Asn Gly Leu Val
                 180                 185                 190

Leu Ser Glu Ala Pro Lys Ser Val Ala Ser Lys Arg Leu Leu Leu Leu
                 195                 200                 205

Asn Met Pro Leu Leu Ala Glu Gln Arg Val Lys Ile Leu Tyr Ile Glu
 210                 215                 220

His Leu Leu Thr Asp Lys His Leu Ser Lys Leu Ala Arg Tyr Arg Gln
225                 230                 235                 240

Leu Gly Lys Lys Ser Arg Ser Gly Ser His Glu Leu Lys His Tyr Leu
                 245                 250                 255

His Asp Leu Asn Arg Gly Thr Leu Asn Asn Ser Ser Thr Asp Tyr Asp
                 260                 265                 270

Tyr Tyr His Leu Ile Lys Ala Ala His Arg Tyr Gly Ile Glu Val Arg
                 275                 280                 285

Pro Phe Ser Ser Ser Ile Ser Tyr Pro Phe Leu Asp His Pro Val Leu
 290                 295                 300

Ser Ala Ala Asn Asp Thr Thr Ala Val Gln Lys Met Ser Asn Phe Phe
305                 310                 315                 320

Gly His Thr Leu Ile Ser Ser Asp Val Ala Ser Ala Pro Thr Lys Arp
                 325                 330                 335

Trp Val Ala Leu Leu Asp Gln Lys Leu Ala Thr Thr His Asp Gly Val
                 340                 345                 350

Leu Gly Ile Ala Glu Met Gln Gly Val Val Ser Val His Val Arg Asp
                 355                 360                 365

Ile Pro Ala Gly Arg Pro Thr Arg Ile Thr Lys Gly Thr Gly Glu Leu
                 370                 375                 380

Pro Arp Glu Gly Thr Gln Ala Arg Cys Asp Phe Thr Ile Ala Phe Ser
385                 390                 395                 400
```

-continued

```
Asp Pro Thr Leu Ile Val Pro Gln Ala Pro His Pro His Gly Thr Lys
                405                 410                 415
Leu Asp Asp Met Leu Leu Arg Glu Leu Arg Gly Gln Ser Ala Gly Ala
            420                 425                 430
Gly Gly Glu Arg Trp Ala Gly Gln Tyr Gly Phe Ile Arg Asp Glu Asp
        435                 440                 445
Gly Ala Trp Arg Trp Ile Ala Pro Glu Asp Trp Pro Ala Asp Ser Pro
    450                 455                 460
Met Thr Ala Ile Gln Gln Ser Leu Thr Asp Pro Val Tyr Glu Met Pro
465                 470                 475                 480
Leu Asp Thr Arg Thr Thr Leu His Thr Leu Ala Asn Phe Glu Arg Arg
                485                 490                 495
Gly Leu Asp Met Glu Tyr Phe Phe Glu Glu Ser Gln Tyr Glu Thr Val
            500                 505                 510
Arg Asn Val Phe Ala Leu His Arg Lys Lys Leu Gln Gln Asp Ala Ala
        515                 520                 525
Leu Ile Ser Ala Val Gln Leu Pro Pro Arg Pro Thr Met Pro Ala Val
    530                 535                 540
Asn Pro Arg Thr Thr Thr Ala Gln Leu Phe Glu Thr Leu Tyr Gln His
545                 550                 555                 560
Thr Asp Gly Ile Val Ile Gly Glu Ser His Phe Ser Val Ala Ser Lys
                565                 570                 575
Lys Met Ile Ile Asp Asn Leu Pro Leu Leu Ser Gln Gln Asn Val Arg
            580                 585                 590
Thr Leu Tyr Met Glu His Leu Leu Thr Asp Leu His Gln Ala Asp Leu
        595                 600                 605
Asp Arg Phe Phe Glu Thr Gly Gln Met Ser Lys Thr Leu Leu His Asp
    610                 615                 620
Leu Lys Val Leu Asp Arg Gly His Arg Thr Asp Pro Asp Lys Val Tyr
625                 630                 635                 640
Thr Phe Glu Gln Leu Val Ile Lys Ala Gln Gln His Gly Met Glu Val
                645                 650                 655
Arg Ala Ile Asp Cys Ala Ala Ser Tyr His Leu Ser Gly Leu Asp Asn
            660                 665                 670
Asp Gly Ser Ile Thr Arg Gln Gln Met Met Asn Tyr Phe Ala Ser Arg
        675                 680                 685
Thr Leu Arg Arg His Gln Asp Val Met Gly Ser His Lys Trp Ile Ala
    690                 695                 700
Leu Val Gly Asn Ser His Ser Asn Val Tyr Gln Gly Val Val Pro Gly
705                 710                 715                 720
Ile Ala Glu Leu Glu Gly Gly Ile Gly Leu Arg Val Ile Asp Val Ala
                725                 730                 735
Pro Gly Gln Ser Lys Gly Val Met His Asp Leu Gly Glu Leu Val Ser
            740                 745                 750
Ala Asp Ile Ser Arg Thr Lys Val His Ile Lys Gly Asp Tyr Arg Val
        755                 760                 765
Glu Ile Glu Ile Pro Arg Ala Lys Asp Ala Ile Arg Pro Gln Pro
    770                 775                 780
Val Thr Leu Glu Gln Arg Leu Ala Arg Pro Gly Leu Phe Leu Val Glu
785                 790                 795                 800
Glu Ser Glu Gly Asn Leu Leu Thr Ile Val His Arg Ala Arg Asp Thr
                805                 810                 815
Trp Ile His Arg Thr Pro Val Leu Val Asn Ala Glu Gly Lys Leu Tyr
            820                 825                 830
```

```
                                    -continued
Leu Glu Arg Val Arg Trp Pro Arg Ile His Leu Lys Pro Phe Asp Asp
        835                 840                 845

Met Asp Ala Leu Val Ala Ala Leu Glu Glu Met Asn Leu Thr Arg Val
    850                 855                 860

Gly
865
```

HopPtoB2 has been shown to be a secreted protein that is expressed by DC3000.

Fragments of the above-identified proteins or polypeptides as well as fragments of full length proteins can also be used according to the present invention.

Suitable fragments can be produced by several means. Subclones of the gene encoding a known protein can be produced using conventional molecular genetic manipulation for subcloning gene fragments, such as described by Sambrook et al., *Molecular Cloning: A Laboratory Manual*, Cold Springs Laboratory, Cold Springs Harbor, N.Y. (1989), and Ausubel et al. (ed.), *Current Protocols in Molecular Biology*, John Wiley & Sons (New York, N.Y.) (1999 and preceding editions), each of which is hereby incorporated by reference in its entirety. The subclones then are expressed in vitro or in vivo in bacterial cells to yield a smaller protein or polypeptide that can be tested for activity, e.g., as a product required for pathogen virulence.

In another approach, based on knowledge of the primary structure of the protein, fragments of the protein-coding gene may be synthesized using the PCR technique together with specific sets of primers chosen to represent particular portions of the protein. Erlich, H. A., et al., "Recent Advances in the Polymerase Chain Reaction," *Science* 252: 1643–51 (1991), which is hereby incorporated by reference. These can then be cloned into an appropriate vector for expression of a truncated protein or polypeptide from bacterial cells as described above.

As an alternative, fragments of a protein can be produced by digestion of a full-length protein with proteolytic enzymes like chymotrypsin or *Staphylococcus* proteinase A, or trypsin. Different proteolytic enzymes are likely to cleave different proteins at different sites based on the amino acid sequence of the particular protein. Some of the fragments that result from proteolysis may be active virulence proteins or polypeptides.

Chemical synthesis can also be used to make suitable fragments. Such a synthesis is carried out using known amino acid sequences for the polyppetide being produced. Alternatively, subjecting a full length protein to high temperatures and pressures will produce fragments. These fragments can then be separated by conventional procedures (e.g., chromatography, SDS-PAGE).

Variants may also (or alternatively) be modified by, for example, the deletion or addition of amino acids that have minimal influence on the properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification, or identification of the polypeptide.

The proteins or polypeptides used in accordance with the present invention are preferably produced in purified form (preferably at least about 80%, more preferably 90%, pure) by conventional techniques. Typically, the protein or polypeptide of the present invention is secreted into the growth medium of recombinant host cells (discussed infra). Alternatively, the protein or polypeptide of the present invention is produced but not secreted into growth medium. In such cases, to isolate the protein, the host cell (e.g., *E. coli*) carrying a recombinant plasmid is propagated, lysed by sonication, heat, or chemical treatment, and the homogenate is centrifuged to remove bacterial debris. The supernatant is then subjected to sequential ammonium sulfate precipitation. The fraction containing the protein or polypeptide of interest is subjected to gel filtration in an appropriately sized dextran or polyacrylamide column to separate the proteins. If necessary, the protein fraction may be further purified by HPLC.

Other DNA molecules encoding other effector proteins or polypeptides can also be identified by determining whether such DNA molecules hybridize under stringent conditions to a nucleic acid molecule as identified above. An example of suitable stringency conditions is when hybridization is carried out at a temperature of about 37° C. using a hybridization medium that includes 0.9× sodium citrate ("SSC") buffer, followed by washing with 0.2×SSC buffer at 37° C. Higher stringency can readily be attained by increasing the temperature for either hybridization or washing conditions or increasing the sodium concentration of the hybridization or wash medium. Nonspecific binding may also be controlled using any one of a number of known techniques such as, for example, blocking the membrane with protein-containing solutions, addition of heterologous RNA, DNA, and SDS to the hybridization buffer, and treatment with RNase. Wash conditions are typically performed at or below stringency. Exemplary high stringency conditions include carrying out hybridization at a temperature of about 42° C. up to and including about 65° C. for up to about 20 hours in a hybridization medium containing 1M NaCl, 50 mM Tris-HCl, pH 7.4, 10 mM EDTA, 0.1% sodium dodecyl sulfate (SDS), 0.2% ficoll, 0.2% polyvinylpyrrolidone, 0.2% bovine serum albumin, and 50 μg/ml *E. coli* DNA, followed by washing carried out at between about 42° C. to about 65° C. in a 0.2×SSC buffer.

The delivery of effector proteins or polypeptides can be achieved in several ways: (1) as a stable transgene; (2) transiently expressed via *Agrobacterium* or viral vectors; (3) delivered by the type III secretion systems of disarmed pathogens or recombinant nonpathogenic bacteria which express a functional, heterologous type III secretion system; or (4) delivered via topical application followed by TAT protein transduction domain-mediated spontaneous uptake into cells. Each of these is discussed infra.

The DNA molecule encoding the protein or polypeptide can be incorporated in cells using conventional recombinant DNA technology. Generally, this involves inserting the DNA molecule into an expression system to which the DNA molecule is heterologous (i.e. not normally present). The heterologous DNA molecule is inserted into the expression system or vector in proper sense orientation and correct reading frame. The vector contains the necessary elements for the transcription and translation of the inserted protein-coding sequences.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Recombinant genes may also be introduced into viruses, such as vaccina virus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC1084, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif., which is hereby incorporated by reference), pQE, pIH821, pGEX, pET series (see F. W. Studier et. al., "Use of T7 RNA Polymerase to Direct Expression of Cloned Genes," *Gene Expression Technology* vol. 185 (1990), which is hereby incorporated by reference in its entirety), and any derivatives thereof Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Cold Springs Laboratory, Cold Springs Harbor, N.Y. (1989), which is hereby incorporated by reference in its entirety.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation).

Transcription of DNA is dependent upon the presence of a promoter which is a DNA sequence that directs the binding of RNA polymerase and thereby promotes mRNA synthesis. The DNA sequences of eukaryotic promoters differ from those of prokaryotic promoters. Furthermore, eukaryotic promoters and accompanying genetic signals may not be recognized in or may not function in a prokaryotic system, and, further, prokaryotic promoters are not recognized and do not function in eukaryotic cells.

Similarly, translation of mRNA in prokaryotes depends upon the presence of the proper prokaryotic signals which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology*, 68:473 (1979), which is hereby incorporated by reference in its entirety.

Promoters vary in their "strength" (i.e. their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operations, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in prokaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires an SD sequence about 7–9 bases 5' to the initiation codon ("ATG") to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Once the isolated DNA molecule encoding the polypeptide or protein has been cloned into an expression system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, insect, plant, and the like.

Because it is desirable for recombinant host cells to secrete the encoded protein or polypeptide, it is preferable that the host cell also possess a functional type III secretion system. The type III secretion system can be heterologous to host cell (Ham et al., "A Cloned *Erwinia chrysanthemi* Hrp (Type III Protein Secretion) System Functions in *Escherichia coli* to Deliver *Pseudomonas syringae* Avr Signals to Plant Cells and Secrete Avr Proteins in Culture," *Microbiol.* 95:10206–10211 (1998), which is hereby incorporated by reference in its entirety) or the host cell can naturally possess a type III secretion system. Host cells which naturally contain a type III secretion system include many pathogenic Gram-negative bacterium, such as numerous *Erwinia* species, *Pseudomonas* species, *Xanthomonas* species, etc. Other type III secretion systems are known and still others are continually being identified. Pathogenic bacteria that can be utilized to deliver effector proteins or polypeptides are preferably disarmed according to known techniques, i.e., as described above. Alternatively, isolation of the effector protein or polypeptide from the host cell or growth medium can be carried out as described above.

Another aspect of the present invention relates to a transgenic plant which express a protein or polypeptide of the present invention and methods of making the same.

In order to express the DNA molecule in isolated plant cells or tissue or whole plants, a plant expressible promoter is needed. Any plant-expressible promoter can be utilized regardless of its origin, i.e., viral, bacterial, plant, etc. Without limitation, two suitable promoters include the nopaline synthase promoter (Fraley et al., *Proc. Natl. Acad. Sci. USA* 80:4803–4807 (1983), which is hereby incorporated by reference in its entirety) and the cauliflower mosaic virus 35S promoter (O'Dell et al., "Identification of DNA Sequences Required for Activity of the Cauliflower Mosaic Virus 35S Promoter," *Nature,* 313(6005):810–812 (1985), which is hereby incorporated by reference in its entirety). Both of these promoters yield constitutive expression of coding sequences under their regulatory control.

While constitutive expression is generally suitable for expression of the DNA molecule, it should be apparent to those of skill in the art that temporally or tissue regulated expression may also be desirable, in which case any regulated promoter can be selected to achieve the desired expression. Typically, the temporally or tissue regulated promoters will be used in connection with the DNA molecule that are expressed at only certain stages of development or only in certain tissues.

In some plants, it may also be desirable to use promoters which are responsive to pathogen infiltration or stress. For example, it may be desirable to limit expression of the protein or polypeptide in response to infection by a particular pathogen of the plant. One example of a pathogen-inducible promoter is the gst1 promoter from potato, which is described in U.S. Pat. Nos. 5,750,874 and 5,723,760 to Strittmayer et al., each of which is hereby incorporated by reference in its entirety.

Expression of the DNA molecule in isolated plant cells or tissue or whole plants also requires appropriate transcription termination and polyadenylation of mRNA. Any 3' regulatory region suitable for use in plant cells or tissue can be operably linked to the first and second DNA molecules. A number of 3' regulatory regions are known to be operable in plants. Exemplary 3' regulatory regions include, without limitation, the nopaline synthase 3' regulatory region (Fraley, et al., "Expression of Bacterial Genes in Plant Cells," *Proc. Nat'l. Acad. Sci. USA,* 80:4803–4807 (1983), which is hereby incorporated by reference in its entirety) and the cauliflower mosaic virus 3' regulatory region (Odell, et al., "Identification of DNA Sequences Required for Activity of the Cauliflower Mosaic Virus 35S Promoter," *Nature,* 313 (6005):810–812 (1985), which is hereby incorporated by reference in its entirety).

The promoter and a 3' regulatory region can readily be ligated to the DNA molecule using well known molecular cloning techniques described in Sambrook et al., *Molecular Cloning: A Laboratory Manual*, Second Edition, Cold Spring Harbor Press, NY (1989), which is hereby incorporated by reference in its entirety.

One approach to transforming plant cells with a DNA molecule of the present invention is particle bombardment (also known as biolistic transformation) of the host cell. This can be accomplished in one of several ways. The first involves propelling inert or biologically active particles at cells. This technique is disclosed in U.S. Pat. Nos. 4,945, 050, 5,036,006, and 5,100,792, all to Sanford, et al., each of which is hereby incorporated by reference in its entirety. Generally, this procedure involves propelling inert or biologically active particles at the cells under conditions effective to penetrate the outer surface of the cell and to be incorporated within the interior thereof When inert particles are utilized, the vector can be introduced into the cell by coating the particles with the vector containing the heterologous DNA. Alternatively, the target cell can be surrounded by the vector so that the vector is carried into the cell by the wake of the particle. Biologically active particles (e.g., dried bacterial cells containing the vector and heterologous DNA) can also be propelled into plant cells. Other variations of particle bombardment, now known or hereafter developed, can also be used.

Another method of introducing the DNA molecule into plant cells is fusion of protoplasts with other entities, either minicells, cells, lysosomes, or other fusible lipid-surfaced bodies that contain the DNA molecule. Fraley, et al., *Proc. Natl. Acad. Sci. USA,* 79:1859–63 (1982), which is hereby incorporated by reference in its entirety.

The DNA molecule may also be introduced into the plant cells by electroporation. Fromm, et al., *Proc. Natl. Acad. Sci. USA,* 82:5824 (1985), which is hereby incorporated by reference in its entirety. In this technique, plant protoplasts are electroporated in the presence of plasmids containing the DNA molecule. Electrical impulses of high field strength reversibly permeabilize biomembranes allowing the introduction of the plasmids. Electroporated plant protoplasts reform the cell wall, divide, and regenerate.

Another method of introducing the DNA molecule into plant cells is to infect a plant cell with *Agrobacterium tumefaciens* or *Agrobacterium rhizogenes* previously transformed with the DNA molecule. Under appropriate conditions known in the art, the transformed plant cells are grown to form shoots or roots, and develop further into plants. Generally, this procedure involves inoculating the plant tissue with a suspension of bacteria and incubating the tissue for 48 to 72 hours on regeneration medium without antibiotics at 25–28° C.

*Agrobacterium* is a representative genus of the Gram-negative family Rhizobiaceae. Its species are responsible for crown gall (*A. tumefaciens*) and hairy root disease (*A. rhizogenes*). The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue.

Heterologous genetic sequences such as a DNA molecule of the present invention can be introduced into appropriate plant cells by means of the Ti plasmid of *A. tumefaciens* or the Ri plasmid of *A. rhizogenes*. The Ti or Ri plasmid is transmitted to plant cells on infection by *Agrobacterium* and is stably integrated into the plant genome. Schell, J., *Science*, 237:1176–83 (1987), which is hereby incorporated by reference in its entirety.

Plant tissue suitable for transformation include leaf tissue, root tissue, meristems, zygotic and somatic embryos, and anthers.

After transformation, the transformed plant cells can be selected and regenerated.

Preferably, transformed cells are first identified using, e.g., a selection marker simultaneously introduced into the host cells along with the DNA molecule of the present invention. Suitable selection markers include, without limitation, markers coding for antibiotic resistance, such as kanamycin resistance (Fraley, et al., *Proc. Natl. Acad. Sci. USA*, 80:4803–4807 (1983), which is hereby incorporated by reference in its entirety). A number of antibiotic-resistance markers are known in the art and other are continually being identified. Any known antibiotic-resistance marker can be used to transform and select transformed host cells in accordance with the present invention. Cells or tissues are grown on a selection media containing an antibiotic, whereby generally only those transformants expressing the antibiotic resistance marker continue to grow.

Once a recombinant plant cell or tissue has been obtained, it is possible to regenerate a full-grown plant therefrom. Thus, another aspect of the present invention relates to a transgenic plant that includes a DNA molecule of the present invention, wherein the promoter induces transcription of the first DNA molecule in response to infection of the plant by an oomycete. Preferably, the DNA molecule is stably inserted into the genome of the transgenic plant of the present invention.

Plant regeneration from cultured protoplasts is described in Evans, et al., *Handbook of Plant Cell Cultures Vol. 1*: (MacMillan Publishing Co., New York, 1983); and Vasil I. R. (ed.), *Cell Culture and Somatic Cell Genetics of Plants*, Acad. Press, Orlando, Vol. I, 1984, and Vol. III (1986), each of which is hereby incorporated by reference in their entirety.

It is known that practically all plants can be regenerated from cultured cells or tissues, including but not limited to, all major species of rice, wheat, barley, rye, cotton, sunflower, peanut, corn, potato, sweet potato, bean, pea, chicory, lettuce, endive, cabbage, cauliflower, broccoli, turnip, radish, spinach, onion, garlic, eggplant, pepper, celery, carrot, squash, pumpkin, zucchini, cucumber, apple, pear, melon, strawberry, grape, raspberry, pineapple, soybean, tobacco, tomato, sorghum, and sugarcane.

Means for regeneration vary from species to species of plants, but generally a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

After the DNA molecule is stably incorporated in transgenic plants, it can be transferred to other plants by sexual crossing or by preparing cultivars. With respect to sexual crossing, any of a number of standard breeding techniques can be used depending upon the species to be crossed. Cultivars can be propagated in accord with common agricultural procedures known to those in the field.

Diseases caused by the vast majority of bacterial pathogens result in limited lesions. That is, even when everything is working in the pathogen's favor (e.g., no triggering of the hypersensitive response because of R-gene detection of one of the effectors), the parasitic process still triggers defenses after a couple of days, which then stops the infection from spreading. Thus, the very same effectors that enable parasitism to proceed must also eventually trigger defenses. Therefore, premature expression of these effectors is believed to "turn on" plant defenses earlier (i.e., prior to infection) and make the plant resistant to either the specific bacteria from which the effector protein was obtained or many pathogens. An advantage of this approach is that it involves natural products and plants seem highly sensitive to pathogen effector proteins.

According to one embodiment, a transgenic plant is provided that contains a heterologous DNA molecule of the present invention. When the heterologous DNA molecule is expressed in the transgenic plant, plant defenses are activated, imparting disease resistance to the transgenic plant. The transgenic plant can also contain an R-gene whose product is activated by the protein or polypeptide product of the heterologous DNA molecule. The R gene can be naturally occurring in the plant or heterologously inserted therein. By disease resistance, it is believed that the effector proteins of the present invention can impart to plants resistance against bacterial, viral, and/or fungal diseases.

In addition to imparting disease resistance, it is believed that stimulation of plant defenses in transgenic plants of the present invention will also result in a simultaneous enhancement in growth and resistance to insects.

Alternative to transgenic expression is topical application of the effector proteins to plants. The embodiments of the present invention where the effector polypeptide or protein is applied to the plant can be carried out in a number of ways, including: 1) application of an isolated protein (or composition containing the same) or 2) application of bacteria which do not cause disease and are transformed with a gene encoding the effector protein of the present invention. In the latter embodiment, the effector protein can be applied to plants by applying bacteria containing the DNA molecule encoding the effector protein. Such bacteria are preferably capable of secreting or exporting the protein so that the protein can contact plant cells. In these embodiments, the protein is produced by the bacteria in planta.

Such topical application can be carried out using an effector-TAT protein, which will afford transduction domain-mediated spontaneous uptake of the effector protein into cells. Basically, this is carried out by fusing an 11-amino acid peptide (YGRKKRRQRRR, SEQ ID No: 25) by standard rDNA techniques to the N-terminus of the effector protein, and the resulting tagged protein is taken up into animal cells by a poorly understood process. This peptide is the protein transduction domain (PTD) of the human immunodeficiency virus (HIV) TAT protein (Schwarze et al., "Protein transduction: unrestricted delivery into all cells?" *Trends Cell Biol.* 10:290–295 (2000), which is hereby incorporated by reference in its entirety). Other PTDs are known and can be used for this purpose (Prochiantz, "Messenger proteins: homeoproteins, TAT and others," *Curr. Opin. Cell Biol.* 12:400–406 (2000), which is hereby incorporated by reference in its entirety). See PCT Application Publication No. WO 01/19393 to Collmer et al., which is hereby incorporated by reference in its entirety.

When the effector protein is topically applied to plants, it can be applied as a composition, which includes a carrier in the form, e.g., of water, aqueous solutions, slurries, or dry powders. In this embodiment, the composition contains greater than about 5 nM of the protein of the present invention.

Although not required, this composition may contain additional additives including fertilizer, insecticide, fungicide, nematicide, and mixtures thereof Suitable fertilizers include $(NH_4)_2NO_3$. An example of a suitable insecticide is Malathion. Useful fungicides include Captan.

Other suitable additives include buffering agents, wetting agents, coating agents, and, in some instances, abrading agents. These materials can be used to facilitate the process of the present invention.

According to one embodiment, a transgenic plant including a heterologous DNA molecule of the present invention expresses one or more effector proteins, wherein the transgenic plant is capable of supporting growth of compatible nonpathogenic bacteria. The compatible nonpathogenic bacteria can be naturally occurring or it can be recombinant. Preferably, the nonpathogenic bacteria is recombinant and expresses one or more useful products. Thus, the transgenic plant becomes a green factory for producing desirable products. Desirable products include, without limitation, products that can enhance the nutritional quality of the plant or products that are desirable in isolated form If desired in isolated form, the product can be isolated from plant tissues. To prevent competition between the non-pathogenic bacteria which express the desired product and those that do not, it is possible to tailor the needs of recombinant, non-pathogenic bacteria so that only they are capable if living in plant tissues expressing a particular effector protein or polypeptide of the present invention.

The effector proteins or polypeptides of the present invention are believed to alter the plant physiology by shifting metabolic pathways to benefit the parasite and by activating or suppressing cell death pathways. Thus, they may also provide useful tools for efficiently altering the nutrient content of plants and delaying or triggering senescence. There are agricultural applications for all of these possible effects.

Thus, a further aspect of the present invention relates more generally to a method of modifying a metabolic pathway in a cell by introducing into the cell an effector protein or polypeptide of the present invention which interacts with a native cellular protein involved in a metabolic pathway of the cell. As a result of introducing the protein or polypeptide into the cell, the protein or polypeptide modifies the metabolic pathway through its interaction with the native cellular protein. By way of example, the HopPsy$A_{Pto}$ protein (SEQ ID No: 22) is believed to interact with Mad2.

Yet another aspect of the present invention relates to a method of causing eukaryotic cell death which is carried out by introducing into a eukaryotic cell a *Pseudomonas* protein which is cytotoxic and causes cell death. One preferred protein of the present invention is HopPsy$A_{Pto}$ (SEQ ID No: 22), homolog of HopPsyA. The eukaryotic cell which is treated can be either in vitro or in vivo. When treating eukaryotic cells in vivo, a number of different protein- or DNA-delivery systems can be employed to introduce the effector protein into the target eukaryotic cell.

The protein- or DNA-delivery systems can be provided in the form of pharmaceutical compositions which include the delivery system in a pharmaceutically acceptable carrier, which may include suitable excipients or stabilizers. The dosage can be in solid or liquid form, such as powders, solutions, suspensions, or emulsions. Typically, the composition will contain from about 0.01 to 99 percent, preferably from about 20 to 75 percent of active compound(s), together with the carrier, excipient, stabilizer, etc.

The compositions of the present invention are preferably administered in injectable or topically-applied dosages by solution or suspension of these materials in a physiologically acceptable diluent with a pharmaceutical carrier. Such carriers include sterile liquids, such as water and oils, with or without the addition of a surfactant and other pharmaceutically and physiologically acceptable carrier, including adjuvants, excipients or stabilizers. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

Alternatively, the effector proteins can also be delivered via solution or suspension packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

Depending upon the treatment being effected, the compounds of the present invention can be administered orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes.

Compositions within the scope of this invention include all compositions wherein the compound of the present invention is contained in an amount effective to achieve its intended purpose. While individual needs vary, determination of optimal ranges of effective amounts of each component is within the skill of the art.

One approach for delivering an effector protein into cells involves the use of liposomes. Basically, this involves providing a liposome which includes that effector protein to be delivered, and then contacting the target cell with the liposome under conditions effective for delivery of the effector protein into the cell.

Liposomes are vesicles comprised of one or more concentrically ordered lipid bilayers which encapsulate an aqueous phase. They are normally not leaky, but can become leaky if a hole or pore occurs in the membrane, if the membrane is dissolved or degrades, or if the membrane temperature is increased to the phase transition temperature. Current methods of drug delivery via liposomes require that the liposome carrier ultimately become permeable and release the encapsulated drug at the target site. This can be accomplished, for example, in a passive manner wherein the liposome bilayer degrades over time through the action of various agents in the body. Every liposome composition will have a characteristic half-life in the circulation or at other sites in the body and, thus, by controlling the half-life of the liposome composition, the rate at which the bilayer degrades call be somewhat regulated.

In contrast to passive drug release, active drug release involves using an agent to induce a permeability change in the liposome vesicle. Liposome membranes can be constructed so that they become destabilized when the environment becomes acidic near the liposome membrane (see, e.g., *Proc. Natl. Acad. Sci. USA* 84:7851 (1987); *Biochemistry*

28:908 (1989), each of which is hereby incorporated by reference in their entirety). When liposomes are endocytosed by a target cell, for example, they can be routed to acidic endosomes which will destabilize the liposome and result in drug release.

Alternatively, the liposome membrane can be chemically modified such that an enzyme is placed as a coating on the membrane which slowly destabilizes the liposome. Since control of drug release depends on the concentration of enzyme initially placed in the membrane, there is no real effective way to modulate or alter drug release to achieve "on demand" drug delivery. The same problem exists for pH-sensitive liposomes in that as soon as the liposome vesicle comes into contact with a target cell, it will be engulfed and a drop in pH will lead to drug release.

This liposome delivery system can also be made to accumulate at a target organ, tissue, or cell via active targeting (e.g., by incorporating an antibody or hormone on the surface of the liposomal vehicle). This can be achieved according to known methods.

Different types of liposomes can be prepared according to Bangham et al., *J. Mol. Biol.* 13:238–252 (1965); U.S. Pat. No. 5,653,996 to Hsu et al.; U.S. Pat. No. 5,643,599 to Lee et al., U.S. Pat. No. 5,885,613 to Holland et al.; U.S. Pat. No. 5,631,237 to Dzau et al.; and U.S. Pat. No. 5,059,421 to Loughrey et al., each of which is hereby incorporated by reference in their entirety.

An alternative approach for delivery of effector proteins involves the conjugation of the desired effector protein to a polymer that is stabilized to avoid enzymatic degradation of the conjugated effector protein. Conjugated proteins or polypeptides of this type are described in U.S. Pat. No. 5,681,811 to Ekwuribe, which is hereby incorporated by reference in its entirety.

Yet another approach for delivery of proteins or polypeptides involves preparation of chimeric proteins according to U.S. Pat. No. 5,817,789 to Heartlein et al., which is hereby incorporated by reference in its entirety. The chimeric protein can include a ligand domain and, e.g., an effector protein of the present invention. The ligand domain is specific for receptors located on a target cell. Thus, when the chimeric protein is delivered intravenously or otherwise introduced into blood or lymph, the chimeric protein will adsorb to the targeted cell, and the targeted cell will internalize the chimeric protein, which allows the effector protein to destabilize the cell checkpoint control mechanism, affording its cytotoxic effects.

When it is desirable to achieve heterologous expression of an effector protein of the present invention in a target cell, DNA molecules encoding the desired effector protein can be delivered into the cell. Basically, this includes providing a nucleic acid molecule encoding the effector protein and then introducing the nucleic acid molecule into the cell under conditions effective to express the effector protein in the cell. Preferably, this is achieved by inserting the nucleic acid molecule into an expression vector before it is introduced into the cell.

When transforming mammalian cells for heterologous expression of an effector protein, an adenovirus vector can be employed. Adenovirus gene delivery vehicles can be readily prepared and utilized given the disclosure provided in Berkner, *Biotechniques* 6:616–627 (1988) and Rosenfeld et al., *Science* 252:431–434 (1991), WO 93/07283, WO 93/06223, and WO 93/07282, each of which is hereby incorporated by reference in their entirety. Adeno-associated viral gene delivery vehicles can be constructed and used to deliver a gene to cells. The use of adeno-associated viral gene delivery vehicles in vitro is described in Chatterjee et al., *Science* 258:1485–1488 (1992); Walsh et al., *Proc. Nat'l. Acad. Sci.* 89:7257–7261 (1992); Walsh et al., *J. Clin Invest.* 94:1440–1448 (1994); Flotte et al., *J. Biol. Chem.* 268: 3781–3790 (1993); Ponnazhagan et al., *J. Exp. Med.* 179: 733–738 (1994); Miller et al., *Proc. Nat'l Acad. Sci.* 91:10183–10187 (1994); Einerhand et al., *Gene Ther.* 2:336–343 (1995); Luo et al., *Exp. Hematol.* 23:1261–1267 (1995); and Zhou et al., *Gene Ther.* 3:223–229 (1996), each of which is hereby incorporated by reference in their entirety. In vivo use of these vehicles is described in Flotte et al., *Proc. Nat'l Acad. Sci.* 90:10613–10617 (1993); and Kaplitt et al., *Nature Genet.* 8:148–153 (1994), each of which is hereby incorporated by reference in their entirety. Additional types of adenovirus vectors are described in U.S. Pat. No. 6,057,155 to Wickham et al.; U.S. Pat. No. 6,033,908 to Bout et al.; U.S. Pat. No. 6,001,557 to Wilson et al.; U.S. Pat. No. 5,994,132 to Chamberlain et al.; U.S. Pat. No. 5,981,225 to Kochanek et al.; and U.S. Pat. No. 5,885,808 to Spooner et al.; and U.S. Pat. No. 5,871,727 to Curiel, each of which is hereby incorporated by reference in their entirety).

Retroviral vectors which have been modified to form infective transformation systems can also be used to deliver nucleic acid encoding a desired effector protein into a target cell. One such type of retroviral vector is disclosed in U.S. Pat. No. 5,849,586 to Kriegler et al., which is hereby incorporated by reference in its entirety.

Regardless of the type of infective transformation system employed, it should be targeted for delivery of the nucleic acid to a specific cell type. For example, for delivery of the nucleic acid into tumor cells, a high titer of the infective transformation system can be injected directly within the tumor site so as to enhance the likelihood of tumor cell infection. The infected cells will then express the desired effector protein, thereby causing cytotoxic effects.

Particularly preferred is use of the effector proteins of the present invention to treat a cancerous condition (i.e., the eukaryotic cell which is affected is a cancer cell). This can be carried out by introducing or administering to a patient, a cytotoxic *Pseudomonas* protein under conditions effective to inhibit cancer cell division, thereby treating the cancer condition.

By introducing, it is intended that the effector protein is administered to the patient, preferably in the form of a composition which will target delivery to the cancer cells. Alternatively, when using DNA-based therapies, it is intended that the introducing be carried out by administering a targeted DNA delivery system to the patient such that the cancer cells are targeted and the effector protein is expressed therein. A number of known targeted delivery systems are known in the art and can be employed herewith.

EXAMPLES

The following Examples are intended to be illustrative and in no way are intended to limit the scope of the present invention.

Example 1

Detection of Protein Expression by *Pseudomonas syringae* pv. tomato DC3000

ORF-specific DNA fragments were amplified by PCR from DC3000 genomic DNA and printed onto amine-coated slides from Cell Associates (Houston). Each DNA sample was printed three times on each slide with a BioRobotics (Boston) Microgrid II Arrayer by using MicroSpot2500 split pins. Slides were blocked according to the recommended protocol from Cell Associates. Of total RNA, 50–100 µg was used to synthesize cDNA probes for microarray analysis. RNA was mixed with 3 µg of random hexamers (Invitrogen) in a total volume of 15 µl and incubated at 65° C. for 10 min. Reactions were then placed on ice for 2 min, to which were added 3 µl of 1 mM FluoroLink Cy3- or Cy5-dUTP (Amersham Biosciences, Piscataway, N.J.), 3 µl of 0.1 M DTT, 6 µl of 5× first-strand buffer, 0.6 µl of 50×dNTPs mix (25 mM dATP, dCTP, dGTP/10 mM dTTP), and 2 µl of Superscript II (GIBCO/BRL). Reactions were incubated at room temperature for 10 min, followed by 42° C. for 110 min. RNA was hydrolyzed by adding 1.5 µl of 1 M NaOH at 65° C. for 10 min followed by neutralizing with 1.5 µl of 1 M HCl. cDNA probes were purified by using a PCR purification kit (Qiagen, Valencia, Calif.) and were resuspended in 20 µl of hybridization buffer (5×SSC, 0.1% SDS, and 25% formamide, where 1×SSC=0.15 M sodium chloride/0.015 M sodium citrate, pH 7). Denatured probes (99° C., 2 min) were hybridized to slides at 60° C. overnight in hybridization cassettes (Coming), after which slides were washed twice with 2×SSC, 0.1% SDS (60° C., 5 min), once with 2×SSC (room temperature, 5 min), and once with 0.2×SSC (room temperature, 5 min).

Microarray images were visualized by using a ScanArray 5000 (Packard), using laser and PMT settings of 100 and 90, respectively. Images were overlaid and quantified by using IMAGENE 4.1 software (BioDiscovery; Marina Del Rey, Calif.). Ratio data were extracted by using GENESIGHT 2.1 software (BioDiscovery). For these analyses, local background for each spot was corrected, and signals lower than 50 were flagged and eliminated. After flooring low signals to the value of 100, ratios of the overlaid images were calculated for individual spots. 16S rRNA was used and, to normalize the data, the 16S rRNA was expressed to similar levels in both tested strains based on RNA blots. Finally, all of the replicated data were combined, and mean ratio data and SDs were calculated for each ORF.

To corroborate the microarray results, RNA blotting was performed on 10 ORFs from similarly grown cultures. RNA blot analyses were performed as described (Sambrook et al., *Molecular Cloning: A Laboratory Manual*, Cold Spring Harbor Lab. Press, Plainview, N.Y.(1989), which is hereby incorporated by reference). Of each RNA sample, 25 µg was resolved on 1.2% formaldehyde-agarose gels and transferred to Nylon membranes (Hybond-N+) by capillary blotting using 20×SSC. transferred to Nylon membranes (Hybond-N+) by capillary blotting using 20×SSC. RNA was bound to the membrane by UV cross-linking. Probes were generated by PCR amplification from genomic DNA, using ORF-specific primers, and labeled with $^{32}$P-dATP by random priming with a DECAprime II kit (Ambion). Hybridization was performed in 5×SSC, 50% formamide, 0.1% sodium-lauroylsarcosine,0.02% SDS, and 2% blocking reagent (Roche Molecular Biochemicals) at 42° C. overnight. Membranes were then washed twice with 2×SSC/0.1% SDS for 15 min, twice with 1×SSC/0.1% SDS for 15 min, and once with 0.1×SSC/0.1% SDS for 15 min before exposure on a phosphor screen. Signals were detected and evaluated by using a Storm system (Molecular Dynamics) (FIG. 1).

The microarray experiments were in qualitative agreement with the RNA blot. These data indicate that Hrp promoter candidates with E values smaller (more significant) than 1e–4 are expressed at levels detected by the microarray and RNA blotting. However, within this group there was no apparent relationship between the magnitude of the E value and the level of expression. Furthermore, one of 16 examined ORFs (see Fouts et al. (*Proc. Natl. Acad. Sci USA* 99: 2275–2280 (2002), which is hereby incorporated by reference in its entirety) with an E value substantially lower than this threshold, AvrXv3 (4e–6), was expressed at a level that was detected only by RNA blot analysis (Table 1 below), indicating that significant E values do not always predict strong expression.

TABLE 1

Results of Microarray Analysis

| Designation | GenBank accession number[1] | Amino acid % identity | BLASTP p value | HMM E-value | Microarray signal ratio[2] |
|---|---|---|---|---|---|
| HopPsyA$_{Pto}$ | L14926 | 52 | 9e–93 | 1.0e–5 | 11 ± 9 |
| AvrPphE$_{Pto}$ | U16817 | 67 | 1e–117 | 2.5e–4 | 5 ± 2 |
| AvrPphF$_{Pto}$ | AF231452 | 51 | 3e–36 | 1.7e–6 | 3 ± 2 |
| AvrPphD1$_{Pto}$ | AJ277494 | 89 | 0 | 1.9e–6 | 30 ± 17 |
| AvrXv3$_{Pto}$ | AF190120 | 27 | 7e–12 | 3.4e–6 | ND |
| AvrPpiB1$_{Pto}$ | X84843 | 100 | 1e–152 | 7.8e–6 | 11 ± 9 |
| AvrPpiB2$_{Pto}$ | X84843 | 100 | 1e–150 | 7.8e–6 | 10 ± 6 |
| AvrPphD2$_{Pto}$ | AJ277494 | 53 | 2e–44 | 3.0e–5 | 27 ± 11 |
| HopPtoB2[3] | AF232004 | | | 2.6e–3 | ND |
| AvrRps4$_{Pto}$ | L43559 | 72 | 2e–44 | 2.5e–2 | ND |
| Reference genes | | | | | |
| 16S rRNA* | | | | | 1 |
| 23S rRNA** | | | | | 1 |

[1]GenBank accession number AF232004 is for DC3000 sequences, all others are for homologs originally found in other bacteria.
[2]Microarray signal is the mean ratio and standard deviation from 3 replicates of 2 independent experiments, calculated as described in the Materials and Methods. AvrPpiB1$_{Pto}$ and AvrPpiB2$_{Pto}$ are 100% identical, so their signals cannot be distinguished. AvrPphD1$_{Pto}$ and AvrPphD2$_{Pto}$ are 62% identical. ND = not detected.
[3]HopPtoB1 is secreted in a Hrp-dependent manner; HopPtoB2 has duplicated regions of homology with HopPtoB1.

By using an iterative process involving computational and gene expression data, an initial inventory of P. s. tomato DC3000 candidate type III secretion effector proteins was obtained. These are the presumed prime agents of host metabolic subversion. These analyses have revealed that the Hrp regulon, the primary regulon known to be expressed during infection, seems to control at least 48 genes and a subsidiary regulon directing phytotoxin production. The iterative process focused on Hrp promoters in DC3000 and featured microarray experiments that tested the activity of novel Hrp promoters and demonstrated the validity of this approach for genomewide transcriptional profiling in DC3000. These findings suggest that the *P. syringae* Hrp regulon is more complex than expected and encompasses more than type III secretion system genes and effector genes.

The global search for DC3000 ORFs that are similar to known Avr/Hop proteins yielded AvrXv3$_{Pto}$, AvrPtoB, and the AvrPphD families as the only candidate effectors shared with *Xanthomonas* spp. (Noel et al., *Mol. Microbiol.* 41:1271–1281 (2001), which is hereby incorporated by reference in its entirety). Notably missing were members of the AvrBs2 and AvrBs3 families, which are widespread in *Xanthomonas* spp., or any members of the AvrRxv/YopJ family, which are found in genera as diverse as *Salmonella, Yersinia, Xanthomonas, Erwinia*, and *Rhizobium*, and have also been reported in another strain of *P. syringae* (i.e., *P. s. syringae* B728a) (Galán & Collmer, *Science* 284:1322–1328 (1999); Alfano et al., *Proc. Natl. Acad. Sci. USA* 97:4856–4861 (2000), each of which is hereby incorporated by reference in its entirety). However, it is important to note that further searches after closure and annotation of the DC3000 genome may yield additional homologs of known effectors. In addition, genomic projects with other pathogens will enlarge the set of candidate effector genes available for comparison.

The majority of *P. syringae* avr genes that have been cloned on the basis of Avr phenotype have come from three pathovars that parasitize legumes *glycinea, phaseolicola*, and *pisi*. P. s. tomato has a different host range and diverges from these other pathovars in rRNA comparisons (Manceau & Horvais, *Appl. Environ. Microbiol.* 63:498–505 (1997), which is hereby incorporated by reference in its entirety). Nevertheless, of the 15 avr gene families found in these legume-attacking pathovars, 6 are also found in DC3000. This finding suggests the existence of a core set of *P. syringae* effectors in addition to those in the Hrp pathogenicity island CEL.

The analyses described above and reported in Fouts et al. (*Proc. Natl. Acad. Sci USA* 99: 2275–2280 (2002), which is hereby incorporated by reference in its entirety) revealed a striking apparent redundancy among the candidate effector protein genes hopPtoA, hopPtoB, avrPphD$_{Pto}$, and avrPpiB1$_{Pto}$, as well as in three Hrp-related factors that may play a role in type III protein translocation across bacterial and plant cell walls.

All of the analyzed candidate effector genes seem to be expressed in a HrpL-dependent manner except for avrRps4$_{Pto}$, hopPtoA2, and hopPtoB2 (avrXv3$_{Pto}$ was HrpL-activated, but relatively poorly). avrRps4$_{Pto}$ was cloned originally from *Pseudomonas syringae pisi* and renders recombinant DC3000 avirulent on most *Arabidopsis* accessions (Hinsch & Staskawicz, *Mol. Plant-Microbe Interact.* 9:55–61 (1996), which is hereby incorporated by reference in its entirety), and avrXv3 is from an *Xanthomonas campestris* pv. *vesicatoria* race that is avirulent on tomato carrying the Xv3 R gene (Astua-Monge et al., *Mol. Plant-Microbe Interact.* 13:911–921 (2000), which is hereby incorporated by reference in its entirety). There exists a possibility that poor expression of these two avr genes in DC3000 is a factor in the virulence of DC3000 on Arabidopsis and tomato carrying the cognate R genes.

Example 2

In vitro Secretion of Effector Proteins

Secretion assays were performed using P. s. tomato DC3000 strains carrying a pML123 derivative containing a PCR-cloned ORF (encoding a candidate Hrp-secreted protein) fused to nucleotide sequences that encoded either the HA or FLAG epitopes along with their native ribosome binding sites and an engineered stop codon (Labes et al., *Gene* 89:37–46 (1990), which is hereby incorporated by reference in its entirety).

Four effector proteins were tested for their secretion from the above-identified strains. Primers and the constructs used to prepare the transform the host strains are identified as follows:

For HopPtoC expression, the hopPtoC gene was cloned using forward primer (agtcggatccgaatagggcgct-gaaaatatgacaatcgtgtc, SEQ ID No: 26) containing a BamHI site and reverse primer (agtcctcgagtcacttgtcatcgtcgtc-cttgtagtcgtgtattttgaagcgaa, SEQ ID No: 27) containing an XhoI site and FLAG epitope codons. The hopPtoC gene was cloned into plasmid vector pLN50.

For HopPtoD1 expression, the hopPtoD1 gene was cloned using forward primer (ccacacattggatccgattacttcatc-cgggacagctgatagcgc, SEQ ID No: 28) containing a BamHI site and reverse primer (attctcgagtcatttatcatcat-catctttataatcgggtgcgggctgccgcgac, SEQ ID No: 29) containing an XhoI site and FLAG epitope codons. The hopPtoD1 gene was cloned into plasmid vector pLN167.

For HopPtoD2 expression, the hopPtoD2 gene was cloned using forward primer (atgcaagcttatccaatgcctttcgtca, SEQ ID No: 30) containing a HindIII site and reverse primer (atgc-ctcgagtcaagcgtaatctggaacatcgtatgggtattctaacgctatttttgc, SEQ ID No: 31) containing an XhoI site and HA epitope codons. The hopPtoD2 gene was cloned into plasmid vector pLN130.

For HopPtoJ expression, the hopPtoJ gene was cloned using forward primer (agtaaagcttgagctgcacgcatgcgag, SEQ ID No: 32) containing a HindIII site and reverse primer (agtatctagatcacttgtcatcgtcgtccttgtagtcttgtgcgaccagatgttt, SEQ ID No: 33) containing an XbaI site and FLAG epitope codons. The hopPtoJ gene was cloned into plasmid vector pLN164.

Constructs carrying different epitope-tagged ORFs were electroporated into DC3000 and a DC3000 hrcC mutant and grown in Hrp-inducing conditions (Yuan & He, *J. Bacteriol.* 178:6399–6402 (1996), which is hereby incorporated by reference in its entirety). Additionally, all of the DC3000 strains also carried pCPP2318, a construct that contains blaM lacking signal peptide sequences (Charkowski et al., *J. Bacteriol.* 179:3866–3874 (1997), which is hereby incorporated by reference in its entirety). DC3000 cultures were separated into cell-bound and supernatant fractions as described (van Dijk et al., *J. Bacteriol.* 181:4790–4797 (1999), which is hereby incorporated by reference in its entirety). Proteins were separated with SDS-PAGE by standard procedures (Sambrook et al., *Molecular Cloning Second Ed.* (Cold Spring Harbor Laboratory Press, Cold Spring Harbor, N.Y.) (1989), which is hereby incorporated by reference in its entirety), transferred to polyvinylidene difluoride membranes, and immunoblotted using anti-FLAG (Sigma Chemical Co., St. Louis, Mo.), -HA (Roche Molecular Biochemicals, Indianapolis, Ind.), or -β-lactamase (5 Prime→3 Prime Inc., Boulder, Colo.) as primary antibodies. Primary antibodies were recognized by goat anti-rabbit immunoglobulin G-alkaline phosphatase conjugate (Sigma Chemical Co.), which were visualized by chemiluminescence using a Western-Light chemilumincescence detection system (Tropix, Bedford, Mass.) and X-Omat X-ray film.

Figure 2A:
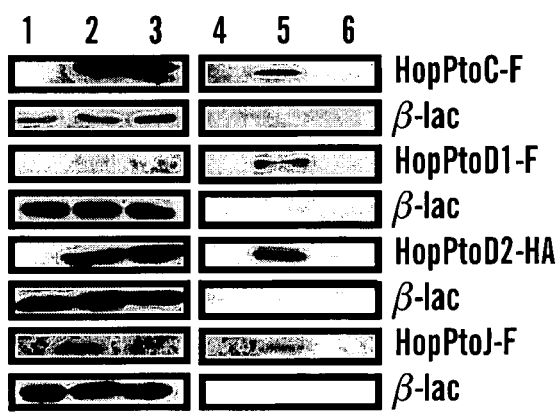
FIGS. 2A–B illustrate assays for Hrp system-dependent secretion in culture or translocation in plants of various Avr and Hop proteins.

Each of these DC3000 proteins were found to be secreted (FIG. 2A). Because the secretability of these proteins was demonstrated (and the avirulence activity of these DC3000 homologs is unknown), the proteins were renamed as HopPtoC (AvrPpiC2 homolog), HopPtoD1 and HopPtoD2 (AvrPphD homologs), and HopPtoJ (AvrXv3 homolog).

Example 3

In vitro Translocation of Effectors

*Arabidopsis thaliana* accession Columbia (Col-0) and rps2–201 mutant plants were grown in a growth chamber with 12 hr of light at 24° C. (22° C. at night) and 70% relative humidity. For HopPtoK expression, the hopPtoK gene was cloned using forward primer (gcgaattcatcggtttaat-cacgcaaggc, SEQ ID No: 34) containing a EcoRI site and reverse primer (ttggtacctcagcagtagagcgtgt, SEQ ID No: 35) containing an KpnI site. The hopPtoK gene was cloned into plasmid vector phopPtoK. In addition, a hopPtoK-'avrRpt2 fusion was prepared using SEQ ID No: 34 (above) as forward primer and reverse primer (aaggatccgcagagcgt-gtcgcgacc, SEQ ID No: 36) containing an BamHI site to clone the hopPtoK gene. The partial avrRpt2 gene with the N terminal 40 codons deleted was amplified using standard PCR procedures and cloned into pMOD (Madison, Wis.). After confirmation by sequence analysis, it was cloned into the KpnI and SalI sites of the broad-host-plasmid pLK, resulting in pΔavrRpt2. DNA fragments spanning 200 bp upstream of the Hrp boxes and the complete ORFs for hopPtoK was cloned into pΔavrRpt2 to produce phopPtoK-ΔavrRpt2. Additionally, the full-length hopPtoK was cloned using PCR into pLK to generate phopPtoK. Each construct was introduced in *P. s. phaseolicola* 3121 by electroporation. Bacterial strains in 10 mM $MgCl_2$ at a cell density of $10^8$ cfu/ml were infiltrated into *A. thaliana* Col-0 plants with a needleless syringe. Plant responses were documented 18 hours postinoculation.

Figure 2B:
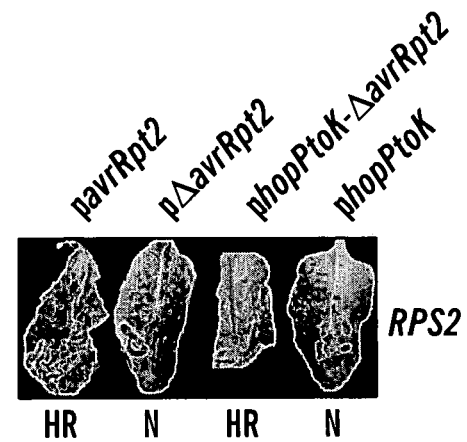

The AvrRpt2 translocation assay was used to test whether the DC3000 ORF that is similar to AvrRps4 (Hinsch & Staskawicz, *Mol. Plant-Microbe Interact.* 9:55–61 (1996), which is hereby incorporated by reference in its entirety) was translocated into *Arabidopsis* plant cells (Mudgett et al., *Proc. Natl. Acad. Sci. USA* 97:13324–13329 (2000); Guttman & Greenberg, *Mol. Plant-Microbe Interact.* 14:145–155) (2001), each of which is hereby incorporated by reference in its entirety). *P. s. phaseolicola* carrying a broad-host-range plasmid expressing the AvrRps4 homolog fused to the Avr domain of AvrRpt2 (but lacking the secretion signals of AvrRpt2) elicited an RPS2-dependent HR on *A. thaliana* Col-0 (FIG. 2B), indicating that the amino terminus of the AvrRps4 homolog supplied sufficient information to direct translocation of the fusion protein into plant cells. Consequently, the AvrRps4 homolog was renamed HopPtoK. *P. s. phaseolicola* expressing HopPtoK did not elicit an HR, indicating that although translocated into host cells, HopPtoK is probably not recognized by the RPS4 protein present in *A. thaliana* Col-0, in contrast to its *P. s. pisi* 151 homolog (Hinsch & Staskawicz, *Mol. Plant-Microbe Interact.* 9:55–61 (1996), which is hereby incorporated by reference in its entirety).

Example 4

Determining Cytotoxicity of Effector in Yeast

Effector proteins of the present invention will be cloned into pFLAG-CTC (Kodak) to generate an in-frame fusion with the FLAG epitope, which will permit monitoring of protein production with anti-FLAG monoclonal antibodies. The FLAG-tagged genes will then be cloned under the control of the GAL1 promoter in the yeast shuttle vector p415GAL1 (Mumberg et al., 1994). These regulatable promoters of *Saccharomyces cerevisiae* will allow comparison of transcriptional activity and heterologous expression. The recombinant plasmids will be transformed into uracil auxotrophic yeast strains FY833/4, then selected for growth on SC-Ura (synthetic complete medium lacking uracil) based on the presence of the URA3 gene on the plasmid. The transformants will then be streaked onto SC-Ura medium plates containing either 2% galactose (which will induce expression of the effector proteins) or 2% glucose. The presence or absence of growth on the plates supplemented with 2% galactose will be observed. If no growth is observed on 2% galactose (but growth is observed in the 2% glucose control), this result will suggest that the effector protein is having a cytotoxic effect on the transformed yeast. Empty vector controls will also be used. FLAG-tagged nontoxic Avr proteins will be used to confirm that the recombinant effector genes were differentially expressed, as expected, on plates containing galactose. To further confirm the results, albeit at lower expression levels, the recombinant effector gene will be recloned into p416GALS, which expresses foreign genes at a substantially lower level than p415GAL1.

Example 5

Determining Cytotoxicity of Effector in Plants

To determine whether effector proteins induce cell death on tobacco leaves, a transformation system that delivers the effector gene on T-DNA of *Agrobacterium tumefaciens* will be used (Rossi et al., *Plant Mol. Biol. Reporter* 11:220–229 (1993); van den Ackerveken et al., *Cell* 87:1307–1316 (1996), each of which is hereby incorporated by reference in its entirety). This delivery system works better than biolistics for transiently transforming whole plant leaves. For these experiments, vector pTA7002, kindly provided by Nam-Hai Chua and his colleagues at Rockefeller University, will be used. The unique property of this vector is that it contains an inducible expression system that uses the regulatory mechanism of the glucocorticoid receptor (Picard et al., *Cell* 54:1073–1080 (1988); Aoyama and Chua, *Plant J.* 11(3):605–612 (1997); McNellis et al., *Plant J.* 14(2): 247–257 (1998), each of which is hereby incorporated by reference in its entirety). pTA7002 encodes a chimeric transcription factor consisting of the DNA-binding domain of GAL4, the transactivating domain of the herpes viral protein VP16, and the receptor domain of the rat glucocorticoid receptor. Also contained on this vector is a promoter containing GAL4 upstream activating sequences (UAS) upstream of a multiple cloning site. Thus, any gene cloned downstream of the promoter containing the GAL4-UAS can be induced by glucocorticoids, of which a synthetic glucocorticoid, dexamethasone (DEX), is available commercially. Effector proteins of the present invention will be PCR-cloned downstream of the GAL4-UAS. Thereafter, plant leaves from several different test plants will be infiltrated with *Argrobacterium* carrying recombinant pTA7002 carrying the effector ORF and after 48 hours these plants will be sprayed with DEX to induce expression of the effectors.

Tobacco (*Nicotiana tabacum*) and tomato (*Lycopersicon esculentum*) will be grown under greenhouse conditions and then maintained at 25° C. with daylight and supplemental halide illumination for HR and virulence assays. Bacteria will be grown overnight on King's medium B agar supplemented with appropriate antibiotics, suspended in 5 mM MES pH 5.6, and then infiltrated with a needleless syringe into the leaves of test plants at $10^8$ cfu/ml for HR assays and $10^4$ cfu/ml for pathogenicity assays (Charkowski et al., *J. Bacteriol.* 180:5211–5217 (1998), which is hereby incorporated by reference in its entirety). All assays will be repeated at least four times on leaves from different plants. Bacterial growth in tomato leaves will be assayed by excising disks from infiltrated areas with a cork borer, comminuting the tissue in 0.5 ml of 5 mM MES, pH 5.6, with an appropriate pestle, and then dilution plating the homogenate on King's medium B agar with 50 μg/ml rifampicin and 2 μg/ml cycloheximide to determine bacterial populations. The mean and SD from three leaf samples will be determined for each time point.

Plant leaves will be examined to determine the response of plant tissue to the expression of the effector proteins. In particular, plant tissues will be examined for tissue necrosis indicative of a hypersensitive response.

Although the invention has been described in detail for the purposes of illustration, it is understood that such detail is solely for that purpose, and variations can be made therein by those skilled in the art without departing from the spirit and scope of the invention which is defined by the following claims.

What is claimed:

1. An isolated nucleic acid molecule comprising a nucleotide sequence which
encodes a protein or polypeptide comprising SEQ ID No: 12.

2. The nucleic acid molecule according to claim 1, wherein the nucleic acid molecule comprises the nucleotide sequence according to SEQ ID No: 11.

3. The nucleic acid molecule according to claim 1, wherein the nucleic acid molecule is DNA.

4. An expression system comprising a vector into which is inserted the nucleic acid molecule according to claim 3.

5. The expression system according to claim 4, wherein the nucleic acid molecule is inserted in sense orientation relative to a promoter.

6. A host cell comprising the nucleic acid molecule according to claim 3.

7. The host cell according to claim 6, wherein the host cell is a bacterial cell or a plant cell.

8. The host cell according to claim 7, wherein the bacterial cell is *Agrobacterium*.

9. A transgenic plant comprising the nucleic acid molecule according to claim 3.

10. A method of making a transgenic plant cell comprising:
providing nucleic acid molecule according to claim 3, and
transforming a plant cell with the nucleic acid molecule, whereby the nucleic acid molecule is expressed by the transformed plant cell.

11. A method of making a transgenic plant comprising:
transforming a plant cell with the nucleic acid molecule according to claim 3, whereby the nucleic acid molecule is expressed by the transformed plant cell, and
regenerating a transgenic plant from the transformed plant cell.

12. A method of making a plant hypersusceptible to colonization by nonpathogenic bacteria, said method comprising:
transforming a plant cell with the nucleic acid molecule of claim 3, and
regenerating a transgenic plant from the transformed plant cell,
wherein a transgenic plant expresses a protein or polopeptide encoded by a nucleic acid molecule, thereby rendering the transgenic plant hypersusceptible to colonization by nonpathogenic bacteria.

* * * * *

```
                        SEQUENCE LISTING

<160> NUMBER OF SEQ ID NOS: 36

<210> SEQ ID NO 1
<211> LENGTH: 1155
<212> TYPE: DNA
<213> ORGANISM: Pseudomonas syringae

<400> SEQUENCE: 1
atgaaaatac ataacgctgg cctaacccca cctttgccgg gcatttcgaa tggaaacgtt      60
ggaaaggcgg cgcaatcatc aataactcaa ccgcagagcc agcaaggctc ttatggcttg     120
ccaccagaaa gctctgagac tcgccctgat agggcgcgtg cgaactatcc atattcatca     180
gtacaaacac ggttgccgcc cgttgcgtct gctgggaaac cgctgcctga tacaccatct     240
tctttgcccg gctacttact gttgcgaagg ctggaccatc gccctgtgga tcaggaaggt     300
accaaaagtc tgatcccggc agacaaggct gtggctgaag cgcgccgtgc attgcccttt     360
ggaagaggca atattgatgt ggatgcgcaa cttccaatc tggaaagtgg agcccgcacc     420
cttgcagcaa ggtgcttgag aaaagatgcc gaggccgccg tcatgagcc tatgcctgcg     480 aatgagccga tgaactggca tgttcttgtt gcgatgtcag gccaggtgtt cggcgcgggc     540
aactgtggcg aacatgctcg tatagcgagc ttcgcctatg gagctttggc ccaggaaaac     600
ggacgatctg aatatgaaaa catctacttg gctgcatcga ctgaggaaga tcatgtgtgg     660
gctgaaaccg acgaatccca gtctggcacc tcaacgattg tcatggatcc gtggtcaaat     720
ggttcagcca tatttgcgga ggacagtagg tttgcgaaaa atcgaaatgc tgtagagcgt     780
acggatacgt ttaatctttc aaccgcagcc gaagcgggca aaattacgcg tgagacagcc     840
gagaaggctt tgacgcaggt cacaacccga ttgcagaaac gcctggcgga tcagcaggag     900
caagtctcgc ccatcaaaag tggtcgctat cgaccagaaa atcggtact tgatgatgca     960 tttgtccgca gagtgagcga caagttgacc tcccctgatt tgcggcgtgc actacaggta    1020
gatattgaag cggtcggagt cgcaatgtcg ctcggcacca agggcgtcaa ggacgctact    1080
cgacaagccc gacctttggt tgagcttgca gtgaaggtcg cctctcctca aggcttggcg    1140
agacgagatg tctga                                                     1155

<210> SEQ ID NO 2
<211> LENGTH: 384
<212> TYPE: PRT
<213> ORGANISM: Pseudomonas syringae

<400> SEQUENCE: 2

Met Lys Ile His Asn Ala Gly Leu Thr Pro Pro Leu Pro Gly Ile Ser
  1               5                  10                  15

Asn Gly Asn Val Gly Lys Ala Ala Gln Ser Ser Ile Thr Gln Pro Gln
             20                  25                  30

Ser Gln Gln Gly Ser Tyr Gly Leu Pro Pro Glu Ser Ser Glu Thr Arg
         35                  40                  45

Pro Asp Arg Ala Arg Ala Asn Tyr Pro Tyr Ser Ser Val Gln Thr Arg
     50                  55                  60

Leu Pro Pro Val Ala Ser Ala Gly Lys Pro Leu Pro Asp Thr Pro Ser
 65                  70                  75                  80
```

```
Ser Leu Pro Gly Tyr Leu Leu Arg Arg Leu Asp His Arg Pro Val
             85                  90                  95

Asp Gln Glu Gly Thr Lys Ser Leu Ile Pro Asp Lys Ala Val Ala
            100                 105                 110

Glu Ala Arg Arg Ala Leu Pro Phe Gly Arg Gly Asn Ile Asp Val Asp
            115                 120                 125

Ala Gln Leu Ser Asn Leu Glu Ser Gly Ala Arg Thr Leu Ala Ala Arg
        130                 135                 140

Cys Leu Arg Lys Asp Ala Glu Ala Ala Gly His Glu Pro Met Pro Ala
145                 150                 155                 160

Asn Glu Pro Met Asn Trp His Val Leu Val Ala Met Ser Gly Gln Val
                165                 170                 175

Phe Gly Ala Gly Asn Cys Gly Glu His Ala Arg Ile Ala Ser Phe Ala
            180                 185                 190

Tyr Gly Ala Leu Ala Gln Glu Asn Gly Arg Ser Glu Tyr Glu Asn Ile
        195                 200                 205

Tyr Leu Ala Ala Ser Thr Glu Glu Asp His Val Trp Ala Glu Thr Asp
    210                 215                 220

Glu Ser Gln Ser Gly Thr Ser Thr Ile Val Met Asp Pro Trp Ser Asn
225                 230                 235                 240

Gly Ser Ala Ile Phe Ala Glu Asp Ser Arg Phe Ala Lys Asn Arg Asn
            245                 250                 255

Ala Val Glu Arg Thr Asp Thr Phe Asn Leu Ser Thr Ala Ala Glu Ala
            260                 265                 270

Gly Lys Ile Thr Arg Glu Thr Ala Glu Lys Ala Leu Thr Gln Val Thr
        275                 280                 285

Thr Arg Leu Gln Lys Arg Leu Ala Asp Gln Gln Glu Gln Val Ser Pro
    290                 295                 300

Ile Lys Ser Gly Arg Tyr Arg Pro Glu Lys Ser Val Leu Asp Asp Ala
305                 310                 315                 320

Phe Val Arg Arg Val Ser Asp Lys Leu Thr Ser Pro Asp Leu Arg Arg
            325                 330                 335

Ala Leu Gln Val Asp Ile Glu Ala Val Gly Val Ala Met Ser Leu Gly
            340                 345                 350

Thr Lys Gly Val Lys Asp Ala Thr Arg Gln Ala Arg Pro Leu Val Glu
        355                 360                 365

Leu Ala Val Lys Val Ala Ser Pro Gln Gly Leu Ala Arg Arg Asp Val
    370                 375                 380

<210> SEQ ID NO 3
<211> LENGTH: 1017
<212> TYPE: DNA
<213> ORGANISM: Pseudomonas syringae

<400> SEQUENCE: 3
atgaatcgca tttcaaccag ctcagtaaat tccagcttca attacacggc ccctacggag    60
gaagcgcaaa accgcttcgc ctcagcgccc gacaattccc ctctagttgt caccacaaca   120
tctatcgccc aagcgtcgga agggctacaa aggccggggg caacgctaag catgcaggcc   180
cagcgactgc gccaattgat ggggagcccg tctgagcagt gccggaggga cacaatgtta   240
gctaaagctt ttgatgctca acgcctaaac attaacactc aagcaggctc ttccaacagc   300
ccacacttga acgctctcaa cacgctccaa caacgacact tcaaacctgc ggctggtggg   360
ctagaaatcc cagttacatc caactcctta ttgggcggtg gcaggcaagt ctatcaaatt   420
```

-continued

```
ggctcatcgt cacgcgagct aagccaccga ccggtcaatg atcaggaccg cgcgcccttc    480
agggcgcttg agcggctgca cgccgagttg tttagaggtg ggccgattga gtttgtgcct    540
agaggcagca acgtgttggc ctcaaacgtg agggatgtcg acatggacga gttcgatgtc    600
atcaactcta agacggctg ccaaggcatt ggcaccactg gcctgggacc ctgcattgca    660
gtgtgtgcaa gaggcatgga tagagaaggg cttccggtgc tgggtgtcta tcaccacagt    720
ggtatcggct caccagagga taccatggct actcttgatc aagcgatgcg cgataaaggt    780
gctttgcaaa tcaaatactc cctggtaggc ggcatgatca tgcctaaaga ggaagaggct    840
ggcagctatg acgacgagca aagctttttg cattgaaaag gcagttattc aatcgaaggg    900
gcgcgcttgc atgtatccga aggcgaagag gacgtgcata ccggcgagga caacagtgtc    960
aatgttctgc tgatgcctga ccgcgttctg tacggtcgcg acacgctcta ctgctga     1017
```

<210> SEQ ID NO 4
<211> LENGTH: 338
<212> TYPE: PRT
<213> ORGANISM: Pseudomonas syringae

<400> SEQUENCE: 4

```
Met Asn Arg Ile Ser Thr Ser Ser Val Asn Ser Ser Phe Asn Tyr Thr
  1               5                  10                  15

Ala Pro Thr Glu Glu Ala Gln Asn Arg Phe Ala Ser Ala Pro Asp Asn
                 20                  25                  30

Ser Pro Leu Val Val Thr Thr Thr Ser Ile Ala Gln Ala Ser Glu Gly
             35                  40                  45

Leu Gln Arg Pro Gly Ala Thr Leu Ser Met Gln Ala Gln Arg Leu Arg
         50                  55                  60

Gln Leu Met Gly Ser Pro Ser Glu Gln Cys Arg Arg Asp Thr Met Leu
 65                  70                  75                  80

Ala Lys Ala Phe Asp Ala Gln Arg Leu Asn Ile Asn Thr Gln Ala Gly
                 85                  90                  95

Ser Ser Asn Ser Pro His Leu Asn Ala Leu Asn Thr Leu Gln Gln Arg
            100                 105                 110

His Phe Lys Pro Ala Ala Gly Gly Leu Glu Ile Pro Val Thr Ser Asn
        115                 120                 125

Ser Leu Leu Gly Gly Gly Arg Gln Val Tyr Gln Ile Gly Ser Ser Ser
    130                 135                 140

Arg Glu Leu Ser His Arg Pro Val Asn Asp Gln Asp Arg Ala Pro Phe
145                 150                 155                 160

Arg Ala Leu Glu Arg Leu His Ala Glu Leu Phe Arg Gly Gly Pro Ile
                165                 170                 175

Glu Phe Val Pro Arg Gly Ser Asn Val Leu Ala Ser Asn Val Arg Asp
            180                 185                 190

Val Asp Met Asp Glu Phe Asp Val Ile Asn Ser Lys Asp Gly Cys Gln
        195                 200                 205

Gly Ile Gly Thr Thr Gly Leu Gly Pro Cys Ile Ala Val Cys Ala Arg
    210                 215                 220

Gly Met Asp Arg Glu Gly Leu Pro Val Leu Gly Val Tyr His His Ser
225                 230                 235                 240

Gly Ile Gly Ser Pro Glu Asp Thr Met Ala Thr Leu Asp Gln Ala Met
                245                 250                 255

Arg Asp Lys Gly Ala Leu Gln Ile Lys Tyr Ser Leu Val Gly Gly Met
            260                 265                 270
```

```
Ile Met Pro Lys Glu Glu Ala Gly Ser Tyr Asp Asp Glu Gln Ser
        275                 280                 285

Phe Leu Ala Leu Lys Gly Ser Tyr Ser Ile Glu Gly Ala Arg Leu His
        290                 295                 300

Val Ser Glu Gly Glu Glu Asp Val His Thr Gly Glu Asp Asn Ser Val
305                 310                 315                 320

Asn Val Leu Leu Met Pro Asp Arg Val Leu Tyr Gly Arg Asp Thr Leu
                325                 330                 335

Tyr Cys

<210> SEQ ID NO 5
<211> LENGTH: 396
<212> TYPE: DNA
<213> ORGANISM: Pseudomonas syringae

<400> SEQUENCE: 5
atgaaaaacg catttgacct gcttgtggaa gggctggcta aggactacaa catgccgccc      60
ttgcctgaca gaaacatat cgatgaagtc tattgctttg agtttcaaag tggtatgaac     120
gtaaaagtat accaagacga atttcgctgg gtatatttca ccgctgacgt tgggacattt    180
caagatagca gtattgacac attaaactac gcgctccagc tgaacaactt tagccttaga    240
aaacctttcc tgaccttcgg aatgacgaag gagaaaaatg gtgtattgca tacacgcacc    300 ccccttgattg aggtagacaa cgtgcaaatg cgcaggatat ttgaggagct tataggcgtg    360
gcaggtgaaa tcagaaaaac actaaaactc aaatag                               396

<210> SEQ ID NO 6
<211> LENGTH: 131
<212> TYPE: PRT
<213> ORGANISM: Pseudomonas syringae

<400> SEQUENCE: 6

Met Lys Asn Ala Phe Asp Leu Leu Val Glu Gly Leu Ala Lys Asp Tyr
 1               5                  10                  15

Asn Met Pro Pro Leu Pro Asp Lys Lys His Ile Asp Glu Val Tyr Cys
                20                  25                  30

Phe Glu Phe Gln Ser Gly Met Asn Val Lys Val Tyr Gln Asp Glu Phe
            35                  40                  45

Arg Trp Val Tyr Phe Thr Ala Asp Val Gly Thr Phe Gln Asp Ser Ser
        50                  55                  60

Ile Asp Thr Leu Asn Tyr Ala Leu Gln Leu Asn Asn Phe Ser Leu Arg
 65                 70                  75                  80

Lys Pro Phe Leu Thr Phe Gly Met Thr Lys Lys Asn Gly Val Leu
                85                  90                  95

His Thr Arg Thr Pro Leu Ile Glu Val Asp Asn Val Gln Met Arg Arg
                100                 105                 110

Ile Phe Glu Glu Leu Ile Gly Val Ala Gly Glu Ile Arg Lys Thr Leu
            115                 120                 125

Lys Leu Lys
        130

<210> SEQ ID NO 7
<211> LENGTH: 579
<212> TYPE: DNA
<213> ORGANISM: Pseudomonas syringae

<400> SEQUENCE: 7
```

```
gtgtatagcc catcccatac acaacgaata acttcagctc cctctacatc cactcatgtt      60
ggtggagata cactgacatc cattcatcag ctttcgcata gtcagagaga gcagtttctg     120
aacatgcatg atccaatgag agtaatggga cttgaccatg ataccgagct tttcagaacg     180
acggatagtc gctatataaa aaacgataaa ctcgcgggca atccacaatc catggcgagt     240
atccttatgc atgaagaact gcgcccaat cgttttgcca gccatacagg tgcccaacca      300
cacgaagcaa gggcgtacgt tccgaaaaga ataaaagcca ccgatctagg agttccatca     360
ctgaacgtaa tgactggctc gctagcgcga gacggaatta gagcttatga tcacatgagt     420
gataatcagg tctctgtcaa aatgcgactg ggagattttc tcgaaagggg tggcaaggtc     480
tatgccgacg cttcgtctgt agctgacgat ggggaaacat cacaagctct gattgtcaca     540
ttgcccaaag gacagaaagt gccggtcgaa aggtctga                             579
```

<210> SEQ ID NO 8  
<211> LENGTH: 192  
<212> TYPE: PRT  
<213> ORGANISM: Pseudomonas syringae

<400> SEQUENCE: 8

```
Val Tyr Ser Pro Ser His Thr Gln Arg Ile Thr Ser Ala Pro Ser Thr
 1               5                  10                  15

Ser Thr His Val Gly Gly Asp Thr Leu Thr Ser Ile His Gln Leu Ser
                20                  25                  30

His Ser Gln Arg Glu Gln Phe Leu Asn Met His Asp Pro Met Arg Val
            35                  40                  45

Met Gly Leu Asp His Asp Thr Glu Leu Phe Arg Thr Thr Asp Ser Arg
        50                  55                  60

Tyr Ile Lys Asn Asp Lys Leu Ala Gly Asn Pro Gln Ser Met Ala Ser
 65                  70                  75                  80

Ile Leu Met His Glu Glu Leu Arg Pro Asn Arg Phe Ala Ser His Thr
                85                  90                  95

Gly Ala Gln Pro His Glu Ala Arg Ala Tyr Val Pro Lys Arg Ile Lys
            100                 105                 110

Ala Thr Asp Leu Gly Val Pro Ser Leu Asn Val Met Thr Gly Ser Leu
        115                 120                 125

Ala Arg Asp Gly Ile Arg Ala Tyr Asp His Met Ser Asp Asn Gln Val
    130                 135                 140

Ser Val Lys Met Arg Leu Gly Asp Phe Leu Glu Arg Gly Gly Lys Val
145                 150                 155                 160

Tyr Ala Asp Ala Ser Ser Val Ala Asp Asp Gly Glu Thr Ser Gln Ala
                165                 170                 175

Leu Ile Val Thr Leu Pro Lys Gly Gln Lys Val Pro Val Glu Arg Val
            180                 185                 190
```

<210> SEQ ID NO 9  
<211> LENGTH: 2118  
<212> TYPE: DNA  
<213> ORGANISM: Pseudomonas syringae

<400> SEQUENCE: 9

```
atgaatcctc tacgatctat tcaacacaac attgcaactc ccccaatcag tggcggtcag      60
ccattagacg cggtgggccc tcaggccag caatcccatc ctaaaaggat ttcaccttct      120
caattgagcc aaagcgctca ccaggctcta gaacgccttt cagctaatgc cgaacaccaa     180
```

-continued

```
cgccttgcat cactggtacg caacgctctg caggatggca catttcaatt tcaatccagt      240
aaccacacgc aagtaaccta taaagcgtca atctgtctgc cagctgacac cgataccgtg      300
agaaccgacc acttgattaa taacgagctg acggttcagg cccgattaaa tgatcaatcg      360
gagtacgaca tcgtcagcgc acatttgcat ggctcttcga aagccatatc cttcgacgta      420
cccagccccc cgcccgcaca tggttcagca tcttctgtct tgagtgaacg acccatcta      480 ggtatgagtc gcgttctctc acaagatgca gtagacagca gtagcctgga aactccgtta      540
ctgagctcgc cagaccattc tcgtccgcca tcacagccaa agcccgtgca tatcgggtcg      600
gtccgcaggg actctggtag ccttgtttcc gataacccgg tagtgcaggc cctgctatcg      660
tttgcgcagg ccgaccaggc atttccacca caggccgcga gcattgccgg ggtccagctg      720
gaaatgcggc cacgtcggga tattgagaaa gcacttgagg aattcaaagg cgccttcacg      780
gtggtgaagg cgcaactgat gtccggtgcc aactcgtcgg agcgtgtaga tgaggatgtc      840
aacgcagaca tccatatccc cttattgctc aaggccatcg agcgggggc tgcggcattt      900 ggtccaaacg catcaatcgg ccagaatagc gcgaaagcgt ttctcgcctc atgtgctccc      960
aagatcacgt ccaatgacga tgtcctctcc gagttcatca accagaaact caaggggggac     1020 gacgatcttc aggttcgcct gggcgcacag gaattgttgc atgtagccac caagaaggaa     1080
ttccagctcg gcggtctagc cggcagcatc ggggtcagca gcatactcgg ctcggcatgg     1140
gagcttggcg cttctgagct gttgaaaaat gccatcttcg gcaaaaattt ctcaccgagc     1200
caatatgccc tgcaattggc tggaatcgat tcagtgcctc ctttgattat cgagtccatg     1260
gacaccatgt gcgtacttgc catcatcaag ggcatgaagg gtgaggagtg gtccatgagc     1320
gatctacttc ccaaggcgtt gaaggccggt gctatttcct cggtggtgtc attccccaat     1380
aatgttttgc agtatgcagg tttcaaatcc agagtcggcg atcttgcggc aaactcagtg     1440
acaactgaag cggccatctt tggcgccgcc tccggtattc cacccgaggt caaggaaagt     1500
gaagagctga tgcgtgctgg cttattccag agcatgaagg acggcgtgat ggctcattca     1560
ggcgaggggg tggacaccaa aaaaacgatt gagcggatga cgcgccatgc gctggatatc     1620
gctccgggcg aaagcaccgc tgtcaagtcc atggggctgg catcgattgt cgggatgatt     1680
ccactgattg ccagcaacaa ggcaaccggg ctgctgtcgg aacaggtact gcgtattttc     1740
cggagcgccg tcttcaatcc aatcgaagcc atcgctctga acgcgttggc gcttggcggg     1800
cgtgtcaacg ttcccgggct atttgattcc gacaatgcca agcatgcacg cgtggtacaa     1860
accatccttg cgcgggccag ccagcacatg gaagctggac accgtgacat ttccgcagag     1920
gagctacatc aaatgctggc tccccggagc gagttcctgc gccatgtggg atctgcgatt     1980
gtcaacggca tgaatgccag cttttgaggca attcccgccc tggttcggaa gcttggatat     2040
ggtgaggctc cattggccga acgtattccg tatcaagacc tggctgtgcc cgacacgtcg     2100
cggcagcccg caccctga                                                    2118
```

<210> SEQ ID NO 10
<211> LENGTH: 705
<212> TYPE: PRT
<213> ORGANISM: Pseudomonas syringae

<400> SEQUENCE: 10

Met Asn Pro Leu Arg Ser Ile Gln His Asn Ile Ala Thr Pro Pro Ile
 1               5                  10                  15

Ser Gly Gly Gln Pro Leu Asp Ala Val Gly Pro Gln Ala Gln Gln Ser
            20                  25                  30

```
His Pro Lys Arg Ile Ser Pro Ser Gln Leu Ser Gln Ser Ala His Gln
         35                  40                  45

Ala Leu Glu Arg Leu Ser Ala Asn Ala Glu His Gln Arg Leu Ala Ser
 50                  55                  60

Leu Val Arg Asn Ala Leu Gln Asp Gly Thr Phe Gln Phe Gln Ser Ser
 65                  70                  75                  80

Asn His Thr Gln Val Thr Tyr Lys Ala Ser Ile Cys Leu Pro Ala Asp
                 85                  90                  95

Thr Asp Thr Val Arg Thr Asp His Leu Ile Asn Asn Glu Leu Thr Val
                100                 105                 110

Gln Ala Arg Leu Asn Asp Gln Ser Glu Tyr Asp Ile Val Ser Ala His
            115                 120                 125

Leu His Gly Ser Ser Lys Ala Ile Ser Phe Asp Val Pro Ser Pro Pro
        130                 135                 140

Pro Ala His Gly Ser Ala Ser Ser Val Leu Ser Glu Arg Thr His Leu
145                 150                 155                 160

Gly Met Ser Arg Val Leu Ser Gln Asp Ala Val Asp Ser Ser Ser Leu
                165                 170                 175

Glu Thr Pro Leu Leu Ser Ser Pro Asp His Ser Arg Pro Pro Ser Gln
                180                 185                 190

Pro Lys Pro Val His Ile Gly Ser Val Arg Arg Asp Ser Gly Ser Leu
        195                 200                 205

Val Ser Asp Asn Pro Val Val Gln Ala Leu Leu Ser Phe Ala Gln Ala
210                 215                 220

Asp Gln Ala Phe Pro Pro Gln Ala Ala Ser Ile Ala Gly Val Gln Leu
225                 230                 235                 240

Glu Met Arg Pro Arg Arg Asp Ile Glu Lys Ala Leu Glu Glu Phe Lys
                245                 250                 255

Gly Ala Phe Thr Val Val Lys Ala Gln Leu Met Ser Gly Ala Asn Ser
                260                 265                 270

Ser Glu Arg Val Asp Glu Asp Val Asn Ala Asp Ile His Ile Pro Leu
        275                 280                 285

Leu Leu Lys Ala Ile Glu Arg Gly Ala Ala Ala Phe Gly Pro Asn Ala
290                 295                 300

Ser Ile Gly Gln Asn Ser Ala Lys Ala Phe Leu Ala Ser Cys Ala Pro
305                 310                 315                 320

Lys Ile Thr Ser Asn Asp Val Leu Ser Glu Phe Ile Asn Gln Lys
                325                 330                 335

Leu Lys Gly Asp Asp Asp Leu Gln Val Arg Leu Gly Ala Gln Glu Leu
            340                 345                 350

Leu His Val Ala Thr Lys Lys Glu Phe Gln Leu Gly Leu Ala Gly
        355                 360                 365

Ser Ile Gly Val Ser Ser Ile Leu Gly Ser Ala Trp Glu Leu Gly Ala
    370                 375                 380

Ser Glu Leu Leu Lys Asn Ala Ile Phe Gly Lys Asn Phe Ser Pro Ser
385                 390                 395                 400

Gln Tyr Ala Leu Gln Leu Ala Gly Ile Asp Ser Val Pro Pro Leu Ile
                405                 410                 415

Ile Glu Ser Met Asp Thr Met Cys Val Leu Ala Ile Ile Lys Gly Met
            420                 425                 430

Lys Gly Glu Glu Trp Ser Met Ser Asp Leu Leu Pro Lys Ala Leu Lys
435                 440                 445
```

-continued

Ala Gly Ala Ile Ser Ser Val Ser Phe Pro Asn Asn Val Leu Gln
    450                 455                 460

Tyr Ala Gly Phe Lys Ser Arg Val Gly Asp Leu Ala Ala Asn Ser Val
465                 470                 475                 480

Thr Thr Glu Ala Ala Ile Phe Gly Ala Ala Ser Gly Ile Pro Pro Glu
            485                 490                 495

Val Lys Glu Ser Glu Glu Leu Met Arg Ala Gly Leu Phe Gln Ser Met
            500                 505                 510

Lys Asp Gly Val Met Ala His Ser Gly Glu Gly Val Asp Thr Lys Lys
        515                 520                 525

Thr Ile Glu Arg Met Thr Arg His Ala Leu Asp Ile Ala Pro Gly Glu
    530                 535                 540

Ser Thr Ala Val Lys Ser Met Gly Leu Ala Ser Ile Val Gly Met Ile
545                 550                 555                 560

Pro Leu Ile Ala Ser Asn Lys Ala Thr Gly Leu Leu Ser Glu Gln Val
            565                 570                 575

Leu Arg Ile Phe Arg Ser Ala Val Phe Asn Pro Ile Glu Ala Ile Ala
            580                 585                 590

Leu Asn Ala Leu Ala Leu Gly Gly Arg Val Asn Val Pro Gly Leu Phe
        595                 600                 605

Asp Ser Asp Asn Ala Lys His Ala Arg Val Val Gln Thr Ile Leu Ala
    610                 615                 620

Arg Ala Ser Gln His Met Glu Ala Gly Asp Arg Asp Ile Ser Ala Glu
625                 630                 635                 640

Glu Leu His Gln Met Leu Ala Pro Arg Ser Glu Phe Leu Arg His Val
            645                 650                 655

Gly Ser Ala Ile Val Asn Gly Met Asn Ala Ser Phe Glu Ala Ile Pro
            660                 665                 670

Ala Leu Val Arg Lys Leu Gly Tyr Gly Glu Ala Pro Leu Ala Glu Arg
        675                 680                 685

Ile Pro Tyr Gln Asp Leu Ala Val Pro Asp Thr Ser Arg Gln Pro Ala
    690                 695                 700

Pro
705

<210> SEQ ID NO 11
<211> LENGTH: 1407
<212> TYPE: DNA
<213> ORGANISM: Pseudomonas syringae

<400> SEQUENCE: 11
atgaatcccc tgcaacctat tcagcacagc attacaaatt cccaaatgag tggtggtcag      60
caattagagg cggagggctc tcaggcccac aattcctatt ccatcctga caggatttcg     120 ctttcccaat tgagccaaag cgctcaccta gctctagatc cctttcaac tcagcctaat     180 accgatcacc aacgcgttgc atcactggta cgcaacgctg tgcaggacgg taagttccaa     240
cttcaatcca gtaacgacac gcaagtaacc tataaaactt cagtctgtcc gccagctaac     300
gccgacacca tggggccgc ccacttaatt aataacgagc tgacggttca ggcccgatta     360
aatgatcaac ttgagtacga catcgtcagc gctcatttgt atggcccttc ggaagccata     420
tccatcgatg catccagtcc tccctcggcc aacgatctag cgtcctctgg cttgagcgaa     480
cgtacgcatc taggtatgaa tcgtgtcctc ttacgctacg cggtgcccc tcgggaaacc     540 gaagaccaat gtgttatggt gatcgacaaa atgcccccc ccaaacacgg caaaatgtct     600

-continued

```
ttcttccgta ccactaatga cttgagcaaa ctgcctttgg gaatggagac gggcgggttg    660
tccgacctga aattggctgg ttgtgaacgt atttcttccg tcgagcaggt gaagagtatc    720
cgcgcagcgc ttggaggcgg gccgctcacc gtactagatc tgcgcgaaga atctcatgcg    780
attgtcaacg gtttgcctat caccttacgt ggcccgatgg attgggccaa cgccggccta    840
tcccaggttg acgagcggc acgtgaaagt gccatgatta cagaactgaa gcgcactaag    900
tctttaacgt tggtcgatgc caattatgta aaggtaaaa aaagtaatcc tcaaacgaca    960
gaactgaaaa atttgaatgt ccggagcgag cgagaagtcg ttacagaggc cggcgcgacc   1020
tatcgccgcg tggccattac cgaccataac aggcctagtc cggaagcgac cgacgagcta   1080
gtagacatca tgcgccactg cctgcaggca atgagtcgc tagttgtgca ctgtaacggc    1140
ggtcggggcc gtactaccac ggctatgata atggtcgaca tgcttaagaa cgctcgtaac   1200
cattccgcag aaaccctcat cacgcgtatg gccaagctaa gctatgacta caacatgacg   1260
gatctaggca gcatttctgc actcaagcgg ccattcctag aggacagact aaaatttctg   1320
caggcctttc acgactatgc ccgcaacaac ccaagcggat tatctcttaa ttggacacag   1380
tggcgcgcaa aaatagcgtt agaatga                                       1407
```

<210> SEQ ID NO 12
<211> LENGTH: 468
<212> TYPE: PRT
<213> ORGANISM: Pseudomonas syringae

<400> SEQUENCE: 12

```
Met Asn Pro Leu Gln Pro Ile Gln His Ser Ile Thr Asn Ser Gln Met
  1               5                  10                  15

Ser Gly Gly Gln Gln Leu Glu Ala Glu Gly Ser Gln Ala His Asn Ser
                 20                  25                  30

Tyr Ser His Pro Asp Arg Ile Ser Leu Ser Gln Leu Ser Gln Ser Ala
             35                  40                  45

His Leu Ala Leu Asp His Leu Ser Thr Gln Pro Asn Thr Asp His Gln
         50                  55                  60

Arg Val Ala Ser Leu Val Arg Asn Ala Val Gln Asp Gly Lys Phe Gln
 65                  70                  75                  80

Leu Gln Ser Ser Asn Asp Thr Gln Val Thr Tyr Lys Thr Ser Val Cys
                 85                  90                  95

Pro Pro Ala Asn Ala Asp Thr Met Gly Ala Ala His Leu Ile Asn Asn
            100                 105                 110

Glu Leu Thr Val Gln Ala Arg Leu Asn Asp Gln Leu Glu Tyr Asp Ile
        115                 120                 125

Val Ser Ala His Leu Tyr Gly Pro Ser Glu Ala Ile Ser Ile Asp Ala
    130                 135                 140

Ser Ser Pro Pro Ser Ala Asn Asp Leu Ala Ser Ser Gly Leu Ser Glu
145                 150                 155                 160

Arg Thr His Leu Gly Met Asn Arg Val Leu Leu Arg Tyr Ala Val Pro
                165                 170                 175

Pro Arg Glu Thr Glu Asp Gln Cys Val Met Val Ile Asp Lys Met Pro
            180                 185                 190

Pro Pro Lys His Gly Lys Met Ser Phe Phe Arg Thr Thr Asn Asp Leu
        195                 200                 205

Ser Lys Leu Pro Leu Gly Met Glu Thr Gly Gly Leu Ser Asp Leu Lys
    210                 215                 220

Leu Ala Gly Cys Glu Arg Ile Ser Ser Val Glu Gln Val Lys Ser Ile
```

```
                225                 230                 235                 240
Arg Ala Ala Leu Gly Gly Pro Leu Thr Val Leu Asp Leu Arg Glu
            245                 250                 255
Glu Ser His Ala Ile Val Asn Gly Leu Pro Ile Thr Leu Arg Gly Pro
        260                 265                 270
Met Asp Trp Ala Asn Ala Gly Leu Ser Gln Val Asp Gly Ala Ala Arg
        275                 280                 285
Glu Ser Ala Met Ile Thr Glu Leu Lys Arg Thr Lys Ser Leu Thr Leu
    290                 295                 300
Val Asp Ala Asn Tyr Val Lys Gly Lys Ser Asn Pro Gln Thr Thr
305                 310                 315                 320
Glu Leu Lys Asn Leu Asn Val Arg Ser Glu Arg Glu Val Val Thr Glu
                325                 330                 335
Ala Gly Ala Thr Tyr Arg Arg Val Ala Ile Thr Asp His Asn Arg Pro
            340                 345                 350
Ser Pro Glu Ala Thr Asp Glu Leu Val Asp Ile Met Arg His Cys Leu
        355                 360                 365
Gln Ala Asn Glu Ser Leu Val Val His Cys Asn Gly Gly Arg Gly Arg
    370                 375                 380
Thr Thr Thr Ala Met Ile Met Val Asp Met Leu Lys Asn Ala Arg Asn
385                 390                 395                 400
His Ser Ala Glu Thr Leu Ile Thr Arg Met Ala Lys Leu Ser Tyr Asp
                405                 410                 415
Tyr Asn Met Thr Asp Leu Gly Ser Ile Ser Ala Leu Lys Arg Pro Phe
            420                 425                 430
Leu Glu Asp Arg Leu Lys Phe Leu Gln Ala Phe His Asp Tyr Ala Arg
        435                 440                 445
Asn Asn Pro Ser Gly Leu Ser Leu Asn Trp Thr Gln Trp Arg Ala Lys
    450                 455                 460
Ile Ala Leu Glu
465
```

<210> SEQ ID NO 13
<211> LENGTH: 810
<212> TYPE: DNA
<213> ORGANISM: Pseudomonas syringae

<400> SEQUENCE: 13

| | | | | |
|---|---|---|---|---|
| atgacaatcg | tgtctggaca | catcggaaaa | cacccaagcc | taaccactgt tcaagctggg | 60 |
| tcttcggctt | cggtcgagaa | tcaaatgcct | gatcctgcac | agttcagtga tggacggtgg | 120 |
| aaaaagcttc | cgacccaatt | gtcgtcaatt | acattggcga | gattcgatca ggatatttgc | 180 |
| acgaataatc | atggcatcag | tcagcgtgca | atgtgctttg | cctttcatt gagctggatt | 240 |
| aacatgattc | atgccgggaa | agatcatgtt | acgccctatg | catcggcaga agaatgagg | 300 |
| tttctgggtt | cctttgaagg | ggtggtgcat | gctcgtactt | tcataactt ctatcggact | 360 |
| gagcacaaat | ttctgatgga | gcaagcttcc | gcaaacccg | gagtatcaag tggcgcgatg | 420 |
| gctggcacag | aaagtttatt | gcaagctgct | gagttgaagg | ggtaaagct tcaacctgtt | 480 |
| ctagaggaca | agtcgaactc | aggcctaccc | ttcctaattg | cgtgtaagca gtcagggcgg | 540 |
| caggtgagca | cagatgaagc | tgcgctaagc | tccttatgtg | atgcaattgt agaaaataag | 600 |
| agagggggtaa | tggtgatata | cagccaagaa | attgcccacg | ctttgggctt ttctgtatca | 660 |
| tcagatggca | aaagagcgac | cttatttgat | cccaatctcg | gagagtttca tacacactcg | 720 |
| aaagcgttgg | ctgatactat | cgaaaacata | tcatcggcag | atgggctgcc tttaatcggc | 780 |

```
gttcaagtat tcgcttcaaa aatacactga                                      810
```

<210> SEQ ID NO 14
<211> LENGTH: 269
<212> TYPE: PRT
<213> ORGANISM: Pseudomonas syringae

<400> SEQUENCE: 14

| Met | Thr | Ile | Val | Ser | Gly | His | Ile | Gly | Lys | His | Pro | Ser | Leu | Thr | Thr |
|---|---|---|---|---|---|---|---|---|---|---|---|---|---|---|---|
| 1 | | | | 5 | | | | | 10 | | | | | 15 | |

| Val | Gln | Ala | Gly | Ser | Ser | Ala | Ser | Val | Glu | Asn | Gln | Met | Pro | Asp | Pro |
| | | | 20 | | | | | 25 | | | | | 30 | | |

| Ala | Gln | Phe | Ser | Asp | Gly | Arg | Trp | Lys | Lys | Leu | Pro | Thr | Gln | Leu | Ser |
| | | 35 | | | | | 40 | | | | | 45 | | | |

| Ser | Ile | Thr | Leu | Ala | Arg | Phe | Asp | Gln | Asp | Ile | Cys | Thr | Asn | Asn | His |
| | 50 | | | | | 55 | | | | | 60 | | | | |

| Gly | Ile | Ser | Gln | Arg | Ala | Met | Cys | Phe | Gly | Leu | Ser | Leu | Ser | Trp | Ile |
| 65 | | | | | 70 | | | | | 75 | | | | | 80 |

| Asn | Met | Ile | His | Ala | Gly | Lys | Asp | His | Val | Thr | Pro | Tyr | Ala | Ser | Ala |
| | | | | 85 | | | | | 90 | | | | | 95 | |

| Glu | Arg | Met | Arg | Phe | Leu | Gly | Ser | Phe | Glu | Gly | Val | Val | His | Ala | Arg |
| | | | 100 | | | | | 105 | | | | | 110 | | |

| Thr | Val | His | Asn | Phe | Tyr | Arg | Thr | Glu | His | Lys | Phe | Leu | Met | Glu | Gln |
| | | 115 | | | | | 120 | | | | | 125 | | | |

| Ala | Ser | Ala | Asn | Pro | Gly | Val | Ser | Ser | Gly | Ala | Met | Ala | Gly | Thr | Glu |
| | 130 | | | | | 135 | | | | | 140 | | | | |

| Ser | Leu | Leu | Gln | Ala | Ala | Glu | Leu | Lys | Gly | Leu | Lys | Leu | Gln | Pro | Val |
| 145 | | | | | 150 | | | | | 155 | | | | | 160 |

| Leu | Glu | Asp | Lys | Ser | Asn | Ser | Gly | Leu | Pro | Phe | Leu | Ile | Ala | Cys | Lys |
| | | | | 165 | | | | | 170 | | | | | 175 | |

| Gln | Ser | Gly | Arg | Gln | Val | Ser | Thr | Asp | Glu | Ala | Ala | Leu | Ser | Ser | Leu |
| | | | 180 | | | | | 185 | | | | | 190 | | |

| Cys | Asp | Ala | Ile | Val | Glu | Asn | Lys | Arg | Gly | Val | Met | Val | Ile | Tyr | Ser |
| | | 195 | | | | | 200 | | | | | 205 | | | |

| Gln | Glu | Ile | Ala | His | Ala | Leu | Gly | Phe | Ser | Val | Ser | Ser | Asp | Gly | Lys |
| | 210 | | | | | 215 | | | | | 220 | | | | |

| Arg | Ala | Thr | Leu | Phe | Asp | Pro | Asn | Leu | Gly | Glu | Phe | His | Thr | His | Ser |
| 225 | | | | | 230 | | | | | 235 | | | | | 240 |

| Lys | Ala | Leu | Ala | Asp | Thr | Ile | Glu | Asn | Ile | Ser | Ser | Ala | Asp | Gly | Leu |
| | | | | 245 | | | | | 250 | | | | | 255 | |

| Pro | Leu | Ile | Gly | Val | Gln | Val | Phe | Ala | Ser | Lys | Ile | His |
| | | | 260 | | | | | 265 | | | | |

<210> SEQ ID NO 15
<211> LENGTH: 831
<212> TYPE: DNA
<213> ORGANISM: Pseudomonas syringae

<400> SEQUENCE: 15

```
atgcacgcaa atcctttaag ctcttcaac agagctcaac atggcaatct gactaatgta      60
gaggccagcc aagttaaatc ggcaggaacc tcttccacca ctaatataga cagtaaaaac     120
attgaagaac atgttgcaga cagactcagt gatttaggca gacctgatgg tggatggttt     180
ttcgagaagt cacttggcac cttgaaaaat ttaaatcttg agcagttagc cggaatccat     240
gatgtactaa aattaacaga tggcgtaaag aacattgtct cttttggagc tcgggaagga     300
```

```
ggcttcgagt tggcaatgca gtttcgtcat gatttataca gatctcaaca tccggatgaa      360
aactcgccgc acgatgccgc aactcattat cttgatgcaa tcagcctgca atcaaacaaa      420
tttacaaaac ttgaaaaact acaacatgta gatgtattta aaatgcaaaa cccgttttgg      480
gatgtcgggt acaaaaacgg aattgcgcac gcaaaaaaaa tggcattctt cataacgcca      540
gagtggctgg gttctgattt ctgtaaacag gaattccagt ggcttagcga aacaaaaaac      600
aaagacataa aatctgcatt tgtgatcttt aaagatgtag acttaaaaag caaaaatatg      660
acaagtatct tcaattttgc agacttccat aaatcacgcg tcatgatggc aagcacacct      720
cccgaatcgg gattgaataa tgtaaaaatc gaaaatagcg ttgacctgaa tttcaagagg      780
ttattaactg accgtgagtc atgggaacta aataatttcc taggcgacta a              831
```

<210> SEQ ID NO 16
<211> LENGTH: 276
<212> TYPE: PRT
<213> ORGANISM: Pseudomonas syringae

<400> SEQUENCE: 16

```
Met His Ala Asn Pro Leu Ser Ser Phe Asn Arg Ala Gln His Gly Asn
  1               5                  10                  15

Leu Thr Asn Val Glu Ala Ser Gln Val Lys Ser Ala Gly Thr Ser Ser
                 20                  25                  30

Thr Thr Asn Ile Asp Ser Lys Asn Ile Glu Glu His Val Ala Asp Arg
             35                  40                  45

Leu Ser Asp Leu Gly Arg Pro Asp Gly Gly Trp Phe Phe Glu Lys Ser
         50                  55                  60

Leu Gly Thr Leu Lys Asn Leu Asn Leu Glu Gln Leu Ala Gly Ile His
 65                  70                  75                  80

Asp Val Leu Lys Leu Thr Asp Gly Val Lys Asn Ile Val Ser Phe Gly
                 85                  90                  95

Ala Arg Glu Gly Gly Phe Glu Leu Ala Met Gln Phe Arg His Asp Leu
            100                 105                 110

Tyr Arg Ser Gln His Pro Asp Glu Asn Ser Pro His Asp Ala Ala Thr
        115                 120                 125

His Tyr Leu Asp Ala Ile Ser Leu Gln Ser Asn Lys Phe Thr Lys Leu
    130                 135                 140

Glu Lys Leu Gln His Val Asp Val Phe Lys Met Gln Asn Pro Phe Trp
145                 150                 155                 160

Asp Val Gly Tyr Lys Asn Gly Ile Ala His Ala Lys Lys Met Ala Phe
                165                 170                 175

Phe Ile Thr Pro Glu Trp Leu Gly Ser Asp Phe Cys Lys Gln Glu Phe
            180                 185                 190

Gln Trp Leu Ser Glu Thr Lys Asn Lys Asp Ile Lys Ser Ala Phe Val
        195                 200                 205

Ile Phe Lys Asp Val Asp Leu Lys Ser Lys Asn Met Thr Ser Ile Phe
    210                 215                 220

Asn Phe Ala Asp Phe His Lys Ser Arg Val Met Met Ala Ser Thr Pro
225                 230                 235                 240

Pro Glu Ser Gly Leu Asn Asn Val Lys Ile Glu Asn Ser Val Asp Leu
                245                 250                 255

Asn Phe Lys Arg Leu Leu Thr Asp Arg Glu Ser Trp Glu Leu Asn Asn
            260                 265                 270

Phe Leu Gly Asp
```

<210> SEQ ID NO 17
<211> LENGTH: 855
<212> TYPE: DNA
<213> ORGANISM: Pseudomonas syringae

<400> SEQUENCE: 17

```
atgggctat gtatttcaaa acactctggt agcagttaca gctacagtga tagcgaccgc      60
tggcaagtgc ctgcatgccc tccaaacgcc aggtctgtat ccagtcatca acagcatct    120
gcgagtgaca tcgcatcagg cgatgtggat gaacgtcctg caacgttttc tcattttcaa   180
cttgcgcggt gcggtggaga gtacacgctt agcatggttt ctgcagcggc ttatcaagca   240
gaaagacggc atcgcggtaa tttaataaaa gatcgtagtc aatccatact cccatgggtc   300
caggtatatc attctaaaaa aggtttggat tacagcttcc agatcgacag aactacgact   360
gttaaagtgg ctggattcaa ctgctctatc cccaataaca gagggactcg catttatac    420
agcgctggta cgagtcagac aaacatgcct gtcatcgcag acaacatgag cgcatgcatt   480
gctgtcgcgt gtgcggcgga aaacgtggat gctggcacgg tgaacgtag gccggggggcg   540
aaagttcgcg tattccatct actcccttttt cgacgcgaag accttgtgcc agaagaagtt   600
ttagcttctg tgcgcgatta tctgcgaacg accaaagaac agggcgtaac aatgcgcgta   660
gctatgcatg gagggaatac agagggtgat ttctcagtca gcactgcgca ggcattgaaa   720
ggcctgtttg ctaatgaagg gatcccgctt gaatttgacg agacctgtgc aaaccgaacg   780
tctgaaacac tgcttggtgc cgttatctta gatgacaact cgactcattt cataaaacat   840
ctggtcgcac aataa                                                      855
```

<210> SEQ ID NO 18
<211> LENGTH: 284
<212> TYPE: PRT
<213> ORGANISM: Pseudomonas syringae

<400> SEQUENCE: 18

```
Met Gly Leu Cys Ile Ser Lys His Ser Gly Ser Ser Tyr Ser Tyr Ser
  1               5                  10                  15

Asp Ser Asp Arg Trp Gln Val Pro Ala Cys Pro Pro Asn Ala Arg Ser
             20                  25                  30

Val Ser Ser His Gln Thr Ala Ser Ala Ser Asp Ile Ala Ser Gly Asp
         35                  40                  45

Val Asp Glu Arg Pro Ala Thr Phe Ser His Phe Gln Leu Ala Arg Cys
     50                  55                  60

Gly Gly Glu Tyr Thr Leu Ser Met Val Ser Ala Ala Tyr Gln Ala
 65                  70                  75                  80

Glu Arg Arg His Arg Gly Asn Leu Ile Lys Asp Arg Ser Gln Ser Ile
                 85                  90                  95

Leu Pro Trp Val Gln Val Tyr His Ser Lys Lys Gly Leu Asp Tyr Ser
            100                 105                 110

Phe Gln Ile Asp Arg Thr Thr Thr Val Lys Val Ala Gly Phe Asn Cys
        115                 120                 125

Ser Ile Pro Asn Asn Arg Gly Thr Arg His Leu Tyr Ser Ala Gly Thr
    130                 135                 140

Ser Gln Thr Asn Met Pro Val Ile Ala Asp Asn Met Ser Ala Cys Ile
145                 150                 155                 160

Ala Val Ala Cys Ala Ala Glu Asn Val Asp Ala Gly Thr Gly Glu Arg
```

```
                165                 170                 175
Arg Pro Gly Ala Lys Val Arg Val Phe His Leu Leu Pro Phe Arg Arg
            180                 185                 190

Glu Asp Leu Val Pro Glu Val Leu Ala Ser Val Arg Asp Tyr Leu
        195                 200                 205

Arg Thr Thr Lys Glu Gln Gly Leu Thr Met Arg Val Ala Met His Gly
        210                 215                 220

Gly Asn Thr Glu Gly Asp Phe Ser Val Ser Thr Ala Gln Ala Leu Lys
225                 230                 235                 240

Gly Leu Phe Ala Asn Glu Gly Ile Pro Leu Glu Phe Asp Glu Thr Cys
                245                 250                 255

Ala Asn Arg Thr Ser Glu Thr Leu Leu Gly Ala Val Ile Leu Asp Asp
            260                 265                 270

Asn Ser Thr His Phe Ile Lys His Leu Val Ala Gln
            275                 280

<210> SEQ ID NO 19
<211> LENGTH: 291
<212> TYPE: DNA
<213> ORGANISM: Pseudomonas syringae

<400> SEQUENCE: 19
atgatcatcg acaatacgtt cgcgctgaca ctgtcatgcg attacgcgcg tgagcgcctg      60
ctgttgatcg gcttgcttga gccgcacaag gacataccct cagcagtgcct tttggctggc    120 gctctcaatc cgctcctcaa tgcaggccca ggccttggcc tggatgagaa aagcggcctg    180
tatcacgcgt atcaaagcat ccctcgagaa aaactcagcg tgccgacgct caaacgcgaa    240
atggcaggtc tgctggagtg gatgaggggc tggcgcgaag caagccaata g              291

<210> SEQ ID NO 20
<211> LENGTH: 96
<212> TYPE: PRT
<213> ORGANISM: Pseudomonas syringae

<400> SEQUENCE: 20

Met Ile Ile Asp Asn Thr Phe Ala Leu Thr Leu Ser Cys Asp Tyr Ala
1               5                   10                  15

Arg Glu Arg Leu Leu Leu Ile Gly Leu Leu Glu Pro His Lys Asp Ile
            20                  25                  30

Pro Gln Gln Cys Leu Leu Ala Gly Ala Leu Asn Pro Leu Leu Asn Ala
        35                  40                  45

Gly Pro Gly Leu Gly Leu Asp Glu Lys Ser Gly Leu Tyr His Ala Tyr
    50                  55                  60

Gln Ser Ile Pro Arg Glu Lys Leu Ser Val Pro Thr Leu Lys Arg Glu
65                  70                  75                  80

Met Ala Gly Leu Leu Glu Trp Met Arg Gly Trp Arg Glu Ala Ser Gln
                85                  90                  95

<210> SEQ ID NO 21
<211> LENGTH: 1143
<212> TYPE: DNA
<213> ORGANISM: Pseudomonas syringae

<400> SEQUENCE: 21
atgaacccca ttcagtcacg cttctccagt gtgcaagagc tcagacgatc caacgttgat       60
attccggcgc tcaaagccaa tggccaactg gaggtcgacg caagaggta cgagattcgt      120
```

-continued

```
gcagccgatg acggaacaat tcgtgtcctt cgaccggagc aacaatccaa agcgaaaagt    180 ttttcaagg gcgcttccca gttgataggt ggcagcagcc agcgcgcgca gattgcccag    240
gcgctcaacg agaaggtcgc atcggcacgc actgtcttgc accagagcgc tatgacgggc    300
ggacgcttgg acaccttga gcggggcgaa agcagctcag ccacaacagc catcaaaccc    360
actgccaaac aggctgcgca agtactttt aacagctttc atgagtgggc aaacaggca    420 gaggcgatgc gaaacccgtc tcgaatggat atctacaaga tctataaaca agatgcacct    480
cactcacacc ccatgagcga cgagcagcaa gaagagttcc tgcacacgct aaaggcattg    540
aatggcaaaa acggcattga ggtgcgcact caggaccacg acagcgtcag aaataaaaaa    600
gaccgcaacc tggacaagta catcgcagag agcccggatg caaagaggtt tttctatcga    660
attatcccca acatgagcg ccgagaagat aagaatcaag gcgattgac cattggcgtg    720 caaccccaat atgcaacaca gttgacccgc gccatggcaa ccctgatagg aaggaaagt    780 gcaatcacgc atggcaaagt aataggcccc gcctgccacg gccaaatgac cgattcggca    840
gttttgtata tcaacggtga tgttgcaaag gcagaaaagc tgggcgagaa actgaaacag    900
atgagcggca ttcctctgga tgcgttcgtt gagcacaccc cttgagcat gcaatccctg    960 agtaaaggtc tgtcctatgc agaaagcatc ctgggcgaca ccagaggcca tgggatgtcg    1020
cgagcggaag tgatcagcga tgccttgagg atggacggga tgccatttct ggccagattg    1080
aagctatcac tgtctgccaa tggctatgac ccggacaacc cggcccttcg aaacacgaaa    1140
tga                                                                  1143
```

<210> SEQ ID NO 22
<211> LENGTH: 380
<212> TYPE: PRT
<213> ORGANISM: Pseudomonas syringae

<400> SEQUENCE: 22

```
Met Asn Pro Ile Gln Ser Arg Phe Ser Ser Val Gln Glu Leu Arg Arg
  1               5                  10                  15

Ser Asn Val Asp Ile Pro Ala Leu Lys Ala Asn Gly Gln Leu Glu Val
                 20                  25                  30

Asp Gly Lys Arg Tyr Glu Ile Arg Ala Ala Asp Gly Thr Ile Ser
         35                  40                  45

Val Leu Arg Pro Glu Gln Gln Ser Lys Ala Lys Ser Phe Phe Lys Gly
     50                  55                  60

Ala Ser Gln Leu Ile Gly Gly Ser Ser Gln Arg Ala Gln Ile Ala Gln
 65                  70                  75                  80

Ala Leu Asn Glu Lys Val Ala Ser Ala Arg Thr Val Leu His Gln Ser
                 85                  90                  95

Ala Met Thr Gly Gly Arg Leu Asp Thr Leu Glu Arg Gly Glu Ser Ser
                100                 105                 110

Ser Ala Thr Thr Ala Ile Lys Pro Thr Ala Lys Gln Ala Ala Gln Ser
            115                 120                 125

Thr Phe Asn Ser Phe His Glu Trp Ala Lys Gln Ala Glu Ala Met Arg
        130                 135                 140

Asn Pro Ser Arg Met Asp Ile Tyr Lys Ile Tyr Lys Gln Asp Ala Pro
145                 150                 155                 160

His Ser His Pro Met Ser Asp Glu Gln Gln Glu Glu Phe Leu His Thr
                165                 170                 175

Leu Lys Ala Leu Asn Gly Lys Asn Gly Ile Glu Val Arg Thr Gln Asp
            180                 185                 190
```

-continued

```
His Asp Ser Val Arg Asn Lys Lys Asp Arg Asn Leu Asp Lys Tyr Ile
            195                 200                 205

Ala Glu Ser Pro Asp Ala Lys Arg Phe Phe Tyr Arg Ile Ile Pro Lys
    210                 215                 220

His Glu Arg Arg Glu Asp Lys Asn Gln Gly Arg Leu Thr Ile Gly Val
225                 230                 235                 240

Gln Pro Gln Tyr Ala Thr Gln Leu Thr Arg Ala Met Ala Thr Leu Ile
                245                 250                 255

Gly Lys Glu Ser Ala Ile Thr His Gly Lys Val Ile Gly Pro Ala Cys
            260                 265                 270

His Gly Gln Met Thr Asp Ser Ala Val Leu Tyr Ile Asn Gly Asp Val
        275                 280                 285

Ala Lys Ala Glu Lys Leu Gly Glu Lys Leu Lys Gln Met Ser Gly Ile
    290                 295                 300

Pro Leu Asp Ala Phe Val Glu His Thr Pro Leu Ser Met Gln Ser Leu
305                 310                 315                 320

Ser Lys Gly Leu Ser Tyr Ala Glu Ser Ile Leu Gly Asp Thr Arg Gly
                325                 330                 335

His Gly Met Ser Arg Ala Glu Val Ile Ser Asp Ala Leu Arg Met Asp
            340                 345                 350

Gly Met Pro Phe Leu Ala Arg Leu Lys Leu Ser Leu Ser Ala Asn Gly
        355                 360                 365

Tyr Asp Pro Asp Asn Pro Ala Leu Arg Asn Thr Lys
    370                 375                 380

<210> SEQ ID NO 23
<211> LENGTH: 2598
<212> TYPE: DNA
<213> ORGANISM: Pseudomonas syringae

<400> SEQUENCE: 23
gtgccgcgta tcgtcgccgg ccatgcagaa ggcgtgtgcg tggtcaacgg ccggcactat      60
gtcgagctgt ccggtagaac ctttcaagtc cattacgaca cacatctgcg cggctggcag     120
attgtcgatc cagaaaaccc gttcgccttt tttggccagc agccggtgcg cctagatgaa     180
cagggggcaat ggcagcttgt cgcccgtcga cgtctgcgtg gcgtggcgt aggtgactcc     240
agccatgccc acctgcccga gaaacaccg gctccagca caggctcgat tccgagcgac     300
tacgaaatgc cggccgccat gcaggcaggc cttgatgtcg tgttgagcaa caagccctac     360
gacccgaccg ggattggcat ggagtcttac tttgagagct atttcgtgga tctgcgtcag     420
agttttgtgg cgcgcaggga aaagctttat gaggatgccc ggacattttt cgccggtttt     480
tctccgccgc caaagccgca attgcctccg ctggcgccac ctgttgccat cgacaccctg     540
attgaacacg tcttcgcgca gggtaacggc ctggttttga gtgaagcacc gaagtcggtc     600
gccagcaaac ggctgctgtt actcaacatg ccgctgctgg ccgaacagcg tgtcaagatt     660
ctgtatatcg agcacctgct gaccgacaag cacctgtcta aactggccag gtatcgtcaa     720
ctgggcaaaa agagccgctc aggctcgcac gaactcaagc attacctgca cgatctcaac     780
cgcgggacgc tgaacaattc cagcaccgac tacgactatt accacctcat caaggcagcg     840
catcgctatg gtatcgaggt gcgaccgttc agctcgtcga tcagctaccc gtttctggac     900
catccggtat tgagcgcagc caacgacacg actgcagtac aaaaaaatgag caatttttc      960
ggccatacgc tcatcagcag cgatgtcgca tccgcgccga caaaacgctg ggttgccttg    1020
```

-continued

```
ctcgaccaga agctggccac gacccacgac ggggtattag gcattgccga aatgcagggc    1080
gtggtcagtg tgcatgtccg cgacatcccg gcaggccggc cgacgcgcat cactaaaggc    1140
acaggcgaac tgccacgcga gggcacgcag gcccgctgcg acttcacgat tgcgttttcc    1200
gatccgacgc tgattgtgcc ccaggcgcct caccccgcacg gtaccaaact ggacgacatg    1260
ctgctcagag aactgagggg ccaatctgcc ggtgccgggg cgaacgctg ggccggccag     1320 tacggattca tccgtgacga ggacggtgcc tggcggtgga tcgcgcctga ggactggccc    1380
gcagacagcc cgatgacggc aatccagcaa tccctgaccg accctgtcta tgagatgcca    1440
ctggacactc gaacaacgct tcatacgctg gcgaacttcg aaagaagggg gctcgacatg    1500
gagtatttct ttgaagaaag ccagtacgaa actgttcgca acgtattcgc cctgcaccgc    1560
aaaaagctgc aacaggatgc ggccttgatc agcgctgtac agttgccgcc tcgtccgacg    1620
atgccggccg tcaaccctcg acgaccacg gcgcagctgt ttgaaacgct gtaccagcac     1680
accgatggca tcgtgatcgg cgagtcgcat ttttcggtcg ccagcaagaa aatgatcatc    1740
gacaacctgc cgttgctgtc gcagcaaaac gtacgaacgc tgtacatgga gcacttgctc    1800
accgacttgc atcaggcgga tctggatcgc ttttttcgaaa cagggcaaat gagcaaaacc    1860
ctgcttcacg acctgaaagt gctggatcgg ggccatcgca ccgacccgga caaggtttac    1920
acctttgagc aactggtcat caaggcgcag cagcacggca tggaagtccg cgccatcgac    1980
tgcgcagcca gctaccacct tagtggcctt gacaacgatg gttcaatcac ccgtcagcaa    2040
atgatgaact actttgcgtc gcgcaccctg cgcaggcatc aggacgtcat gggctcacac    2100
aagtggatcg cgctggtcgg caacagccat tccaatgtct atcaaggcgt cgtgcctggt    2160
atcgccgagc tggaaggcgg catcggcctg cgggttatcg acgtggcacc ggggcagtcg    2220
aagggtgtca tgcacgacct ggggagctg gtctcggcag acatctcgag aaccaaagta     2280
cacatcaaag gcgattatcg agtggagata gaaataccgc gtgcgaagga tgccattcgg    2340
ccaccccagc ctgttacct cgaacagcga ctggccagac cgggattgtt tctggtggaa     2400
gagagtgagg gcaatctgct gaccattgtc caccgcgctc gcgacacctg gattcaccgc    2460
acgccggtgc tggtcaatgc cgagggcaag ctgtacctgg agcgcgtgcg ctggccgcgc    2520
atccacctca aacccttga tgacatggac gcgctggtag cggcgctgga ggagatgaac     2580
ctgacgcggg taggctga                                                 2598
```

<210> SEQ ID NO 24
<211> LENGTH: 865
<212> TYPE: PRT
<213> ORGANISM: Pseudomonas syringae

<400> SEQUENCE: 24

```
Val Pro Arg Ile Val Ala Gly His Ala Glu Gly Val Cys Val Val Asn
  1               5                  10                  15

Gly Arg His Tyr Val Glu Leu Ser Gly Arg Thr Phe Gln Val His Tyr
                 20                  25                  30

Asp Thr His Leu Arg Gly Trp Gln Ile Val Asp Pro Glu Asn Pro Phe
             35                  40                  45

Ala Phe Phe Gly Gln Gln Pro Val Arg Leu Asp Glu Gln Gly Gln Trp
         50                  55                  60

Gln Leu Val Ala Arg Arg Arg Leu Arg Gly Gly Val Gly Asp Ser
 65                  70                  75                  80

Ser His Ala His Leu Pro Glu Glu Thr Pro Gly Ser Ser Thr Gly Ser
                 85                  90                  95
```

```
Ile Pro Ser Asp Tyr Glu Met Pro Ala Ala Met Gln Ala Gly Leu Asp
            100                 105                 110

Val Val Leu Ser Asn Lys Pro Tyr Asp Pro Thr Gly Ile Gly Met Glu
            115                 120                 125

Ser Tyr Phe Glu Ser Tyr Phe Val Asp Leu Arg Gln Ser Phe Val Ala
            130                 135                 140

Arg Arg Glu Lys Leu Tyr Glu Asp Ala Arg Thr Phe Phe Ala Gly Phe
145                 150                 155                 160

Ser Pro Pro Lys Pro Gln Leu Pro Pro Leu Ala Pro Pro Val Ala
                165                 170                 175

Ile Asp Thr Leu Ile Glu His Val Phe Ala Gln Gly Asn Gly Leu Val
            180                 185                 190

Leu Ser Glu Ala Pro Lys Ser Val Ala Ser Lys Arg Leu Leu Leu
            195                 200                 205

Asn Met Pro Leu Leu Ala Glu Gln Arg Val Lys Ile Leu Tyr Ile Glu
210                 215                 220

His Leu Leu Thr Asp Lys His Leu Ser Lys Leu Ala Arg Tyr Arg Gln
225                 230                 235                 240

Leu Gly Lys Lys Ser Arg Ser Gly Ser His Glu Leu Lys His Tyr Leu
                245                 250                 255

His Asp Leu Asn Arg Gly Thr Leu Asn Asn Ser Ser Thr Asp Tyr Asp
            260                 265                 270

Tyr Tyr His Leu Ile Lys Ala Ala His Arg Tyr Gly Ile Glu Val Arg
            275                 280                 285

Pro Phe Ser Ser Ser Ile Ser Tyr Pro Phe Leu Asp His Pro Val Leu
            290                 295                 300

Ser Ala Ala Asn Asp Thr Thr Ala Val Gln Lys Met Ser Asn Phe Phe
305                 310                 315                 320

Gly His Thr Leu Ile Ser Ser Asp Val Ala Ser Ala Pro Thr Lys Arg
            325                 330                 335

Trp Val Ala Leu Leu Asp Gln Lys Leu Ala Thr Thr His Asp Gly Val
            340                 345                 350

Leu Gly Ile Ala Glu Met Gln Gly Val Val Ser Val His Val Arg Asp
            355                 360                 365

Ile Pro Ala Gly Arg Pro Thr Arg Ile Thr Lys Gly Thr Gly Glu Leu
            370                 375                 380

Pro Arg Glu Gly Thr Gln Ala Arg Cys Asp Phe Thr Ile Ala Phe Ser
385                 390                 395                 400

Asp Pro Thr Leu Ile Val Pro Gln Ala Pro His Pro Gly Thr Lys
            405                 410                 415

Leu Asp Asp Met Leu Leu Arg Glu Leu Arg Gly Gln Ser Ala Gly Ala
            420                 425                 430

Gly Gly Glu Arg Trp Ala Gly Gln Tyr Gly Phe Ile Arg Asp Glu Asp
            435                 440                 445

Gly Ala Trp Arg Trp Ile Ala Pro Glu Asp Trp Pro Ala Asp Ser Pro
            450                 455                 460

Met Thr Ala Ile Gln Gln Ser Leu Thr Asp Pro Val Tyr Glu Met Pro
465                 470                 475                 480

Leu Asp Thr Arg Thr Thr Leu His Thr Leu Ala Asn Phe Glu Arg Arg
            485                 490                 495

Gly Leu Asp Met Glu Tyr Phe Phe Glu Glu Ser Gln Tyr Glu Thr Val
            500                 505                 510
```

```
Arg Asn Val Phe Ala Leu His Arg Lys Lys Leu Gln Gln Asp Ala Ala
        515                 520                 525

Leu Ile Ser Ala Val Gln Leu Pro Pro Arg Pro Thr Met Pro Ala Val
        530                 535                 540

Asn Pro Arg Thr Thr Thr Ala Gln Leu Phe Glu Thr Leu Tyr Gln His
545                 550                 555                 560

Thr Asp Gly Ile Val Ile Gly Glu Ser His Phe Ser Val Ala Ser Lys
                565                 570                 575

Lys Met Ile Ile Asp Asn Leu Pro Leu Leu Ser Gln Gln Asn Val Arg
                580                 585                 590

Thr Leu Tyr Met Glu His Leu Leu Thr Asp Leu His Gln Ala Asp Leu
        595                 600                 605

Asp Arg Phe Phe Glu Thr Gly Gln Met Ser Lys Thr Leu Leu His Asp
        610                 615                 620

Leu Lys Val Leu Asp Arg Gly His Arg Thr Asp Pro Asp Lys Val Tyr
625                 630                 635                 640

Thr Phe Glu Gln Leu Val Ile Lys Ala Gln Gln His Gly Met Glu Val
                645                 650                 655

Arg Ala Ile Asp Cys Ala Ala Ser Tyr His Leu Ser Gly Leu Asp Asn
                660                 665                 670

Asp Gly Ser Ile Thr Arg Gln Gln Met Met Asn Tyr Phe Ala Ser Arg
        675                 680                 685

Thr Leu Arg Arg His Gln Asp Val Met Gly Ser His Lys Trp Ile Ala
        690                 695                 700

Leu Val Gly Asn Ser His Ser Asn Val Tyr Gln Gly Val Val Pro Gly
705                 710                 715                 720

Ile Ala Glu Leu Glu Gly Gly Ile Gly Leu Arg Val Ile Asp Val Ala
                725                 730                 735

Pro Gly Gln Ser Lys Gly Val Met His Asp Leu Gly Glu Leu Val Ser
                740                 745                 750

Ala Asp Ile Ser Arg Thr Lys Val His Ile Lys Gly Asp Tyr Arg Val
        755                 760                 765

Glu Ile Glu Ile Pro Arg Ala Lys Asp Ala Ile Arg Pro Pro Gln Pro
        770                 775                 780

Val Thr Leu Glu Gln Arg Leu Ala Arg Pro Gly Leu Phe Leu Val Glu
785                 790                 795                 800

Glu Ser Glu Gly Asn Leu Leu Thr Ile Val His Arg Ala Arg Asp Thr
                805                 810                 815

Trp Ile His Arg Thr Pro Val Leu Val Asn Ala Glu Gly Lys Leu Tyr
                820                 825                 830

Leu Glu Arg Val Arg Trp Pro Arg Ile His Leu Lys Pro Phe Asp Asp
        835                 840                 845

Met Asp Ala Leu Val Ala Ala Leu Glu Glu Met Asn Leu Thr Arg Val
        850                 855                 860

Gly
865

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: human
      immunodeficiency virus, TAT protein transduction
      domain
```

```
<400> SEQUENCE: 25

Tyr Gly Arg Lys Lys Arg Arg Gln Arg Arg
  1               5                  10

<210> SEQ ID NO 26
<211> LENGTH: 42
<212> TYPE: DNA
<213> ORGANISM: Artificial Sequence
<220> FEATURE:
<223> OTHER INFORMATION: Description of Artificial Sequence: hopPtoC
      primer

<400> SEQUENCE: 26
agtcggatcc gaatagggcg ctgaaaatat gacaatcgtg tc                          42

<210> SEQ ID NO 27
<211> LENGTH: 55
<212> TYPE: DNA
<213> ORGANISM: Artificial Sequence
<220> FEATURE:
<223> OTHER INFORMATION: Description of Artificial Sequence: hopPtoC
      primer

<400> SEQUENCE: 27
agtcctcgag tcacttgtca tcgtcgtcct tgtagtcgtg tatttttgaa gcgaa           55

<210> SEQ ID NO 28
<211> LENGTH: 45
<212> TYPE: DNA
<213> ORGANISM: Artificial Sequence
<220> FEATURE:
<223> OTHER INFORMATION: Description of Artificial Sequence: hopPtoD1
      primer

<400> SEQUENCE: 28
ccacacattg gatccgatta cttcatccgg gacagctgat agcgc                       45

<210> SEQ ID NO 29
<211> LENGTH: 55
<212> TYPE: DNA
<213> ORGANISM: Artificial Sequence
<220> FEATURE:
<223> OTHER INFORMATION: Description of Artificial Sequence: hopPtoD1
      primer

<400> SEQUENCE: 29
attctcgagt catttatcat catcatcttt ataatcgggt gcgggctgcc gcgac           55

<210> SEQ ID NO 30
<211> LENGTH: 28
<212> TYPE: DNA
<213> ORGANISM: Artificial Sequence
<220> FEATURE:
<223> OTHER INFORMATION: Description of Artificial Sequence: hopPtoD2
      primer

<400> SEQUENCE: 30
atgcaagctt atccaatgcc tttcgtca                                          28

<210> SEQ ID NO 31
<211> LENGTH: 58
<212> TYPE: DNA
<213> ORGANISM: Artificial Sequence
<220> FEATURE:
<223> OTHER INFORMATION: Description of Artificial Sequence: hopPtoD2
      primer
```

```
<400> SEQUENCE: 31
atgcctcgag tcaagcgtaa tctggaacat cgtatgggta ttctaacgct attttttgc        58

<210> SEQ ID NO 32
<211> LENGTH: 28
<212> TYPE: DNA
<213> ORGANISM: Artificial Sequence
<220> FEATURE:
<223> OTHER INFORMATION: Description of Artificial Sequence: hopPtoJ
      primer

<400> SEQUENCE: 32
agtaaagctt gagctgcacg catgcgag                                          28

<210> SEQ ID NO 33
<211> LENGTH: 55
<212> TYPE: DNA
<213> ORGANISM: Artificial Sequence
<220> FEATURE:
<223> OTHER INFORMATION: Description of Artificial Sequence: hopPtoJ
      primer

<400> SEQUENCE: 33
agtatctaga tcacttgtca tcgtcgtcct tgtagtcttg tgcgaccaga tgttt            55

<210> SEQ ID NO 34
<211> LENGTH: 29
<212> TYPE: DNA
<213> ORGANISM: Artificial Sequence
<220> FEATURE:
<223> OTHER INFORMATION: Description of Artificial Sequence: hopPtoK
      primer

<400> SEQUENCE: 34
gcgaattcat cggtttaatc acgcaaggc                                         29

<210> SEQ ID NO 35
<211> LENGTH: 25
<212> TYPE: DNA
<213> ORGANISM: Artificial Sequence
<220> FEATURE:
<223> OTHER INFORMATION: Description of Artificial Sequence: hopPtoK
      primer

<400> SEQUENCE: 35
ttggtacctc agcagtagag cgtgt                                             25

<210> SEQ ID NO 36
<211> LENGTH: 26
<212> TYPE: DNA
<213> ORGANISM: Artificial Sequence
<220> FEATURE:
<223> OTHER INFORMATION: Description of Artificial Sequence: hopPtoK
      primer

<400> SEQUENCE: 36
aaggatccgc agagcgtgtc gcgacc                                            26
```